(12) United States Patent
Lindhout et al.

(10) Patent No.: US 9,834,586 B2
(45) Date of Patent: Dec. 5, 2017

(54) COMPOSITIONS AND METHODS OF USE FOR TREATING METABOLIC DISORDERS

(71) Applicant: NGM Biopharmaceuticals, Inc., South San Francisco, CA (US)

(72) Inventors: Darrin Anthony Lindhout, Mountain View, CA (US); Raj Haldankar, Redwood City, CA (US); Hui Tian, Foster City, CA (US); Jer-Yuan Hsu, San Bruno, CA (US)

(73) Assignee: NGM Biopharmaceuticals, Inc., South San Francisco, CA (US)

(*) Notice: Subject to any disclaimer, the term of this patent is extended or adjusted under 35 U.S.C. 154(b) by 0 days.

(21) Appl. No.: 14/811,578

(22) Filed: Jul. 28, 2015

(65) Prior Publication Data
US 2016/0031960 A1    Feb. 4, 2016

Related U.S. Application Data

(60) Provisional application No. 62/031,063, filed on Jul. 30, 2014, provisional application No. 62/195,908, filed on Jul. 23, 2015.

(51) Int. Cl.

| | | |
|---|---|---|
| A61K 38/16 | (2006.01) | |
| A61K 38/17 | (2006.01) | |
| A61K 38/18 | (2006.01) | |
| C07K 14/435 | (2006.01) | |
| C07K 14/475 | (2006.01) | |
| C12N 1/21 | (2006.01) | |
| C12N 5/10 | (2006.01) | |
| C12N 15/12 | (2006.01) | |
| C12N 15/63 | (2006.01) | |
| C07K 14/495 | (2006.01) | |
| A61K 9/00 | (2006.01) | |
| A61K 38/00 | (2006.01) | |

(52) U.S. Cl.
CPC .......... *C07K 14/495* (2013.01); *A61K 9/0019* (2013.01); *A61K 38/00* (2013.01); *C07K 2319/02* (2013.01); *C07K 2319/30* (2013.01); *C07K 2319/31* (2013.01); *C07K 2319/91* (2013.01)

(58) Field of Classification Search
None
See application file for complete search history.

(56) References Cited

U.S. PATENT DOCUMENTS

| | | | |
|---|---|---|---|
| 5,194,596 A * | 3/1993 | Tischer | C07K 14/46 530/350 |
| 5,350,836 A * | 9/1994 | Kopchick | A01K 67/0275 435/69.4 |
| 5,876,969 A | 3/1999 | Fleer et al. | |
| 5,994,102 A | 11/1999 | Hudson et al. | |
| 6,051,424 A | 4/2000 | Kato et al. | |
| 6,107,476 A | 8/2000 | Erlander et al. | |
| 6,165,470 A | 12/2000 | Becquart et al. | |
| 6,180,602 B1 | 1/2001 | Kato et al. | |
| 6,420,543 B1 | 7/2002 | Lee et al. | |
| 6,465,181 B2 | 10/2002 | Biling-Medel et al. | |
| 6,500,638 B2 | 12/2002 | Hudson et al. | |
| 6,521,227 B1 | 2/2003 | Hudson et al. | |
| 6,524,802 B1 | 2/2003 | Lee et al. | |
| 6,686,179 B2 | 2/2004 | Fleer et al. | |
| 6,905,688 B2 | 6/2005 | Rosen et al. | |
| 6,972,322 B2 | 12/2005 | Fleer et al. | |
| 6,989,365 B2 | 1/2006 | Fleer et al. | |
| 7,056,701 B2 | 6/2006 | Fleer et al. | |
| 7,081,354 B2 | 7/2006 | Fleer et al. | |
| 7,094,577 B2 | 8/2006 | Fleer et al. | |
| 7,141,661 B2 | 11/2006 | Eling et al. | |
| 7,157,235 B2 | 1/2007 | Breit et al. | |
| 7,244,833 B2 | 7/2007 | Yu et al. | |
| 7,276,593 B2 | 10/2007 | Vernet et al. | |
| 7,282,351 B2 | 10/2007 | Hudson et al. | |
| 7,348,004 B2 | 3/2008 | Peters et al. | |
| 7,410,779 B2 | 8/2008 | Fleer et al. | |
| 7,435,410 B2 | 10/2008 | Fleer et al. | |
| 7,442,371 B2 | 10/2008 | Yu et al. | |
| 7,514,221 B2 | 4/2009 | Breit et al. | |
| 7,754,689 B2 | 7/2010 | Lu et al. | |
| 7,833,521 B2 | 11/2010 | Fleer et al. | |
| 7,863,239 B2 | 1/2011 | Timmerman et al. | |
| 7,919,084 B2 | 4/2011 | Breit et al. | |
| 7,968,303 B2 | 6/2011 | Breit et al. | |
| 8,021,880 B2 | 9/2011 | Peters et al. | |
| 8,067,548 B2 | 11/2011 | Wang et al. | |
| 8,084,021 B2 | 12/2011 | Yu et al. | |
| 8,192,735 B2 | 6/2012 | Breit et al. | |

(Continued)

FOREIGN PATENT DOCUMENTS

| | | |
|---|---|---|
| EP | 1179067 | 12/2006 |
| EP | 1279039 | 1/2008 |

(Continued)

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Tokuriki et al., 2009, Curr. Opin. Struc. Biol. 19:596-604.*
Benjamin et al., 1998, Development 125:1591-1598.*
Vukicevic et al., 1996, PNAS USA 93:9021-9026.*
Shen et al., 2004, Eur. J. Neurosci. 20:2031-2037.*
Massague, 1987, Cell 49:437-8.*
U.S. Appl. No. 14/846,194, filed Sep. 4, 2015, Matern, Hugo, et al.
U.S. Appl. No. 14/763,262, filed Jul. 24, 2015, Matern, Hugo, et al.
Bauskin et al. (2000) "The Propeptide of Macrophage Inhibitory Cytokine (MIC-1), a TGF-b Superfamily Member, Acts as a Quality Control Determinant for Correctly Folded MIC-1" *EMBO J* 19:2212-2220.

(Continued)

*Primary Examiner* — Elizabeth C Kemmerer
(74) *Attorney, Agent, or Firm* — Shweta Chandra; Carol L. Francis; Bozicevic, Field & Francis LLP

(57) ABSTRACT

Methods of treating individuals with a glucose metabolism disorder and/or a body weight disorder, and compositions associated therewith, are provided.

61 Claims, 16 Drawing Sheets

(56) References Cited

U.S. PATENT DOCUMENTS

| | | |
|---|---|---|
| 8,222,384 B2 | 7/2012 | Wolfman et al. |
| 8,252,739 B2 | 8/2012 | Rosen et al. |
| 8,592,562 B2 | 11/2013 | Kannan et al. |
| 8,946,146 B2 | 2/2015 | Breit et al. |
| 8,986,698 B2 | 3/2015 | Arnason et al. |
| 9,161,966 B2 | 10/2015 | Matern et al. |
| 2001/0011077 A1 | 8/2001 | Albone et al. |
| 2003/0023073 A1 | 1/2003 | Hsiao et al. |
| 2003/0053431 A1 | 3/2003 | Madour et al. |
| 2003/0232347 A1 | 12/2003 | Anderson et al. |
| 2003/0232385 A1 | 12/2003 | Breit et al. |
| 2004/0029770 A1 | 2/2004 | Baek et al. |
| 2004/0053325 A1 | 3/2004 | Breit et al. |
| 2004/0253207 A1 | 12/2004 | Hruska et al. |
| 2006/0148709 A1 | 7/2006 | Unsicker et al. |
| 2006/0253913 A1 | 11/2006 | Huang et al. |
| 2007/0077598 A1 | 4/2007 | Breit et al. |
| 2007/0166310 A1 | 7/2007 | Hudson et al. |
| 2009/0004181 A1 | 1/2009 | Breit et al. |
| 2009/0042780 A1 | 2/2009 | Knopf et al. |
| 2009/0291889 A1 | 11/2009 | Breit et al. |
| 2010/0112692 A1 | 5/2010 | Rezania et al. |
| 2010/0184217 A1 | 7/2010 | Cegilski et al. |
| 2010/0221777 A1 | 9/2010 | Choe et al. |
| 2010/0261284 A1 | 10/2010 | Spanuth |
| 2010/0266707 A1 | 10/2010 | Breit et al. |
| 2010/0278843 A1 | 11/2010 | Breit et al. |
| 2010/0286067 A1 | 11/2010 | DeFrees |
| 2011/0033886 A1 | 2/2011 | Hess et al. |
| 2011/0039284 A1 | 2/2011 | Breit et al. |
| 2011/0065204 A1 | 3/2011 | Wollert et al. |
| 2011/0107821 A1 | 5/2011 | Hess et al. |
| 2011/0123454 A1 | 5/2011 | Breit et al. |
| 2011/0257022 A1 | 10/2011 | Hess et al. |
| 2011/0262444 A1 | 10/2011 | Kim et la. |
| 2011/0263443 A1 | 10/2011 | Hess et al. |
| 2011/0300562 A1 | 12/2011 | Lambrecht et al. |
| 2012/0107420 A1 | 5/2012 | Breit et al. |
| 2012/0128624 A1 | 5/2012 | Yu et al. |
| 2012/0309697 A1 | 12/2012 | Breit et al. |
| 2013/0004484 A1 | 1/2013 | Demeule et al. |
| 2013/0071935 A1 | 3/2013 | Bergman et al. |
| 2013/0323835 A1 | 12/2013 | McDonald et al. |
| 2014/0044674 A1 | 2/2014 | Duerner et al. |
| 2014/0086915 A1 | 3/2014 | Breit et al. |
| 2014/0113370 A1 | 4/2014 | Camphausen et al. |
| 2014/0193427 A1 | 7/2014 | Lerner et al. |
| 2014/0199294 A1 | 7/2014 | Mimoto et al. |
| 2014/0213511 A1 | 7/2014 | Matern et al. |
| 2014/0314711 A1 | 10/2014 | Scheer et al. |
| 2015/0023960 A1 | 1/2015 | Lindhout et al. |
| 2015/0322081 A1 | 11/2015 | Hoehn |
| 2016/0031960 A1 | 2/2016 | Lindhout et al. |
| 2016/0120999 A1 | 5/2016 | Shen et al. |

FOREIGN PATENT DOCUMENTS

| | | |
|---|---|---|
| EP | 1914554 | 4/2008 |
| EP | 0833912 | 2/2009 |
| EP | 2383571 | 11/2011 |
| EP | 2439535 | 4/2012 |
| EP | 2441466 | 4/2012 |
| EP | 2774620 A1 | 9/2014 |
| EP | 2929891 A1 | 10/2015 |
| JP | 07-258293 | 10/1995 |
| JP | 1995250688 | 10/1995 |
| JP | 2007258293 | 10/1995 |
| WO | WO94/03599 | 2/1994 |
| WO | WO9403599 | 2/1994 |
| WO | WO96/18730 | 6/1996 |
| WO | WO9618730 | 6/1996 |
| WO | WO97/00958 | 1/1997 |
| WO | WO9700958 | 1/1997 |
| WO | WO97/36926 | 10/1997 |
| WO | WO9736926 | 10/1997 |
| WO | WO98/11224 | 3/1998 |
| WO | WO9811224 | 3/1998 |
| WO | WO99/06445 | 2/1999 |
| WO | WO9906445 | 2/1999 |
| WO | WO01/81928 | 11/2001 |
| WO | WO0181928 | 11/2001 |
| WO | WO02/092620 | 11/2002 |
| WO | WO02092620 | 11/2002 |
| WO | WO2005/099746 | 10/2005 |
| WO | WO2005099746 | 10/2005 |
| WO | WO2005/113585 | 12/2005 |
| WO | WO2005113585 | 12/2005 |
| WO | WO03/000448 | 1/2006 |
| WO | WO2006000448 | 1/2006 |
| WO | WO 2008-013454 | 1/2008 |
| WO | WO2009/021293 | 2/2009 |
| WO | WO2009021293 | 2/2009 |
| WO | WO2009/046495 | 4/2009 |
| WO | WO2009046495 | 4/2009 |
| WO | 2009089004 | 7/2009 |
| WO | WO2009/141357 | 11/2009 |
| WO | WO2009141357 | 11/2009 |
| WO | WO 2010/019263 | 2/2010 |
| WO | WO2010/048670 | 5/2010 |
| WO | WO2010048670 | 5/2010 |
| WO | 2010093925 | 8/2010 |
| WO | WO2010/099219 | 9/2010 |
| WO | WO2010099219 | 9/2010 |
| WO | 2010129503 | 11/2010 |
| WO | WO 2010/129503 | 11/2010 |
| WO | 2011005621 | 1/2011 |
| WO | 2011057120 | 5/2011 |
| WO | WO2011/050407 | 5/2011 |
| WO | WO2011050407 | 5/2011 |
| WO | WO2011/064758 | 6/2011 |
| WO | WO2011064758 | 6/2011 |
| WO | WO2011/127458 | 10/2011 |
| WO | WO2011127458 | 10/2011 |
| WO | WO2012/025355 | 3/2012 |
| WO | WO2012025355 | 3/2012 |
| WO | WO2012/138919 | 10/2012 |
| WO | WO2012138919 | 10/2012 |
| WO | WO2013/113008 | 8/2013 |
| WO | WO2013113008 | 8/2013 |
| WO | WO2013/148117 | 10/2013 |
| WO | WO2013148117 | 10/2013 |
| WO | WO2014/000042 | 1/2014 |
| WO | WO2014000042 | 1/2014 |
| WO | WO2014/100689 | 6/2014 |
| WO | WO2014100689 | 6/2014 |
| WO | WO2015/017710 | 2/2015 |
| WO | WO2015017710 | 2/2015 |

OTHER PUBLICATIONS

Bauskin et al. (2005) The Propeptide Mediates Formation of Stromal Stores of Promic-1: "Role in Determining Prostate Cancer Outcome", *Cancer Research*, 65(6), 2330-2336.

Bootcov et al. (1997) "MIC-1, a novel macrophage inhibitory cytokine, is a divergent member of the TGF-beta superfamily" *Proc. Natl. Acad. Sci. USA*, 94:11514-11519.

Breit et al. (2011) "The TGF-beta superfamily cytokine, MIC-1/GDF15: a pleotrophic cytokine with roles in inflammation, cancer and metabolism" *Growth Factors*, 29(5):187-95.

Chen et al. (1994) "Substitution of asparagine residues in Aspergillus awamori glucoamylase by site-directed mutagenesis to eliminate N-glycosylation and inactivation by deamidation" *Biochem J.*, 301: 275-81.

Clee et al. (2007) "The Genetic Landscape of Type 2 Diabetes in Mice", *Endocrine Reviews* 28(1): 48-83.

Dostalova et al. (2009) "Increased serum concentrations of macrophage inhibitory cytokine-1 in patients with obesity and type 2 diabetes mellitus: the influence of very low calorie diet", *Eur. J. Endocrinol.*, 161:397-404.

Ehses et al. (2007), "Increased Number of Islet-Associated Macrophages in Type 2 Diabetes", *Diabetes*, 56:2356-2370.

Fairlie et al. (2000) "Expression of a TGF-β superfamily protein, macrophage inhibitory cytokine-1, in the yeast *Pichia pastoris*" *Gene* 254:67-76.

(56) References Cited

OTHER PUBLICATIONS

Fairlie et al. (2001) "Epitope Mapping of the Transforming Growth Factor-b Superfamily Protein, Macrophage Inhibitory Cytokine-1 (MIC-1): Identification of at Least Five Distinct Epitope Specificities" *Biochem* 40:65-73.
Friedman et al. (1991) "Degradation of growth hormone releasing factor analogs in neutral aqueous solution is related to deamidation of asparagine residues" *Int. J. Peptide Protein Res.*, 37:14-20.
Hamann et al. (1996) "Regulation of energy balance by leptin" *Exp Endocrinol Diabetes* 104:293-300.
Hromas et al. (1997) "PLAB, a novel placental bone morphogenetic protein" *Biochim. Biophys. Acta*, 1354:40-4.
Johnen et al. (2007) "Tumor-induced anorexia and weight loss are mediated by the TGF-b superfamily cytokine MIC-1", *Nature Medicine*, 13 (11): 1333-1340.
Lajer et al. (2010) "Plasma growth differentiation factor-15 independently predicts all-cause and cardiovascular mortality as well as deterioration of kidney function in type 1 diabetic patients with nephropathy", *Diabetes Care*, 33(7),1567-1572.
Lind et al. (2009), "Growth-differentiation factor-15 is an independent marker of cardiovascular dysfunction and disease in the elderly: results from the Prospective Investigation of the Vasculature in Uppsala Seniors (PIVUS) Study", *European Heart Journal*. 30(19),2346-2353.
Macia et al. (2012) "Macrophage Inhibitory Cytokine 1 (MIC-1/GDF15) Decreases Food Intake, Body Weight and Improves Glucose Tolerance in Mice on Normal & Obesogenic Diets", *PLoS One*, 7(4):1-8.
Ngo et al. (1994), "Computational Complexity, Protein Structure Prediction, and Levinthal Paradox", *The Protein Folding Problem and Tertiary Structure Prediction*, Birkhauser, Boston, 492-495.
Paralkar et al. (1998) "Cloning and characterization of a novel member of the transforming growth factor[beta]/bone morphogenetic protein family" *J. Biol. Chem*, 273:13760-13767.
Robinson et al. (2004) "Prediction of primary structure deamidation rates of asparaginyl and glutaminyl peptides through steric and catalytic effects" *J. Pepide Res.*, 63:437-448.
Soler et al. (2012) "New Experimental Models of Diabetic Nephropathy in Mice Models of Type2 Diabetes: Efforts to Replicate Human Nephropathy" *Experimental Diabetes Research*, vol. 2012, Art. Id 616313.
Tokuriki et al. (2009), "Stability effects of mutations and protein evolvability", *Curr. Opin. Struc. Biol.*,19:596-604.
Vila et al. (2011), "The Relationship between Insulin Resistance and the Cardiovascular Biomarker Growth Differentiation Factor-15 in Obese Patients", *Clinical Chemistry*, 57(2):309-316.
Wells (1990), "Additivity of Mutational Effects in Proteins", *Biochemistry*, 29(37):8509-8517.
Yokoyama-Kobayashi et al. (1997) "Human cDNA encoding a novel TGF-beta superfamily protein highly expressed in placenta" *J. Biochem*, 122:622-626.
Bauskin et al. (2000) "The Propeptide of Macrophage Inhibitory Cytokine (MIC-1) a TGF-b Superfamily Member Acts as a Quality Control Determinant for Correctly Folded MIC-1" *EMBO J* 19:2212-2220.
Bauskin et al. (2005) The Propeptide Mediates Formation of Stromal Stores of PROMIC-1: "Role in Determining Prostate Cancer Outcome" *Cancer Research* 65(6):2330-2336.
Bootcov et al. (1997) "MIC-1 a novel macrophage inhibitory cytokine is a divergent member of the TGF-beta superfamily" *Proc. Natl. Acad. Sci. USA* 94:11514-11519.
Breit et al. (2011) "The TGF-beta superfamily cytokine MIC-1GDF15: a pleotrophic cytokine with roles in inflammation cancer and metabolism" *Growth Factors* 29(5):187-195.
Chen et al. (1994) "Substitution of asparagine residues in Aspergillus awamori glucoamylase by site-directed mutagenesis to eliminate N-glycosylation and inactivation by deamidation" *Biochem J.* 301: 275-81.
Clee et al. (2007) "The Genetic Landscape of Type 2 Diabetes in Mice" *Endocrine Reviews* 28(1): 48-83.
Dostalova et al. (2009) "Increased serum concentrations of macrophage inhibitory cytokine-1 in patients with obesity and type 2 diabetes mellitus: the influence of very low calorie diet" *Eur. J. Endocrinol.* 161:397-404.
Ehses et al. (2007) "Increased Number of Islet-Associated Macrophages in Type 2 Diabetes" *Diabetes* 56:2356-2370.
Fairlie et al. (2000) "Expression of a TGF-β superfamily protein macrophage inhibitory cytokine-1 in the yeast *Pichia pastoris*" *Gene* 254:67-76.
Fairlie et al. (2001) "Epitope Mapping of the Transforming Growth Factor-b Superfamily Protein Macrophage Inhibitory Cytokine-1 (MIC-1): Identification of at Least Five Distinct Epitope Specificities" *Biochem* 40:65-73.
Friedman et al. (1991) "Degradation of growth hormone releasing factor analogs in neutral aqueous solution is related to deamidation of asparagine residues" *Int. J. Peptide Protein Res.* 37:14-20.
Hromas et al. (1997) "PLAB a novel placental bone morphogenetic protein" *Biochim. Biophys. Acta* 1354:40-4.
Johnen et al. (2007) "Tumor-induced anorexia and weight loss are mediated by the TGF-b superfamily cytokine MIC-1" *Nature Medicine* 13 (11): 1333-1340.
Lajer et al. (2010) "Plasma growth differentiation factor-15 independently predicts all-cause and cardiovascular mortality as well as deterioration of kidney function in type 1 diabetic patients with nephropathy" *Diabetes Care* 33(7)1567-1572.
Lind et al. (2009) "Growth-differentiation factor-15 is an independent marker of cardiovascular dysfunction and disease in the elderly: results from the Prospective Investigation of the Vasculature in Uppsala Seniors (PIVUS) Study" *European Heart Journal* 30(19) 2346-2353.
Liu Yan et al. (2009) "Enhancing the Secretion of Recombinant Proteins by Engineering N -Glycosylation Sites" Biotechnol. Prog. 25(5):1468-1475.
Macia et al. (2012) "Macrophage Inhibitory Cytokine 1 (MIC-1GDF15) Decreases Food Intake Body Weight and Improves Glucose Tolerance in Mice on Normal & Obesogenic Diets" *PLoS One* 7(4):1-8.
Ngo et al. (1994) "Computational Complexity Protein Structure Prediction and Levinthal Paradox" *The Protein Folding Problem and Tertiary Structure Prediction* Birkhauser Boston 492-495.
Paralkar et al. (1998) "Cloning and characterization of a novel member of the transforming growth factor[beta]bone morphogenetic protein family" *J. Biol. Chem* 273:13760-13767.
Robinson et al. (2004) "Prediction of primary structure deamidation rates of asparaginyl and glutaminyl peptides through steric and catalytic effects" *J. Pepide Res.* 63:437-448.
Soler et al. (2012) "New Experimental Models of Diabetic Nephropathy in Mice Models of Type2 Diabetes: Efforts to Replicate Human Nephropathy" *Experimental Diabetes Research* vol. 2012 Art. ID 616313.
Tokuriki et al. (2009) "Stability effects of mutations and protein evolvability" *Curr. Opin. Struc. Biol.*19:596-604.
Vila et al. (2011) "The Relationship between Insulin Resistance and the Cardiovascular Biomarker Growth Differentiation Factor-15 in Obese Patients" *Clinical Chemistry* 57(2):309-316.
Wells (1990) "Additivity of Mutational Effects in Proteins" *Biochemistry* 29(37):8509-8517.
Yokoyama-Kobayashi et al. (1997) "Human cDNA encoding a novel TGF-beta superfamily protein highly expressed in placenta" *J. Biochem* 122:622-626.
Lingvay, Ildiko, et al., (2016) "Effect of Insulin Glargine Uptitration vs Insulin Degludec/Liraglutide on Glycated Hemoglobin Levels in Patients with Uncontrolled Type 2 Diabetes", JAMA, 315(9):898-907.
"Glucose metabolism disroders" http://ctdbase.org/detail.go?type=disease&acc=MESH%3AD044882, Mar. 25, 2016, 1 page.
Fairlie, W D et al, (2001) "The Propeptide of the Transforming Growth Factor-[beta] Superfamily Member, Macrophage Inhibitory Cytokine-1 (MIC-1), Is a Multifunctional Domain That Can Facilitate Protein Folding and Secretion", Priority Journal of Biological Chemistry May 18, 2001 American Society for Biochemistry and Molecular Biology Inc., 276(20):16911-16918.

(56) References Cited

OTHER PUBLICATIONS

Bottner et al. (1999) "Characterization of the rat, mouse, and human genes of growth/differentiation factor-15/macrophage inhibiting cytokine-1 (GDF-15/MIC-1)," Gene 237:105-111.
Oliveira Neto et al. (2008) "Interleukin-22 Forms Dimers that are Recognized by Two Interleukin-22R1 Receptor chains" Biophysical Journal, 94:1754-1765.
Welsh et al (2003) "Large-scale delineation of secreted protein biomarkers overexpressed in cancer tissue and serum," PNAS 100(6):3410-3415.

* cited by examiner

Figure 1

Glycosylation mutants (numbered 1-17; SEQ ID NOs: 2-18) aligned with wild type GDF15 (SEQ ID NO: 1)

```
            1         10        20        30        40        50
            :         |         |         |         |         |
WT          ARNGDHCPLGPGRCCRLHTVRASLEDLGWADWVLSPREVQVTMCIGACPSQFRAANMHAQ 60
1           ARNGTHCPLGPGRCCRLHTVNASLEDLGWADWVLSPREVQVTMCIGACPSQFRAANMHAQ 60
2           ARNGDHCPLGPGRCCNLTTVRASLEDLGWADWVLSPREVQVTMCIGACPSQFRAANMHAQ 60
3           ARNGDHCPLGPGRCCRLHTVRANLTDLGWADWVLSPREVQVTMCIGACPSQFRAANMHAQ 60
4           ARNGDHCPLGPGRCCRLHTVRASNETLGWADWVLSPREVQVTMCIGACPSQFRAANMHAQ 60
5           ARNGDHCPLGPGRCCRLHTVRASLEDLGWADWVLSPREVQVTMCIGACPNQTRAANMHAQ 60
6           ARNGDHCPLGPGRCCRLHTVRASLEDLGWADWVLSPREVQVTMCIGACPSNFTAANMHAQ 60
7           ARNGDHCPLGPGRCCRLHTVRASLEDLGWADWVLSPREVQVTMCIGACPSQNRTANMHAQ 60
8           ARNGDHCPLGPGRCCRLHTVRASLEDLGWADWVLSPREVQVTMCIGACPSQFNATNMHAQ 60
9           ARNGDHCPLGPGRCCRLHTVRASLEDLGWADWVLSPREVQVTMCIGACPSQFRAANMHAQ 60
10          ARNGDHCPLGPGRCCRLHTVRASLEDLGWADWVLSPREVQVTMCIGACPSQFRAANMHAQ 60
11          ARNGDHCPLGPGRCCRLHTVRASLEDLGWADWVLSPREVQVTMCIGACPSQFRAANMHAQ 60
12          ARNGDHCPLGPGRCCRLHTVRASLEDLGWADWVLSPREVQVTMCIGACPSQFRAANMHAQ 60
13          ARNGDHCPLGPGRCCRLHTVRASLEDLGWADWVLSPREVQVTMCIGACPSQFRAANMHAQ 60
14          ARNGDHCPLGPGRCCRLHTVRASLEDLGWADWVLSPREVQVTMCIGACPSQFRAANMHAQ 60
15          ARNGDHCPLGPGRCCRLHTVRASLEDLGWADWVLSPREVQVTMCIGACPSQFRAANMHAQ 60
16          ARNGDHCPLGPGRCCRLHTVRASLEDLGWADWVLSPREVQVTMCIGACPSQFRAANMHAQ 60
17          ARNGDHCPLGPGRCCRLHTVRASLEDLGWADWVLSPREVQVTMCIGACPSQFRAANMHAQ 60

61        70        80        90        100       110
            |         |         |         |         |         |
WT          IKTSLHRLKPDTVPAPCCVPASYNPMVLIQKTDTGVSLQTYDDLLAKDCHCI (SEQ ID NO:1)
1           IKTSLHRLKPDTVPAPCCVPASYNPMVLIQKTDTGVSLQTYDDLLAKDCHCI (SEQ ID NO:2)
2           IKTSLHRLKPDTVPAPCCVPASYNPMVLIQKTDTGVSLQTYDDLLAKDCHCI (SEQ ID NO:3)
3           IKTSLHRLKPDTVPAPCCVPASYNPMVLIQKTDTGVSLQTYDDLLAKDCHCI (SEQ ID NO:4)
4           IKTSLHRLKPDTVPAPCCVPASYNPMVLIQKTDTGVSLQTYDDLLAKDCHCI (SEQ ID NO:5)
5           IKTSLHRLKPDTVPAPCCVPASYNPMVLIQKTDTGVSLQTYDDLLAKDCHCI (SEQ ID NO:6)
6           IKTSLHRLKPDTVPAPCCVPASYNPMVLIQKTDTGVSLQTYDDLLAKDCHCI (SEQ ID NO:7)
7           IKTSLHRLKPDTVPAPCCVPASYNPMVLIQKTDTGVSLQTYDDLLAKDCHCI (SEQ ID NO:8)
8           IKTSLHRLKPDTVPAPCCVPASYNPMVLIQKTDTGVSLQTYDDLLAKDCHCI (SEQ ID NO:9)
9           IKTNLTRLKPDTVPAPCCVPASYNPMVLIQKTDTGVSLQTYDDLLAKDCHCI (SEQ ID NO:10)
10          IKTSNHTLKPDTVPAPCCVPASYNPMVLIQKTDTGVSLQTYDDLLAKDCHCI (SEQ ID NO:11)
11          IKTSLHRLKPDTVPAPCCVPANYTPMVLIQKTDTGVSLQTYDDLLAKDCHCI (SEQ ID NO:12)
12          IKTSLHRLKPDTVPAPCCVPASYNPMVLIQNTTGVSLQTYDDLLAKDCHCI (SEQ ID NO:13)
13          IKTSLHRLKPDTVPAPCCVPASYNPMVLIQKTNTVSLQTYDDLLAKDCHCI (SEQ ID NO:14)
14          IKTSLHRLKPDTVPAPCCVPASYNPMVLIQKTDNGTSLQTYDDLLAKDCHCI (SEQ ID NO:15)
15          IKTSLHRLKPDTVPAPCCVPASYNPMVLIQKTDTGNSTQTYDDLLAKDCHCI (SEQ ID NO:16)
16          IKTSLHRLKPDTVPAPCCVPASYNPMVLIQKTDTGVNLTTYDDLLAKDCHCI (SEQ ID NO:17)
17          IKTSLHRLKPDTVPAPCCVPASYNPMVLIQKTDTGVSLQTYDDLLNKTCHCI (SEQ ID NO:18)
```

Figure 2

Glycosylation ΔN3 mutants (numbered 18-34; SEQ ID NOs: 19-35) aligned with wild type GDF15 (SEQ ID NO: 1)

```
            1         10        20        30        40        50
            |         |         |         |         |         |
WT          ARNGDHCPLGPGRCCRLHTVRASLEDLGWADWVLSPREVQVTMCIGACPSQFRAANMHAQ 60
18             GTHCPLGPGRCCRLHTVNASLEDLGWADWVLSPREVQVTMCIGACPSQFRAANMHAQ 60
19             GDHCPLGPGRCCNLTTVRASLEDLGWADWVLSPREVQVTMCIGACPSQFRAANMHAQ 60
20             GDHCPLGPGRCCRLHTVRANLTDLGWADWVLSPREVQVTMCIGACPSQFRAANMHAQ 60
21             GDHCPLGPGRCCRLHTVRASNETLGWADWVLSPREVQVTMCIGACPSQFRAANMHAQ 60
22             GDHCPLGPGRCCRLHTVRASLEDLGWADWVLSPREVQVTMCIGACPNQTRAANMHAQ 60
23             GDHCPLGPGRCCRLHTVRASLEDLGWADWVLSPREVQVTMCIGACPSNFTAANMHAQ 60
24             GDHCPLGPGRCCRLHTVRASLEDLGWADWVLSPREVQVTMCIGACPSQNRTANMHAQ 60
25             GDHCPLGPGRCCRLHTVRASLEDLGWADWVLSPREVQVTMCIGACPSQFNATNMHAQ 60
26             GDHCPLGPGRCCRLHTVRASLEDLGWADWVLSPREVQVTMCIGACPSQFRAANMHAQ 60
27             GDHCPLGPGRCCRLHTVRASLEDLGWADWVLSPREVQVTMCIGACPSQFRAANMHAQ 60
28             GDHCPLGPGRCCRLHTVRASLEDLGWADWVLSPREVQVTMCIGACPSQFRAANMHAQ 60
29             GDHCPLGPGRCCRLHTVRASLEDLGWADWVLSPREVQVTMCIGACPSQFRAANMHAQ 60
30             GDHCPLGPGRCCRLHTVRASLEDLGWADWVLSPREVQVTMCIGACPSQFRAANMHAQ 60
31             GDHCPLGPGRCCRLHTVRASLEDLGWADWVLSPREVQVTMCIGACPSQFRAANMHAQ 60
32             GDHCPLGPGRCCRLHTVRASLEDLGWADWVLSPREVQVTMCIGACPSQFRAANMHAQ 60
33             GDHCPLGPGRCCRLHTVRASLEDLGWADWVLSPREVQVTMCIGACPSQFRAANMHAQ 60
34             GDHCPLGPGRCCRLHTVRASLEDLGWADWVLSPREVQVTMCIGACPSQFRAANMHAQ 60

61        70        80        90        100       110
            |         |         |         |         |         |
WT          IKTSLHRLKPDTVPAPCCVPASYNPMVLIQKTDTGVSLQTYDDLLAKDCHCI (SEQ ID NO:1)
18          IKTSLHRLKPDTVPAPCCVPASYNPMVLIQKTDTGVSLQTYDDLLAKDCHCI (SEQ ID NO:19)
19          IKTSLHRLKPDTVPAPCCVPASYNPMVLIQKTDTGVSLQTYDDLLAKDCHCI (SEQ ID NO:20)
20          IKTSLHRLKPDTVPAPCCVPASYNPMVLIQKTDTGVSLQTYDDLLAKDCHCI (SEQ ID NO:21)
21          IKTSLHRLKPDTVPAPCCVPASYNPMVLIQKTDTGVSLQTYDDLLAKDCHCI (SEQ ID NO:22)
22          IKTSLHRLKPDTVPAPCCVPASYNPMVLIQKTDTGVSLQTYDDLLAKDCHCI (SEQ ID NO:23)
23          IKTSLHRLKPDTVPAPCCVPASYNPMVLIQKTDTGVSLQTYDDLLAKDCHCI (SEQ ID NO:24)
24          IKTSLHRLKPDTVPAPCCVPASYNPMVLIQKTDTGVSLQTYDDLLAKDCHCI (SEQ ID NO:25)
25          IKTSLHRLKPDTVPAPCCVPASYNPMVLIQKTDTGVSLQTYDDLLAKDCHCI (SEQ ID NO:26)
26          IKTNLTRLKPDTVPAPCCVPASYNPMVLIQKTDTGVSLQTYDDLLAKDCHCI (SEQ ID NO:27)
27          IKTSNHTLKPDTVPAPCCVPASYNPMVLIQKTDTGVSLQTYDDLLAKDCHCI (SEQ ID NO:28)
28          IKTSLHRLKPDTVPAPCCVPANYTPMVLIQKTDTGVSLQTYDDLLAKDCHCI (SEQ ID NO:29)
29          IKTSLHRLKPDTVPAPCCVPASYNPMVLIQNTTGVSLQTYDDLLAKDCHCI (SEQ ID NO:30)
30          IKTSLHRLKPDTVPAPCCVPASYNPMVLIQKTNTTVSLQTYDDLLAKDCHCI (SEQ ID NO:31)
31          IKTSLHRLKPDTVPAPCCVPASYNPMVLIQKTDNGTSLQTYDDLLAKDCHCI (SEQ ID NO:32)
32          IKTSLHRLKPDTVPAPCCVPASYNPMVLIQKTDTGNSTQTYDDLLAKDCHCI (SEQ ID NO:33)
33          IKTSLHRLKPDTVPAPCCVPASYNPMVLIQKTDTGVNLTTYDDLLAKDCHCI (SEQ ID NO:34)
34          IKTSLHRLKPDTVPAPCCVPASYNPMVLIQKTDTGVSLQTYDDLLNKTCHCI (SEQ ID NO:35)
```

Figure 3

M1 Fusion Protein: IgK Signal Sequence (lowercase) fused to HSA Amino Acid Sequence Fused with a [(Gly4-Ser)]3 linker (Underlined) to the N-Terminus of Mature Human GDF15 (Bolded) (SEQ ID NO: 77)

mdmrvpaqllglllwlrgarcDAHKSEVAHRFKDLGEENFKALVLIAFAQYLQQCPFEDHVKLVNEVTEFAKTCVA
DESAENCDKSLHTLFGDKLCTVATLRETYGEMADCCAKQEPERNECFLQHKDDNPNLPRLVRPEVDVMCTAFHDNEE
TFLKKYLYEIARRHPYFYAPELLFFAKRYKAAFTECCQAADKAACLLPKLDELRDEGKASSAKQRLKCASLQKFGER
AFKAWAVARLSQRFPKAEFAEVSKLVTDLTKVHTECCHGDLLECADDRADLAKYICENQDSISSKLKECCEKPLLEK
SHCIAEVENDEMPADLPSLAADFVESKDVCKNYAEAKDVFLGMFLYEYARRHPDYSVVLLLRLAKTYETTLEKCCAA
ADPHECYAKVFDEFKPLVEEPQNLIKQNCELFEQLGEYKFQNALLVRYTKKVPQVSTPTLVEVSRNLGKVGSKCCKH
PEAKRMPCAEDYLSVVLNQLCVLHEKTPVSDRVTKCCTESLVNRRPCFSALEVDETYVPKEFNAETFTFHADICTLS
EKERQIKKQTALVELVKHKPKATKEQLKAVMDDFAAFVEKCCKADDKETCFAEEGKKLVAASQAALGL<u>GGGGSGGGG
SGGGGS</u>**ARNGDHCPLGPGRCCRLHTVRASLEDLGWADWVLSPREVQVTMCIGACPSQFRAANMHAQIKTSLHRLKPD
TVPAPCCVPASYNPMVLIQKTDTGVSLQTYDDLLAKDCHCI**

M2 Fusion Protein: IgK Signal Sequence (lowercase) fused to HSA Amino Acid Sequence Fused with a [(Gly4-Ser)]3 linker (Underlined) to the N-Terminus of Mature Human GDF15 (Bolded) containing a 3-amino acid (ΔARN) deletion (SEQ ID NO: 78)

mdmrvpaqllglllwlrgarcDAHKSEVAHRFKDLGEENFKALVLIAFAQYLQQCPFEDHVKLVNEVTEFAKTCVA
DESAENCDKSLHTLFGDKLCTVATLRETYGEMADCCAKQEPERNECFLQHKDDNPNLPRLVRPEVDVMCTAFHDNEE
TFLKKYLYEIARRHPYFYAPELLFFAKRYKAAFTECCQAADKAACLLPKLDELRDEGKASSAKQRLKCASLQKFGER
AFKAWAVARLSQRFPKAEFAEVSKLVTDLTKVHTECCHGDLLECADDRADLAKYICENQDSISSKLKECCEKPLLEK
SHCIAEVENDEMPADLPSLAADFVESKDVCKNYAEAKDVFLGMFLYEYARRHPDYSVVLLLRLAKTYETTLEKCCAA
ADPHECYAKVFDEFKPLVEEPQNLIKQNCELFEQLGEYKFQNALLVRYTKKVPQVSTPTLVEVSRNLGKVGSKCCKH
PEAKRMPCAEDYLSVVLNQLCVLHEKTPVSDRVTKCCTESLVNRRPCFSALEVDETYVPKEFNAETFTFHADICTLS
EKERQIKKQTALVELVKHKPKATKEQLKAVMDDFAAFVEKCCKADDKETCFAEEGKKLVAASQAALGL<u>GGGGSGGGG
SGGGGS</u>**GDHCPLGPGRCCRLHTVRASLEDLGWADWVLSPREVQVTMCIGACPSQFRAANMHAQIKTSLHRLKPDTVP
APCCVPASYNPMVLIQKTDTGVSLQTYDDLLAKDCHCI**

Figure 5

M3 Fusion Protein: IgK Signal Sequence (lowercase) fused to HSA Amino Acid Sequence Fused with a [(Gly$_4$-Ser)]$_5$ linker (Underlined) to the N-Terminus of Mature Human GDF15 (Bolded) Amino Acid Sequence containing a 3-amino acid deletion (denoted ΔARN or ΔN3) (SEQ ID NO: 79)

mdmrvpaqllglllwlrgarcDAHKSEVAHRFKDLGEENFKALVLIAFAQYLQQCPFEDHVKLVNEVTEFAKTCVA
DESAENCDKSLHTLFGDKLCTVATLRETYGEMADCCAKQEPERNECFLQHKDDNPNLPRLVRPEVDVMCTAFHDNEE
TFLKKYLYEIARRHPYFYAPELLFFAKRYKAAFTECCQAADKAACLLPKLDELRDEGKASSAKQRLKCASLQKFGER
AFKAWAVARLSQRFPKAEFAEVSKLVTDLTKVHTECCHGDLLECADDRADLAKYICENQDSISSKLKECCEKPLLEK
SHCIAEVENDEMPADLPSLAADFVESKDVCKNYAEAKDVFLGMFLYEYARRHPDYSVVLLLRLAKTYETTLEKCCAA
ADPHECYAKVFDEFKPLVEEPQNLIKQNCELFEQLGEYKFQNALLVRYTKKVPQVSTPTLVEVSRNLGKVGSKCCKH
PEAKRMPCAEDYLSVVLNQLCVLHEKTPVSDRVTKCCTESLVNRRPCFSALEVDETYVPKEFNAETFTFHADICTLS
EKERQIKKQTALVELVKHKPKATKEQLKAVMDDFAAFVEKCCKADDKETCFAEEGKKLVAASQAALGL<u>GGGGSGGGG
SGGGGSGGGGSGGGGS</u>**GDHCPLGPGRCCRLHTVRASLEDLGWADWVLSPREVQVTMCIGACPSQFRAANMHAQIKTS
LHRLKPDTVPAPCCVPASYNPMVLIQKTDTGVSLQTYDDLLAKDCHCI**

M4 - Fusion Protein: IgK Signal Sequence (lowercase) fused to HSA Amino Acid Sequence Fused with a [(Gly$_4$-Ser)]$_5$ linker (Underlined) to the N-Terminus of Mature Human GDF15 (Bolded) Amino Acid Sequence containing a 6-amino acid deletion (denoted as ΔARNGDH or ΔN6) (SEQ ID NO: 80)

mdmrvpaqllglllwlrgarcDAHKSEVAHRFKDLGEENFKALVLIAFAQYLQQCPFEDHVKLVNEVTEFAKTCVA
DESAENCDKSLHTLFGDKLCTVATLRETYGEMADCCAKQEPERNECFLQHKDDNPNLPRLVRPEVDVMCTAFHDNEE
TFLKKYLYEIARRHPYFYAPELLFFAKRYKAAFTECCQAADKAACLLPKLDELRDEGKASSAKQRLKCASLQKFGER
AFKAWAVARLSQRFPKAEFAEVSKLVTDLTKVHTECCHGDLLECADDRADLAKYICENQDSISSKLKECCEKPLLEK
SHCIAEVENDEMPADLPSLAADFVESKDVCKNYAEAKDVFLGMFLYEYARRHPDYSVVLLLRLAKTYETTLEKCCAA
ADPHECYAKVFDEFKPLVEEPQNLIKQNCELFEQLGEYKFQNALLVRYTKKVPQVSTPTLVEVSRNLGKVGSKCCKH
PEAKRMPCAEDYLSVVLNQLCVLHEKTPVSDRVTKCCTESLVNRRPCFSALEVDETYVPKEFNAETFTFHADICTLS
EKERQIKKQTALVELVKHKPKATKEQLKAVMDDFAAFVEKCCKADDKETCFAEEGKKLVAASQAALGL<u>GGGGSGGGG
SGGGGSGGGGSGGGGS</u>**CPLGPGRCCRLHTVRASLEDLGWADWVLSPREVQVTMCIGACPSQFRAANMHAQIKTSLHR
LKPDTVPAPCCVPASYNPMVLIQKTDTGVSLQTYDDLLAKDCHCI**

Figure 8A hGDF15 Glycosylation muteins comprising an IgK Signal Sequence (lowercase) fused to the N-Terminus of Mature Human GDF15 (Bolded) Amino Acid Sequence M5 - (SEQ ID NO: 81)
mdmrvpaqllglllwlrgarc**ARNGTHCPLGPGRCCRLHTVNASLEDLGWADWVLSPREVQVTMCIGAC
PSQFRAANMHAQIKTSLHRLKPDTVPAPCCVPASYNPMVLIQKTDTGVSLQTYDDLLAKDCHCI**

M6 - (SEQ ID NO: 82)
mdmrvpaqllglllwlrgarc**ARNGDHCPLGPGRCCNLTTVRASLEDLGWADWVLSPREVQVTMCIGAC
PSQFRAANMHAQIKTSLHRLKPDTVPAPCCVPASYNPMVLIQKTDTGVSLQTYDDLLAKDCHCI**

M7 - (SEQ ID NO: 83)
mdmrvpaqllglllwlrgarc**ARNGDHCPLGPGRCCRLHTVRANLTDLGWADWVLSPREVQVTMCIGAC
PSQFRAANMHAQIKTSLHRLKPDTVPAPCCVPASYNPMVLIQKTDTGVSLQTYDDLLAKDCHCI**

M8 - (SEQ ID NO: 84)
mdmrvpaqllglllwlrgarc**ARNGDHCPLGPGRCCRLHTVRASNETLGWADWVLSPREVQVTMCIGAC
PSQFRAANMHAQIKTSLHRLKPDTVPAPCCVPASYNPMVLIQKTDTGVSLQTYDDLLAKDCHCI**

M9 - (SEQ ID NO: 85)
mdmrvpaqllglllwlrgarc**ARNGDHCPLGPGRCCRLHTVRASLEDLGWADWVLSPREVQVTMCIGAC
PNQTRAANMHAQIKTSLHRLKPDTVPAPCCVPASYNPMVLIQKTDTGVSLQTYDDLLAKDCHCI**

M10 - (SEQ ID NO: 86)
mdmrvpaqllglllwlrgarc**ARNGDHCPLGPGRCCRLHTVRASLEDLGWADWVLSPREVQVTMCIGAC
PSNFTAANMHAQIKTSLHRLKPDTVPAPCCVPASYNPMVLIQKTDTGVSLQTYDDLLAKDCHCI**

M11 - (SEQ ID NO: 87)
mdmrvpaqllglllwlrgarc**ARNGDHCPLGPGRCCRLHTVRASLEDLGWADWVLSPREVQVTMCIGAC
PSQNRTANMHAQIKTSLHRLKPDTVPAPCCVPASYNPMVLIQKTDTGVSLQTYDDLLAKDCHCI**

M12 - (SEQ ID NO: 88)
mdmrvpaqllglllwlrgarc**ARNGDHCPLGPGRCCRLHTVRASLEDLGWADWVLSPREVQVTMCIGAC
PSQFNATNMHAQIKTSLHRLKPDTVPAPCCVPASYNPMVLIQKTDTGVSLQTYDDLLAKDCHCI**

M13 - (SEQ ID NO: 89)
mdmrvpaqllglllwlrgarc**ARNGDHCPLGPGRCCRLHTVRASLEDLGWADWVLSPREVQVTMCIGAC
PSQFRAANMHAQIKTNLTRLKPDTVPAPCCVPASYNPMVLIQKTDTGVSLQTYDDLLAKDCHCI**

M14 - (SEQ ID NO: 90)
mdmrvpaqllglllwlrgarc**ARNGDHCPLGPGRCCRLHTVRASLEDLGWADWVLSPREVQVTMCIGAC
PSQFRAANMHAQIKTSNHTLKPDTVPAPCCVPASYNPMVLIQKTDTGVSLQTYDDLLAKDCHCI**

Figure 8A (continued)

M15 - (SEQ ID NO: 91)
mdmrvpaqllglllllwlrgarcARNGDHCPLGPGRCCRLHTVRASLEDLGWADWVLSPREVQVTMCIGAC
PSQFRAANMHAQIKTSLHRLKPDTVPAPCCVPANYTPMVLIQKTDTGVSLQTYDDLLAKDCHCI M16 - (SEQ ID NO: 92)
mdmrvpaqllglllllwlrgarcARNGDHCPLGPGRCCRLHTVRASLEDLGWADWVLSPREVQVTMCIGAC
PSQFRAANMHAQIKTSLHRLKPDTVPAPCCVPASYNPMVLIQNTTTGVSLQTYDDLLAKDCHCI M17 - (SEQ ID NO: 93)
mdmrvpaqllglllllwlrgarcARNGDHCPLGPGRCCRLHTVRASLEDLGWADWVLSPREVQVTMCIGAC
PSQFRAANMHAQIKTSLHRLKPDTVPAPCCVPASYNPMVLIQKTNTTVSLQTYDDLLAKDCHCI M18 - (SEQ ID NO: 94)
mdmrvpaqllglllllwlrgarcARNGDHCPLGPGRCCRLHTVRASLEDLGWADWVLSPREVQVTMCIGAC
PSQFRAANMHAQIKTSLHRLKPDTVPAPCCVPASYNPMVLIQKTDNGTSLQTYDDLLAKDCHCI M19 - (SEQ ID NO: 95)
mdmrvpaqllglllllwlrgarcARNGDHCPLGPGRCCRLHTVRASLEDLGWADWVLSPREVQVTMCIGAC
PSQFRAANMHAQIKTSLHRLKPDTVPAPCCVPASYNPMVLIQKTDTGNSTQTYDDLLAKDCHCI M20 - (SEQ ID NO: 96)
mdmrvpaqllglllllwlrgarcARNGDHCPLGPGRCCRLHTVRASLEDLGWADWVLSPREVQVTMCIGAC
PSQFRAANMHAQIKTSLHRLKPDTVPAPCCVPASYNPMVLIQKTDTGVNLTTYDDLLAKDCHCI M21 - (SEQ ID NO: 97)
mdmrvpaqllglllllwlrgarcARNGDHCPLGPGRCCRLHTVRASLEDLGWADWVLSPREVQVTMCIGAC
PSQFRAANMHAQIKTSLHRLKPDTVPAPCCVPASYNPMVLIQKTDTGVSLQTYDDLLNKTCHCI

Figure 8B

Nucleic acid sequences encoding the hGDF15 Glycosylation muteins comprising an IgK Signal Sequence fused to the N-Terminus of Mature Human GDF15 Amino Acid Sequence (as shown in Figure 8A).

Nucleic acid sequences encoding M5 atggacatgagggtccccgctcagctcctggggctcctgctactctggctccgaggtgccagat
gtGCGCGCAACGGGACTCACTGTCCGCTCGGGCCCGGGCGTTGCTGCCGTCTGCACACGGTCAA
CGCGTCGCTGGAAGACCTGGGCTGGGCCGATTGGGTGCTGTCGCCACGGGAGGTGCAAGTGACC
ATGTGCATCGGCGCGTGCCCGAGCCAGTTCCGGGCGGCAAACATGCACGCGCAGATCAAGACGA
GCCTGCACCGCCTGAAGCCCGACACGGTGCCAGCGCCCTGCTGCGTGCCCGCCAGCTACAATCC
CATGGTGCTCATTCAAAAGACCGACACCGGGGTGTCGCTCCAGACCTATGATGACTTGTTAGCC
AAAGACTGCCACTGCATATGA (SEQ ID NO: 108)

Nucleic acid sequences encoding M6 atggacatgagggtccccgctcagctcctggggctcctgctactctggctccgaggtgccagat
gtGCGCGCAACGGGGACCACTGTCCGCTCGGGCCCGGGCGTTGCTGCAATCTGACCACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAGCCAGTTCCGGGCGGCAAACATGCACGCGCAGATCAAGACGA
GCCTGCACCGCCTGAAGCCCGACACGGTGCCAGCGCCCTGCTGCGTGCCCGCCAGCTACAATCC
CATGGTGCTCATTCAAAAGACCGACACCGGGGTGTCGCTCCAGACCTATGATGACTTGTTAGCC
AAAGACTGCCACTGCATATGA (SEQ ID NO: 109)

Nucleic acid sequences encoding M7 atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGAACCTGACGGACCTGGGCTGGGCCGATTGGGTGCTGTCGCCACGGGAGGTGCAAGTGACC
ATGTGCATCGGCGCGTGCCCGAGCCAGTTCCGGGCGGCAAACATGCACGCGCAGATCAAGACGA
GCCTGCACCGCCTGAAGCCCGACACGGTGCCAGCGCCCTGCTGCGTGCCCGCCAGCTACAATCC
CATGGTGCTCATTCAAAAGACCGACACCGGGGTGTCGCTCCAGACCTATGATGACTTGTTAGCC
AAAGACTGCCACTGCATATGA (SEQ ID NO: 110)

Figure 8B (continued)

Nucleic acid sequences encoding M8 atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGAATGAAACCCTGGGCTGGGCCGATTGGGTGCTGTCGCCACGGGAGGTGCAAGTGACC
ATGTGCATCGGCGCGTGCCCGAGCCAGTTCCGGGCGGCAAACATGCACGCGCAGATCAAGACGA
GCCTGCACCGCCTGAAGCCCGACACGGTGCCAGCGCCCTGCTGCGTGCCCGCCAGCTACAATCC
CATGGTGCTCATTCAAAAGACCGACACCGGGGTGTCGCTCCAGACCTATGATGACTTGTTAGCC
AAAGACTGCCACTGCATATGA (SEQ ID NO: 111)

Nucleic acid sequences encoding M9 atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAACCAGACCCGGGCGGCAAACATGCACGCGCAGATCAAGACGA
GCCTGCACCGCCTGAAGCCCGACACGGTGCCAGCGCCCTGCTGCGTGCCCGCCAGCTACAATCC
CATGGTGCTCATTCAAAAGACCGACACCGGGGTGTCGCTCCAGACCTATGATGACTTGTTAGCC
AAAGACTGCCACTGCATATGA (SEQ ID NO: 112)

Nucleic acid sequences encoding M10 atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAGCAACTTCACGGCGGCAAACATGCACGCGCAGATCAAGACGA
GCCTGCACCGCCTGAAGCCCGACACGGTGCCAGCGCCCTGCTGCGTGCCCGCCAGCTACAATCC
CATGGTGCTCATTCAAAAGACCGACACCGGGGTGTCGCTCCAGACCTATGATGACTTGTTAGCC
AAAGACTGCCACTGCATATGA (SEQ ID NO: 113)

Nucleic acid sequences encoding M11 atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAGCCAGAACCGGACGGCAAACATGCACGCGCAGATCAAGACGA
GCCTGCACCGCCTGAAGCCCGACACGGTGCCAGCGCCCTGCTGCGTGCCCGCCAGCTACAATCC
CATGGTGCTCATTCAAAAGACCGACACCGGGGTGTCGCTCCAGACCTATGATGACTTGTTAGCC
AAAGACTGCCACTGCATATGA (SEQ ID NO: 114)

Figure 8B (continued)

Nucleic acid sequences encoding M12
atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAGCCAGTTCAACGCGACGAACATGCACGCGCAGATCAAGACGA
GCCTGCACCGCCTGAAGCCCGACACGGTGCCAGCGCCCTGCTGCGTGCCCGCCAGCTACAATCC
CATGGTGCTCATTCAAAAGACCGACACCGGGGTGTCGCTCCAGACCTATGATGACTTGTTAGCC
AAAGACTGCCACTGCATATGA (SEQ ID NO: 115)

Nucleic acid sequences encoding M13
atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAGCCAGTTCCGGGCGGCAAACATGCACGCGCAGATCAAGACGA
ACCTGACGCGCCTGAAGCCCGACACGGTGCCAGCGCCCTGCTGCGTGCCCGCCAGCTACAATCC
CATGGTGCTCATTCAAAAGACCGACACCGGGGTGTCGCTCCAGACCTATGATGACTTGTTAGCC
AAAGACTGCCACTGCATATGA (SEQ ID NO: 116)

Nucleic acid sequences encoding M14
atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAGCCAGTTCCGGGCGGCAAACATGCACGCGCAGATCAAGACGA
GCAACCACACCCTGAAGCCCGACACGGTGCCAGCGCCCTGCTGCGTGCCCGCCAGCTACAATCC
CATGGTGCTCATTCAAAAGACCGACACCGGGGTGTCGCTCCAGACCTATGATGACTTGTTAGCC
AAAGACTGCCACTGCATA (SEQ ID NO: 117)

Nucleic acid sequences encoding M15
atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAGCCAGTTCCGGGCGGCAAACATGCACGCGCAGATCAAGACGA
GCCTGCACCGCCTGAAGCCCGACACGGTGCCAGCGCCCTGCTGCGTGCCCGCCAACTACACTCC
CATGGTGCTCATTCAAAAGACCGACACCGGGGTGTCGCTCCAGACCTATGATGACTTGTTAGCC
AAAGACTGCCACTGCATATGA (SEQ ID NO: 118)

Figure 8B (continued)

Nucleic acid sequences encoding M16 atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAGCCAGTTCCGGGCGGCAAACATGCACGCGCAGATCAAGACGA
GCCTGCACCGCCTGAAGCCCGACACGGTGCCAGCGCCTGCTGCGTGCCCGCCAGCTACAATCC
CATGGTGCTCATTCAAAACACCACCACCGGGGTGTCGCTCCAGACCTATGATGACTTGTTAGCC
AAAGACTGCCACTGCATATGA (SEQ ID NO: 119)

Nucleic acid sequences encoding M17 atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAGCCAGTTCCGGGCGGCAAACATGCACGCGCAGATCAAGACGA
GCCTGCACCGCCTGAAGCCCGACACGGTGCCAGCGCCTGCTGCGTGCCCGCCAGCTACAATCC
CATGGTGCTCATTCAAAAGACCAACACCACGGTGTCGCTCCAGACCTATGATGACTTGTTAGCC
AAAGACTGCCACTGCATATGA (SEQ ID NO: 120)

Nucleic acid sequences encoding M18 atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAGCCAGTTCCGGGCGGCAAACATGCACGCGCAGATCAAGACGA
GCCTGCACCGCCTGAAGCCCGACACGGTGCCAGCGCCTGCTGCGTGCCCGCCAGCTACAATCC
CATGGTGCTCATTCAAAAGACCGACAACGGGACGTCGCTCCAGACCTATGATGACTTGTTAGCC
AAAGACTGCCACTGCATATGA (SEQ ID NO: 121)

Nucleic acid sequences encoding M19 atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAGCCAGTTCCGGGCGGCAAACATGCACGCGCAGATCAAGACGA
GCCTGCACCGCCTGAAGCCCGACACGGTGCCAGCGCCTGCTGCGTGCCCGCCAGCTACAATCC
CATGGTGCTCATTCAAAAGACCGACACCGGGAACTCGACCCAGACCTATGATGACTTGTTAGCC
AAAGACTGCCACTGCATATGA (SEQ ID NO: 122)

Figure 8B (continued)

Nucleic acid sequences encoding M20 atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAGCCAGTTCCGGGCGGCAAACATGCACGCGCAGATCAAGACGA
GCCTGCACCGCCTGAAGCCCGACACGGTGCCAGCGCCCTGCTGCGTGCCCGCCAGCTACAATCC
CATGGTGCTCATTCAAAAGACCGACACCGGGGTGAACCTCACGACCTATGATGACTTGTTAGCC
AAAGACTGCCACTGCATATGA (SEQ ID NO: 123)

Nucleic acid sequences encoding M21 atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCGCGCGTC
GCTGGAAGACCTGGGCTGGGCCGATTGGGTGCTGTCGCCACGGGAGGTGCAAGTGACCATGTGCATCGGC
GCGTGCCCGAGCCAGTTCCGGGCGGCAAACATGCACGCGCAGATCAAGACGAGCCTGCACCGCCTGAAGC
CCGACACGGTGCCAGCGCCCTGCTGCGTGCCCGCCAGCTACAATCCCATGGTGCTCATTCAAAAGACCGA
CACCGGGGTGTCGCTCCAGACCTATGATGACTTGTTAAACAAAACCTGCCACTGCATATGA (SEQ ID
NO: 124)

Figure 8C

ΔN3-M16 amino acid sequence (IgK Signal Sequence (lowercase) fused to the N-Terminus of Mature Human GDF15 (Bolded)

mdmrvpaqllglllllwlrgarcGDHCPLGPGRCCRLHTVRASLEDLGWADWVLSPREVQVTMCIGACPSQ FRAANMHAQIKTSLHRLKPDTVPAPCCVPASYNPMVLIQNTTTGVSLQTYDDLLAKDCHCI (SEQ ID NO: 100)

Nucleic acid sequence encoding ΔN3-M16 atggacatgagggtccccgctcagctcctggggctcctgctactctggctccgaggtgccagat
gtGGGGACCACTGTCCGCTCGGGCCCGGGCGTTGCTGCCGTCTGCACACGGTCCGCGCGTCGCT
GGAAGACCTGGGCTGGGCCGATTGGGTGCTGTCGCCACGGGAGGTGCAAGTGACCATGTGCATC
GGCGCGTGCCCGAGCCAGTTCCGGGCGGCAAACATGCACGCGCAGATCAAGACGAGCCTGCACC
GCCTGAAGCCCGACACGGTGCCAGCGCCTGCTGCGTGCCCGCCAGCTACAATCCCATGGTGCT
CATTCAAAACACCACCACCGGGGTGTCGCTCCAGACCTATGATGACTTGTTAGCCAAAGACTGC
CACTGCATATGA (SEQ ID NO: 125)

Figure 8D

Amino acid sequence of wild type mature human GDF15 fused to IgK signal sequence at the N-terminus (IgK-WT-GDF15)

mdmrvpaqllglllllwlrgarcARNGDHCPLGPGRCCRLHTVRASLEDLGWADWVLSPREVQVTMCIGAC PSQFRAANMHAQIKTSLHRLKPDTVPAPCCVPASYNPMVLIQKTDTGVSLQTYDDLLAKDCHCI (SEQ ID NO: 126)

Nucleic acid encoding IgK-WT-GDF15 atggacatgagggtccccgctcagctcctggggctcctgctactctggctccgaggtgccagat
gtGCGCGCAACGGGGACCACTGTCCGCTCGGGCCCGGGCGTTGCTGCCGTCTGCACACGGTCCG
CGCGTCGCTGGAAGACCTGGGCTGGGCCGATTGGGTGCTGTCGCCACGGGAGGTGCAAGTGACC
ATGTGCATCGGCGCGTGCCCGAGCCAGTTCCGGGCGGCAAACATGCACGCGCAGATCAAGACGA
GCCTGCACCGCCTGAAGCCCGACACGGTGCCAGCGCCTGCTGCGTGCCCGCCAGCTACAATCC
CATGGTGCTCATTCAAAAGACCGACACCGGGGTGTCGCTCCAGACCTATGATGACTTGTTAGCC
AAAGACTGCCACTGCATATGA (SEQ ID NO: 127)

Figure 9

Human GDF15 Mutein Dimer Formation, N-Glycan Site Occupancy and Solubility assessment

| Mutein ID | Dimer | N-Glyc | Solubility Inflection Point |
|---|---|---|---|
| hGDF15 | YES | - | ++ |
| M5 | YES | YES | ++++ |
| M6 | YES | YES | Not Performed |
| M7 | YES | YES | +++ |
| M8 | NO | NO | Not performed |
| M9 | YES | YES | Not performed |
| M10 | NO | NO | Not performed |
| M11 | YES | YES | +++ |
| M12 | YES | YES | +++ |
| M13 | YES | YES | ++++ |
| M14 | NO | NO | Not performed |
| M15 | NO | NO | Not performed |
| M16 | YES | YES | +++++ |
| ΔN3-M16 | YES | YES | +++++ |
| M17 | YES | YES | +++++ |
| M18 | YES | YES | Not performed |
| M19 | YES | YES | Not performed |
| M20 | YES | YES | ++++ |
| M21 | YES | YES | +++ |

SEQUENCE LISTING

```
<160> NUMBER OF SEQ ID NOS: 127

<210> SEQ ID NO 1
<211> LENGTH: 112
<212> TYPE: PRT
<213> ORGANISM: Homo sapiens

<400> SEQUENCE: 1

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 2
<211> LENGTH: 112
<212> TYPE: PRT
<213> ORGANISM: Artificial Sequence
<220> FEATURE:
<223> OTHER INFORMATION: synthetic polypeptide sequence

<400> SEQUENCE: 2

Ala Arg Asn Gly Thr His Cys Pro Leu Gly Pro Gly Arg Cys Cys Arg
```

```
1               5                   10                  15
Leu His Thr Val Asn Ala Ser Leu Glu Asp Leu Gly Trp Ala Asp Trp
            20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
            50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
                100                 105                 110
```

<210> SEQ ID NO 3
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 3

```
Ala Arg Asn Gly Asp His Cys Pro Leu Gly Pro Gly Arg Cys Cys Asn
1               5                   10                  15

Leu Thr Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
            50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
                100                 105                 110
```

<210> SEQ ID NO 4
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 4

```
Ala Arg Asn Gly Asp His Cys Pro Leu Gly Pro Gly Arg Cys Cys Arg
1               5                   10                  15

Leu His Thr Val Arg Ala Asn Leu Thr Asp Leu Gly Trp Ala Asp Trp
            20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
            50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95
```

```
Ser Leu Gln Thr Tyr Asp Asp Leu Leu Ala Lys Asp Cys His Cys Ile
            100                 105                 110
```

<210> SEQ ID NO 5
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 5

```
Ala Arg Asn Gly Asp His Cys Pro Leu Gly Pro Gly Arg Cys Cys Arg
1               5                   10                  15

Leu His Thr Val Arg Ala Ser Asn Glu Thr Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 6
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 6

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Asn Gln Thr Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 7
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 7

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
```

```
            20                  25                  30
Val Leu Ser Pro Arg Glu Val Gln Val Thr Met Cys Ile Gly Ala Cys
         35                  40                  45

Pro Ser Asn Phe Thr Ala Ala Asn Met His Ala Gln Ile Lys Thr Ser
     50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110

<210> SEQ ID NO 8
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 8

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
             20                  25                  30

Val Leu Ser Pro Arg Glu Val Gln Val Thr Met Cys Ile Gly Ala Cys
         35                  40                  45

Pro Ser Gln Asn Arg Thr Ala Asn Met His Ala Gln Ile Lys Thr Ser
     50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110

<210> SEQ ID NO 9
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 9

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
             20                  25                  30

Val Leu Ser Pro Arg Glu Val Gln Val Thr Met Cys Ile Gly Ala Cys
         35                  40                  45

Pro Ser Gln Phe Asn Ala Thr Asn Met His Ala Gln Ile Lys Thr Ser
     50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110
```

```
<210> SEQ ID NO 10
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 10

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Asn
    50                  55                  60

Leu Thr Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 11
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 11

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Asn His Thr Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 12
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 12

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
```

```
            35                  40                  45

Pro Ser Gln Phe Arg Ala Ala Asn Met His Ala Gln Ile Lys Thr Ser
         50                  55                  60

Leu His Arg Leu Lys Pro Asp Thr Val Pro Ala Pro Cys Cys Val Pro
 65                  70                  75                  80

Ala Asn Tyr Thr Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
                100                 105                 110

<210> SEQ ID NO 13
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 13

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
         50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Asn Thr Thr Gly Val
                 85                  90                  95

Ser Leu Gln Thr Tyr Asp Asp Leu Leu Ala Lys Asp Cys His Cys Ile
                100                 105                 110

<210> SEQ ID NO 14
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 14

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
         50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asn Thr Val
                 85                  90                  95

Ser Leu Gln Thr Tyr Asp Asp Leu Leu Ala Lys Asp Cys His Cys Ile
                100                 105                 110

<210> SEQ ID NO 15
<211> LENGTH: 112
```

-continued

```
<212> TYPE: PRT
<213> ORGANISM: Artificial sequence
<220> FEATURE:
<223> OTHER INFORMATION: synthetic polypeptide sequence

<400> SEQUENCE: 15

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Asn Gly Thr
                85                  90                  95

Ser Leu Gln Thr Tyr Asp Asp Leu Leu Ala Lys Asp Cys His Cys Ile
            100                 105                 110

<210> SEQ ID NO 16
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 16

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Asn
                85                  90                  95

Ser Thr Gln Thr Tyr Asp Asp Leu Leu Ala Lys Asp Cys His Cys Ile
            100                 105                 110

<210> SEQ ID NO 17
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 17

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
```

```
                 50                  55                  60
Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Asn Leu Thr Thr Tyr Asp Asp Leu Leu Ala Lys Asp Cys His Cys Ile
            100                 105                 110
```

<210> SEQ ID NO 18
<211> LENGTH: 112
<212> TYPE: PRT
<213> ORGANISM: Artificial sequence
<220> FEATURE:
<223> OTHER INFORMATION: synthetic polypeptide sequence

<400> SEQUENCE: 18

```
Ala Arg Asn Gly Asp His Cys Pro Leu Gly Pro Gly Arg Cys Cys Arg
  1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Asn Lys Thr Cys His Cys Ile
            100                 105                 110
```

<210> SEQ ID NO 19
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 19

```
Gly Thr His Cys Pro Leu Gly Pro Gly Arg Cys Cys Arg Leu His Thr
  1               5                  10                  15

Val Asn Ala Ser Leu Glu Asp Leu Gly Trp Ala Asp Trp Val Leu Ser
                 20                  25                  30

Pro Arg Glu Val Gln Val Thr Met Cys Ile Gly Ala Cys Pro Ser Gln
             35                  40                  45

Phe Arg Ala Ala Asn Met His Ala Gln Ile Lys Thr Ser Leu His Arg
 50                  55                  60

Leu Lys Pro Asp Thr Val Pro Ala Pro Cys Cys Val Pro Ala Ser Tyr
 65                  70                  75                  80

Asn Pro Met Val Leu Ile Gln Lys Thr Asp Thr Gly Val Ser Leu Gln
                 85                  90                  95

Thr Tyr Asp Asp Leu Leu Ala Lys Asp Cys His Cys Ile
            100                 105
```

<210> SEQ ID NO 20
<211> LENGTH: 109
<212> TYPE: PRT
<213> ORGANISM: Artificial sequence
<220> FEATURE:

<223> OTHER INFORMATION: synthetic polypeptide sequence

<400> SEQUENCE: 20

Gly Asp His Cys Pro Leu Gly Pro Gly Arg Cys Cys Asn Leu Thr Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 21
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 21

Gly Asp His Cys Pro Leu Gly Pro Gly Arg Cys Cys Arg Leu His Thr
1               5                   10                  15

Val Arg Ala Asn Leu Thr Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 22
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 22

Gly Asp His Cys Pro Leu Gly Pro Gly Arg Cys Cys Arg Leu His Thr
1               5                   10                  15

Val Arg Ala Ser Asn Glu Thr Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr

```
                65                  70                  75                  80
Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 23
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 23

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
                20                  25                  30

Pro Arg Glu Val Gln Val Thr Met Cys Ile Gly Ala Cys Pro Asn Gln
            35                  40                  45

Thr Arg Ala Ala Asn Met His Ala Gln Ile Lys Thr Ser Leu His Arg
        50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 24
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 24

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
                20                  25                  30

Pro Arg Glu Val Gln Val Thr Met Cys Ile Gly Ala Cys Pro Ser Asn
            35                  40                  45

Phe Thr Ala Ala Asn Met His Ala Gln Ile Lys Thr Ser Leu His Arg
        50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 25
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 25
```

```
Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
                20                  25                  30

Pro Arg Glu Val Gln Val Thr Met Cys Ile Gly Ala Cys Pro Ser Gln
            35                  40                  45

Asn Arg Thr Ala Asn Met His Ala Gln Ile Lys Thr Ser Leu His Arg
        50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105
```

```
<210> SEQ ID NO 26
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 26

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
                20                  25                  30

Pro Arg Glu Val Gln Val Thr Met Cys Ile Gly Ala Cys Pro Ser Gln
            35                  40                  45

Phe Asn Ala Thr Asn Met His Ala Gln Ile Lys Thr Ser Leu His Arg
        50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105
```

```
<210> SEQ ID NO 27
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 27

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
                20                  25                  30

Pro Arg Glu Val Gln Val Thr Met Cys Ile Gly Ala Cys Pro Ser Gln
            35                  40                  45

Phe Arg Ala Ala Asn Met His Ala Gln Ile Lys Thr Asn Leu Thr Arg
        50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
```

Thr Tyr Asp Asp Leu Leu Ala Lys Asp Cys His Cys Ile
            100                 105

<210> SEQ ID NO 28
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 28

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Asn His Thr
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 29
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 29

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Asn Tyr
65                  70                  75                  80

Thr Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 30
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 30

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Asn Thr Thr Thr Gly Val Ser Leu Gln
                85                  90                  95

Thr Tyr Asp Asp Leu Leu Ala Lys Asp Cys His Cys Ile
                100                 105

<210> SEQ ID NO 31
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 31

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asn Thr Thr Val Ser Leu Gln
                85                  90                  95

Thr Tyr Asp Asp Leu Leu Ala Lys Asp Cys His Cys Ile
                100                 105

<210> SEQ ID NO 32
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 32

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Asn Gly Thr Ser Leu Gln
                85                  90                  95

Thr Tyr Asp Asp Leu Leu Ala Lys Asp Cys His Cys Ile

<210> SEQ ID NO 33
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 33

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Asn Ser Thr Gln
                85                  90                  95

Thr Tyr Asp Asp Leu Leu Ala Lys Asp Cys His Cys Ile
            100                 105

<210> SEQ ID NO 34
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 34

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Asn Leu Thr
                85                  90                  95

Thr Tyr Asp Asp Leu Leu Ala Lys Asp Cys His Cys Ile
            100                 105

<210> SEQ ID NO 35
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 35

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
            35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Asn Lys Thr Cys His Cys Ile
            100                 105

<210> SEQ ID NO 36
<211> LENGTH: 4
<212> TYPE: PRT
<213> ORGANISM: Artificial sequence
<220> FEATURE:
<223> OTHER INFORMATION: synthetic polypeptide sequence

<400> SEQUENCE: 36

Arg Gly Arg Arg
1

<210> SEQ ID NO 37
<211> LENGTH: 6
<212> TYPE: PRT
<213> ORGANISM: Artificial sequence
<220> FEATURE:
<223> OTHER INFORMATION: synthetic polypeptide sequence

<400> SEQUENCE: 37

Arg Lys Arg Lys Lys Arg
1               5

<210> SEQ ID NO 38
<211> LENGTH: 4
<212> TYPE: PRT
<213> ORGANISM: Artificial sequence
<220> FEATURE:
<223> OTHER INFORMATION: synthetic polypeptide sequence

<400> SEQUENCE: 38

Arg Lys Lys Arg
1

<210> SEQ ID NO 39
<211> LENGTH: 6
<212> TYPE: PRT
<213> ORGANISM: Artificial sequence
<220> FEATURE:
<223> OTHER INFORMATION: synthetic polypeptide sequence

<400> SEQUENCE: 39

Arg Arg Arg Lys Lys Arg
1               5

<210> SEQ ID NO 40
<211> LENGTH: 4
<212> TYPE: PRT
<213> ORGANISM: Artificial sequence
<220> FEATURE:
<223> OTHER INFORMATION: synthetic polypeptide sequence

<400> SEQUENCE: 40

Gly Gly Gly Ser

```
<210> SEQ ID NO 41
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 41

Gly Gly Gly Gly Ser
1               5

<210> SEQ ID NO 42
<211> LENGTH: 4
<212> TYPE: PRT
<213> ORGANISM: Artificial sequence
<220> FEATURE:
<223> OTHER INFORMATION: synthetic polypeptide sequence

<400> SEQUENCE: 42

Gly Gly Ser Gly
1

<210> SEQ ID NO 43
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 43

Gly Gly Ser Gly Gly
1               5

<210> SEQ ID NO 44
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 44

Gly Ser Gly Ser Gly
1               5

<210> SEQ ID NO 45
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 45

Gly Ser Gly Gly Gly
1               5

<210> SEQ ID NO 46
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 46

Gly Gly Gly Ser Gly
1               5
```

```
<210> SEQ ID NO 47
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 47

Gly Ser Ser Ser Gly
1               5

<210> SEQ ID NO 48
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 48

Gly Gly Gly Ser Gly Gly Gly Ser Ile Glu Gly Arg
1               5                   10

<210> SEQ ID NO 49
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 49

Gly Gly Gly Gly Gly
1               5

<210> SEQ ID NO 50
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 50

Glu Gly Gly Gly Ser
1               5

<210> SEQ ID NO 51
<211> LENGTH: 4
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (2)..(3)
<223> OTHER INFORMATION: the amino acid at this position may be any
      amino acid
<220> FEATURE:
<221> NAME/KEY: MISC_FEATURE
<222> LOCATION: (4)..(4)
<223> OTHER INFORMATION: the amino acid at this position may be any
      hydrophobic amino acid

<400> SEQUENCE: 51

Pro Xaa Xaa Xaa
1

<210> SEQ ID NO 52
<211> LENGTH: 5
```

```
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (2)..(3)
<223> OTHER INFORMATION: the amino acid at this position may be any
      amino acid
<220> FEATURE:
<221> NAME/KEY: MISC_FEATURE
<222> LOCATION: (4)..(4)
<223> OTHER INFORMATION: the amino acid at this position may any
      hydrophobic amino acid
<220> FEATURE:
<221> NAME/KEY: MISC_FEATURE
<222> LOCATION: (5)..(5)
<223> OTHER INFORMATION: the amino acid at this position may be Ser or
      Thr

<400> SEQUENCE: 52

Pro Xaa Xaa Xaa Xaa
1               5

<210> SEQ ID NO 53
<211> LENGTH: 6
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (2)..(2)
<223> OTHER INFORMATION: the amino acid at this position may be Leu or
      Gln

<400> SEQUENCE: 53

Pro Xaa Gly Met Thr Ser
1               5

<210> SEQ ID NO 54
<211> LENGTH: 5
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (2)..(2)
<223> OTHER INFORMATION: the amino acid at this position may be Leu or
      Gln

<400> SEQUENCE: 54

Pro Xaa Gly Met Thr
1               5

<210> SEQ ID NO 55
<211> LENGTH: 10
<212> TYPE: PRT
<213> ORGANISM: Artificial sequence
<220> FEATURE:
<223> OTHER INFORMATION: synthetic polypeptide sequence

<400> SEQUENCE: 55

Cys Gly Leu Val Pro Ala Gly Ser Gly Pro
1               5                   10

<210> SEQ ID NO 56
<211> LENGTH: 12
<212> TYPE: PRT
<213> ORGANISM: Artificial sequence
```

```
<220> FEATURE:
<223> OTHER INFORMATION: synthetic polypeptide sequence

<400> SEQUENCE: 56

Ser Leu Leu Lys Ser Arg Met Val Pro Asn Phe Asn
1               5                   10

<210> SEQ ID NO 57
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 57

Ser Leu Leu Ile Ala Arg Arg Met Pro Asn Phe Asn
1               5                   10

<210> SEQ ID NO 58
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 58

Ser Lys Leu Val Gln Ala Ser Ala Ser Gly Val Asn
1               5                   10

<210> SEQ ID NO 59
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 59

Ser Ser Tyr Leu Lys Ala Ser Asp Ala Pro Asp Asn
1               5                   10

<210> SEQ ID NO 60
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 60

Arg Pro Lys Pro Gln Gln Phe Phe Gly Leu Met Asn
1               5                   10

<210> SEQ ID NO 61
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 61

Ser Leu Arg Pro Leu Ala Leu Trp Arg Ser Phe Asn
1               5                   10

<210> SEQ ID NO 62
<211> LENGTH: 12
<212> TYPE: PRT
<213> ORGANISM: Artificial sequence
<220> FEATURE:
```

```
<223> OTHER INFORMATION: synthetic polypeptide sequence

<400> SEQUENCE: 62

Ser Pro Gln Gly Ile Ala Gly Gln Arg Asn Phe Asn
1               5                   10

<210> SEQ ID NO 63
<211> LENGTH: 14
<212> TYPE: PRT
<213> ORGANISM: Artificial sequence
<220> FEATURE:
<223> OTHER INFORMATION: synthetic polypeptide sequence

<400> SEQUENCE: 63

Asp Val Asp Glu Arg Asp Val Arg Gly Phe Ala Ser Phe Leu
1               5                   10

<210> SEQ ID NO 64
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 64

Ser Leu Pro Leu Gly Leu Trp Ala Pro Asn Phe Asn
1               5                   10

<210> SEQ ID NO 65
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 65

Ser Leu Leu Ile Phe Arg Ser Trp Ala Asn Phe Asn
1               5                   10

<210> SEQ ID NO 66
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 66

Ser Gly Val Val Ile Ala Thr Val Ile Val Ile Thr
1               5                   10

<210> SEQ ID NO 67
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 67

Ser Leu Gly Pro Gln Gly Ile Trp Gly Gln Phe Asn
1               5                   10

<210> SEQ ID NO 68
<211> LENGTH: 12
<212> TYPE: PRT
<213> ORGANISM: Artificial sequence
<220> FEATURE:
<223> OTHER INFORMATION: synthetic polypeptide sequence
```

```
<400> SEQUENCE: 68

Lys Lys Ser Pro Gly Arg Val Val Gly Gly Ser Val
1               5                   10

<210> SEQ ID NO 69
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 69

Pro Gln Gly Leu Leu Gly Ala Pro Gly Ile Leu Gly
1               5                   10

<210> SEQ ID NO 70
<211> LENGTH: 31
<212> TYPE: PRT
<213> ORGANISM: Artificial sequence
<220> FEATURE:
<223> OTHER INFORMATION: synthetic polypeptide sequence

<400> SEQUENCE: 70

His Gly Pro Glu Gly Leu Arg Val Gly Phe Tyr Glu Ser Asp Val Met
1               5                   10                  15

Gly Arg Gly His Ala Arg Leu Val His Val Glu Glu Pro His Thr
            20                  25                  30

<210> SEQ ID NO 71
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 71

Gly Pro Gln Gly Leu Ala Gly Gln Arg Gly Ile Val
1               5                   10

<210> SEQ ID NO 72
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 72

Gly Gly Ser Gly Gln Arg Gly Arg Lys Ala Leu Glu
1               5                   10

<210> SEQ ID NO 73
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 73

Ser Leu Ser Ala Leu Leu Ser Ser Asp Ile Phe Asn
1               5                   10

<210> SEQ ID NO 74
<211> LENGTH: 12
<212> TYPE: PRT
<213> ORGANISM: Artificial sequence
```

```
<220> FEATURE:
<223> OTHER INFORMATION: synthetic polypeptide sequence

<400> SEQUENCE: 74

Ser Leu Pro Arg Phe Lys Ile Ile Gly Gly Phe Asn
1               5                   10

<210> SEQ ID NO 75
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 75

Ser Leu Leu Gly Ile Ala Val Pro Gly Asn Phe Asn
1               5                   10

<210> SEQ ID NO 76
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 76

Phe Phe Lys Asn Ile Val Thr Pro Arg Thr Pro Pro
1               5                   10

<210> SEQ ID NO 77
<211> LENGTH: 734
<212> TYPE: PRT
<213> ORGANISM: Artificial sequence
<220> FEATURE:
<223> OTHER INFORMATION: synthetic polypeptide sequence

<400> SEQUENCE: 77

Met Asp Met Arg Val Pro Ala Gln Leu Leu Gly Leu Leu Leu Leu Trp
1               5                   10                  15

Leu Arg Gly Ala Arg Cys Asp Ala His Lys Ser Glu Val Ala His Arg
                20                  25                  30

Phe Lys Asp Leu Gly Glu Glu Asn Phe Lys Ala Leu Val Leu Ile Ala
            35                  40                  45

Phe Ala Gln Tyr Leu Gln Gln Cys Pro Phe Glu Asp His Val Lys Leu
        50                  55                  60

Val Asn Glu Val Thr Glu Phe Ala Lys Thr Cys Val Ala Asp Glu Ser
65                  70                  75                  80

Ala Glu Asn Cys Asp Lys Ser Leu His Thr Leu Phe Gly Asp Lys Leu
                85                  90                  95

Cys Thr Val Ala Thr Leu Arg Glu Thr Tyr Gly Glu Met Ala Asp Cys
            100                 105                 110

Cys Ala Lys Gln Glu Pro Glu Arg Asn Glu Cys Phe Leu Gln His Lys
        115                 120                 125

Asp Asp Asn Pro Asn Leu Pro Arg Leu Val Arg Pro Glu Val Asp Val
    130                 135                 140

Met Cys Thr Ala Phe His Asp Asn Glu Glu Thr Phe Leu Lys Lys Tyr
145                 150                 155                 160

Leu Tyr Glu Ile Ala Arg Arg His Pro Tyr Phe Tyr Ala Pro Glu Leu
                165                 170                 175

Leu Phe Phe Ala Lys Arg Tyr Lys Ala Ala Phe Thr Glu Cys Cys Gln
            180                 185                 190
```

```
Ala Ala Asp Lys Ala Ala Cys Leu Leu Pro Lys Leu Asp Glu Leu Arg
        195                 200                 205

Asp Glu Gly Lys Ala Ser Ser Ala Lys Gln Arg Leu Lys Cys Ala Ser
    210                 215                 220

Leu Gln Lys Phe Gly Glu Arg Ala Phe Lys Ala Trp Ala Val Ala Arg
225                 230                 235                 240

Leu Ser Gln Arg Phe Pro Lys Ala Glu Phe Ala Glu Val Ser Lys Leu
                245                 250                 255

Val Thr Asp Leu Thr Lys Val His Thr Glu Cys Cys His Gly Asp Leu
            260                 265                 270

Leu Glu Cys Ala Asp Asp Arg Ala Asp Leu Ala Lys Tyr Ile Cys Glu
            275                 280                 285

Asn Gln Asp Ser Ile Ser Ser Lys Leu Lys Glu Cys Cys Glu Lys Pro
    290                 295                 300

Leu Leu Glu Lys Ser His Cys Ile Ala Glu Val Glu Asn Asp Glu Met
305                 310                 315                 320

Pro Ala Asp Leu Pro Ser Leu Ala Ala Asp Phe Val Glu Ser Lys Asp
                325                 330                 335

Val Cys Lys Asn Tyr Ala Glu Ala Lys Asp Val Phe Leu Gly Met Phe
            340                 345                 350

Leu Tyr Glu Tyr Ala Arg Arg His Pro Asp Tyr Ser Val Val Leu Leu
            355                 360                 365

Leu Arg Leu Ala Lys Thr Tyr Glu Thr Thr Leu Glu Lys Cys Cys Ala
    370                 375                 380

Ala Ala Asp Pro His Glu Cys Tyr Ala Lys Val Phe Asp Glu Phe Lys
385                 390                 395                 400

Pro Leu Val Glu Glu Pro Gln Asn Leu Ile Lys Gln Asn Cys Glu Leu
                405                 410                 415

Phe Glu Gln Leu Gly Glu Tyr Lys Phe Gln Asn Ala Leu Leu Val Arg
            420                 425                 430

Tyr Thr Lys Lys Val Pro Gln Val Ser Thr Pro Thr Leu Val Glu Val
    435                 440                 445

Ser Arg Asn Leu Gly Lys Val Gly Ser Lys Cys Cys Lys His Pro Glu
    450                 455                 460

Ala Lys Arg Met Pro Cys Ala Glu Asp Tyr Leu Ser Val Val Leu Asn
465                 470                 475                 480

Gln Leu Cys Val Leu His Glu Lys Thr Pro Val Ser Asp Arg Val Thr
                485                 490                 495

Lys Cys Cys Thr Glu Ser Leu Val Asn Arg Arg Pro Cys Phe Ser Ala
            500                 505                 510

Leu Glu Val Asp Glu Thr Tyr Val Pro Lys Glu Phe Asn Ala Glu Thr
            515                 520                 525

Phe Thr Phe His Ala Asp Ile Cys Thr Leu Ser Glu Lys Glu Arg Gln
    530                 535                 540

Ile Lys Lys Gln Thr Ala Leu Val Glu Leu Val Lys His Lys Pro Lys
545                 550                 555                 560

Ala Thr Lys Glu Gln Leu Lys Ala Val Met Asp Asp Phe Ala Ala Phe
                565                 570                 575

Val Glu Lys Cys Cys Lys Ala Asp Asp Lys Glu Thr Cys Phe Ala Glu
            580                 585                 590

Glu Gly Lys Lys Leu Val Ala Ala Ser Gln Ala Ala Leu Gly Leu Gly
            595                 600                 605
```

```
Gly Gly Gly Ser Gly Gly Gly Ser Gly Gly Gly Ser Ala Arg
    610             615             620

Asn Gly Asp His Cys Pro Leu Gly Pro Gly Arg Cys Cys Arg Leu His
625                 630                 635                 640

Thr Val Arg Ala Ser Leu Glu Asp Leu Gly Trp Ala Asp Trp Val Leu
                645                 650                 655

Ser Pro Arg Glu Val Gln Val Thr Met Cys Ile Gly Ala Cys Pro Ser
                660                 665                 670

Gln Phe Arg Ala Ala Asn Met His Ala Gln Ile Lys Thr Ser Leu His
            675                 680                 685

Arg Leu Lys Pro Asp Thr Val Pro Ala Pro Cys Cys Val Pro Ala Ser
690                 695                 700

Tyr Asn Pro Met Val Leu Ile Gln Lys Thr Asp Thr Gly Val Ser Leu
705                 710                 715                 720

Gln Thr Tyr Asp Asp Leu Leu Ala Lys Asp Cys His Cys Ile
                725                 730
```

<210> SEQ ID NO 78
<211> LENGTH: 731
<212> TYPE: PRT
<213> ORGANISM: Artificial sequence
<220> FEATURE:
<223> OTHER INFORMATION: synthetic polypeptide sequence

<400> SEQUENCE: 78

```
Met Asp Met Arg Val Pro Ala Gln Leu Leu Gly Leu Leu Leu Leu Trp
1               5                   10                  15

Leu Arg Gly Ala Arg Cys Asp Ala His Lys Ser Glu Val Ala His Arg
                20                  25                  30

Phe Lys Asp Leu Gly Glu Glu Asn Phe Lys Ala Leu Val Leu Ile Ala
            35                  40                  45

Phe Ala Gln Tyr Leu Gln Gln Cys Pro Phe Glu Asp His Val Lys Leu
        50                  55                  60

Val Asn Glu Val Thr Glu Phe Ala Lys Thr Cys Val Ala Asp Glu Ser
65                  70                  75                  80

Ala Glu Asn Cys Asp Lys Ser Leu His Thr Leu Phe Gly Asp Lys Leu
                85                  90                  95

Cys Thr Val Ala Thr Leu Arg Glu Thr Tyr Gly Glu Met Ala Asp Cys
            100                 105                 110

Cys Ala Lys Gln Glu Pro Glu Arg Asn Glu Cys Phe Leu Gln His Lys
        115                 120                 125

Asp Asp Asn Pro Asn Leu Pro Arg Leu Val Arg Pro Glu Val Asp Val
    130                 135                 140

Met Cys Thr Ala Phe His Asp Asn Glu Glu Thr Phe Leu Lys Lys Tyr
145                 150                 155                 160

Leu Tyr Glu Ile Ala Arg Arg His Pro Tyr Phe Tyr Ala Pro Glu Leu
                165                 170                 175

Leu Phe Phe Ala Lys Arg Tyr Lys Ala Ala Phe Thr Glu Cys Cys Gln
            180                 185                 190

Ala Ala Asp Lys Ala Ala Cys Leu Leu Pro Lys Leu Asp Glu Leu Arg
        195                 200                 205

Asp Glu Gly Lys Ala Ser Ser Ala Lys Gln Arg Leu Lys Cys Ala Ser
    210                 215                 220

Leu Gln Lys Phe Gly Glu Arg Ala Phe Lys Ala Trp Ala Val Ala Arg
225                 230                 235                 240
```

```
Leu Ser Gln Arg Phe Pro Lys Ala Glu Phe Ala Glu Val Ser Lys Leu
            245                 250                 255
Val Thr Asp Leu Thr Lys Val His Thr Glu Cys Cys His Gly Asp Leu
        260                 265                 270
Leu Glu Cys Ala Asp Asp Arg Ala Asp Leu Ala Lys Tyr Ile Cys Glu
    275                 280                 285
Asn Gln Asp Ser Ile Ser Ser Lys Leu Lys Glu Cys Cys Glu Lys Pro
290                 295                 300
Leu Leu Glu Lys Ser His Cys Ile Ala Glu Val Glu Asn Asp Glu Met
305                 310                 315                 320
Pro Ala Asp Leu Pro Ser Leu Ala Ala Asp Phe Val Glu Ser Lys Asp
                325                 330                 335
Val Cys Lys Asn Tyr Ala Glu Ala Lys Asp Val Phe Leu Gly Met Phe
            340                 345                 350
Leu Tyr Glu Tyr Ala Arg Arg His Pro Asp Tyr Ser Val Val Leu Leu
        355                 360                 365
Leu Arg Leu Ala Lys Thr Tyr Glu Thr Thr Leu Glu Lys Cys Cys Ala
    370                 375                 380
Ala Ala Asp Pro His Glu Cys Tyr Ala Lys Val Phe Asp Glu Phe Lys
385                 390                 395                 400
Pro Leu Val Glu Glu Pro Gln Asn Leu Ile Lys Gln Asn Cys Glu Leu
                405                 410                 415
Phe Glu Gln Leu Gly Glu Tyr Lys Phe Gln Asn Ala Leu Leu Val Arg
            420                 425                 430
Tyr Thr Lys Lys Val Pro Gln Val Ser Thr Pro Thr Leu Val Glu Val
        435                 440                 445
Ser Arg Asn Leu Gly Lys Val Gly Ser Lys Cys Cys Lys His Pro Glu
    450                 455                 460
Ala Lys Arg Met Pro Cys Ala Glu Asp Tyr Leu Ser Val Val Leu Asn
465                 470                 475                 480
Gln Leu Cys Val Leu His Glu Lys Thr Pro Val Ser Asp Arg Val Thr
                485                 490                 495
Lys Cys Cys Thr Glu Ser Leu Val Asn Arg Arg Pro Cys Phe Ser Ala
            500                 505                 510
Leu Glu Val Asp Glu Thr Tyr Val Pro Lys Glu Phe Asn Ala Glu Thr
        515                 520                 525
Phe Thr Phe His Ala Asp Ile Cys Thr Leu Ser Glu Lys Glu Arg Gln
    530                 535                 540
Ile Lys Lys Gln Thr Ala Leu Val Glu Leu Val Lys His Lys Pro Lys
545                 550                 555                 560
Ala Thr Lys Glu Gln Leu Lys Ala Val Met Asp Asp Phe Ala Ala Phe
                565                 570                 575
Val Glu Lys Cys Cys Lys Ala Asp Asp Lys Glu Thr Cys Phe Ala Glu
            580                 585                 590
Glu Gly Lys Lys Leu Val Ala Ala Ser Gln Ala Ala Leu Gly Leu Gly
        595                 600                 605
Gly Gly Gly Ser Gly Gly Gly Ser Gly Gly Gly Gly Ser Gly Asp
    610                 615                 620
His Cys Pro Leu Gly Pro Gly Arg Cys Cys Arg Leu His Thr Val Arg
625                 630                 635                 640
Ala Ser Leu Glu Asp Leu Gly Trp Ala Asp Trp Val Leu Ser Pro Arg
                645                 650                 655
Glu Val Gln Val Thr Met Cys Ile Gly Ala Cys Pro Ser Gln Phe Arg
```

```
                   660                 665                 670
Ala Ala Asn Met His Ala Gln Ile Lys Thr Ser Leu His Arg Leu Lys
            675                 680                 685

Pro Asp Thr Val Pro Ala Pro Cys Cys Val Pro Ala Ser Tyr Asn Pro
690                 695                 700

Met Val Leu Ile Gln Lys Thr Asp Thr Gly Val Ser Leu Gln Thr Tyr
705                 710                 715                 720

Asp Asp Leu Leu Ala Lys Asp Cys His Cys Ile
            725                 730

<210> SEQ ID NO 79
<211> LENGTH: 741
<212> TYPE: PRT
<213> ORGANISM: Artificial sequence
<220> FEATURE:
<223> OTHER INFORMATION: synthetic polypeptide sequence

<400> SEQUENCE: 79

Met Asp Met Arg Val Pro Ala Gln Leu Leu Gly Leu Leu Leu Leu Trp
1               5                   10                  15

Leu Arg Gly Ala Arg Cys Asp Ala His Lys Ser Glu Val Ala His Arg
            20                  25                  30

Phe Lys Asp Leu Gly Glu Glu Asn Phe Lys Ala Leu Val Leu Ile Ala
        35                  40                  45

Phe Ala Gln Tyr Leu Gln Gln Cys Pro Phe Glu Asp His Val Lys Leu
    50                  55                  60

Val Asn Glu Val Thr Glu Phe Ala Lys Thr Cys Val Ala Asp Glu Ser
65                  70                  75                  80

Ala Glu Asn Cys Asp Lys Ser Leu His Thr Leu Phe Gly Asp Lys Leu
                85                  90                  95

Cys Thr Val Ala Thr Leu Arg Glu Thr Tyr Gly Glu Met Ala Asp Cys
            100                 105                 110

Cys Ala Lys Gln Glu Pro Glu Arg Asn Glu Cys Phe Leu Gln His Lys
        115                 120                 125

Asp Asp Asn Pro Asn Leu Pro Arg Leu Val Arg Pro Glu Val Asp Val
130                 135                 140

Met Cys Thr Ala Phe His Asp Asn Glu Glu Thr Phe Leu Lys Lys Tyr
145                 150                 155                 160

Leu Tyr Glu Ile Ala Arg Arg His Pro Tyr Phe Tyr Ala Pro Glu Leu
                165                 170                 175

Leu Phe Phe Ala Lys Arg Tyr Lys Ala Ala Phe Thr Glu Cys Cys Gln
            180                 185                 190

Ala Ala Asp Lys Ala Ala Cys Leu Leu Pro Lys Leu Asp Glu Leu Arg
        195                 200                 205

Asp Glu Gly Lys Ala Ser Ser Ala Lys Gln Arg Leu Lys Cys Ala Ser
210                 215                 220

Leu Gln Lys Phe Gly Glu Arg Ala Phe Lys Ala Trp Ala Val Ala Arg
225                 230                 235                 240

Leu Ser Gln Arg Phe Pro Lys Ala Glu Phe Ala Glu Val Ser Lys Leu
                245                 250                 255

Val Thr Asp Leu Thr Lys Val His Thr Glu Cys Cys His Gly Asp Leu
            260                 265                 270

Leu Glu Cys Ala Asp Asp Arg Ala Asp Leu Ala Lys Tyr Ile Cys Glu
        275                 280                 285

Asn Gln Asp Ser Ile Ser Ser Lys Leu Lys Glu Cys Cys Glu Lys Pro
```

```
            290                 295                 300
Leu Leu Glu Lys Ser His Cys Ile Ala Glu Val Glu Asn Asp Glu Met
305                 310                 315                 320

Pro Ala Asp Leu Pro Ser Leu Ala Ala Asp Phe Val Glu Ser Lys Asp
                325                 330                 335

Val Cys Lys Asn Tyr Ala Glu Ala Lys Asp Val Phe Leu Gly Met Phe
            340                 345                 350

Leu Tyr Glu Tyr Ala Arg Arg His Pro Asp Tyr Ser Val Val Leu Leu
        355                 360                 365

Leu Arg Leu Ala Lys Thr Tyr Glu Thr Thr Leu Glu Lys Cys Cys Ala
    370                 375                 380

Ala Ala Asp Pro His Glu Cys Tyr Ala Lys Val Phe Asp Glu Phe Lys
385                 390                 395                 400

Pro Leu Val Glu Glu Pro Gln Asn Leu Ile Lys Gln Asn Cys Glu Leu
                405                 410                 415

Phe Glu Gln Leu Gly Glu Tyr Lys Phe Gln Asn Ala Leu Leu Val Arg
            420                 425                 430

Tyr Thr Lys Lys Val Pro Gln Val Ser Thr Pro Thr Leu Val Glu Val
        435                 440                 445

Ser Arg Asn Leu Gly Lys Val Gly Ser Lys Cys Cys Lys His Pro Glu
    450                 455                 460

Ala Lys Arg Met Pro Cys Ala Glu Asp Tyr Leu Ser Val Val Leu Asn
465                 470                 475                 480

Gln Leu Cys Val Leu His Glu Lys Thr Pro Val Ser Asp Arg Val Thr
                485                 490                 495

Lys Cys Cys Thr Glu Ser Leu Val Asn Arg Arg Pro Cys Phe Ser Ala
            500                 505                 510

Leu Glu Val Asp Glu Thr Tyr Val Pro Lys Glu Phe Asn Ala Glu Thr
        515                 520                 525

Phe Thr Phe His Ala Asp Ile Cys Thr Leu Ser Glu Lys Glu Arg Gln
    530                 535                 540

Ile Lys Lys Gln Thr Ala Leu Val Glu Leu Val Lys His Lys Pro Lys
545                 550                 555                 560

Ala Thr Lys Glu Gln Leu Lys Ala Val Met Asp Asp Phe Ala Ala Phe
                565                 570                 575

Val Glu Lys Cys Cys Lys Ala Asp Asp Lys Glu Thr Cys Phe Ala Glu
            580                 585                 590

Glu Gly Lys Lys Leu Val Ala Ala Ser Gln Ala Ala Leu Gly Leu Gly
        595                 600                 605

Gly Gly Gly Ser Gly Gly Gly Ser Gly Gly Gly Ser Gly Gly
    610                 615                 620

Gly Gly Ser Gly Gly Gly Ser Gly Asp His Cys Pro Leu Gly Pro
625                 630                 635                 640

Gly Arg Cys Cys Arg Leu His Thr Val Arg Ala Ser Leu Glu Asp Leu
                645                 650                 655

Gly Trp Ala Asp Trp Val Leu Ser Pro Arg Glu Val Gln Val Thr Met
            660                 665                 670

Cys Ile Gly Ala Cys Pro Ser Gln Phe Arg Ala Ala Asn Met His Ala
        675                 680                 685

Gln Ile Lys Thr Ser Leu His Arg Leu Lys Pro Asp Thr Val Pro Ala
    690                 695                 700

Pro Cys Cys Val Pro Ala Ser Tyr Asn Pro Met Val Leu Ile Gln Lys
705                 710                 715                 720
```

Thr Asp Thr Gly Val Ser Leu Gln Thr Tyr Asp Asp Leu Leu Ala Lys
            725                 730                 735

Asp Cys His Cys Ile
            740

<210> SEQ ID NO 80
<211> LENGTH: 738
<212> TYPE: PRT
<213> ORGANISM: Artificial sequence
<220> FEATURE:
<223> OTHER INFORMATION: synthetic polypeptide sequence

<400> SEQUENCE: 80

Met Asp Met Arg Val Pro Ala Gln Leu Leu Gly Leu Leu Leu Leu Trp
1               5                   10                  15

Leu Arg Gly Ala Arg Cys Asp Ala His Lys Ser Glu Val Ala His Arg
            20                  25                  30

Phe Lys Asp Leu Gly Glu Glu Asn Phe Lys Ala Leu Val Leu Ile Ala
        35                  40                  45

Phe Ala Gln Tyr Leu Gln Gln Cys Pro Phe Glu Asp His Val Lys Leu
    50                  55                  60

Val Asn Glu Val Thr Glu Phe Ala Lys Thr Cys Val Ala Asp Glu Ser
65                  70                  75                  80

Ala Glu Asn Cys Asp Lys Ser Leu His Thr Leu Phe Gly Asp Lys Leu
                85                  90                  95

Cys Thr Val Ala Thr Leu Arg Glu Thr Tyr Gly Glu Met Ala Asp Cys
            100                 105                 110

Cys Ala Lys Gln Glu Pro Glu Arg Asn Glu Cys Phe Leu Gln His Lys
        115                 120                 125

Asp Asp Asn Pro Asn Leu Pro Arg Leu Val Arg Pro Glu Val Asp Val
    130                 135                 140

Met Cys Thr Ala Phe His Asp Asn Glu Glu Thr Phe Leu Lys Lys Tyr
145                 150                 155                 160

Leu Tyr Glu Ile Ala Arg Arg His Pro Tyr Phe Tyr Ala Pro Glu Leu
                165                 170                 175

Leu Phe Phe Ala Lys Arg Tyr Lys Ala Ala Phe Thr Glu Cys Cys Gln
            180                 185                 190

Ala Ala Asp Lys Ala Ala Cys Leu Leu Pro Lys Leu Asp Glu Leu Arg
        195                 200                 205

Asp Glu Gly Lys Ala Ser Ser Ala Lys Gln Arg Leu Lys Cys Ala Ser
    210                 215                 220

Leu Gln Lys Phe Gly Glu Arg Ala Phe Lys Ala Trp Ala Val Ala Arg
225                 230                 235                 240

Leu Ser Gln Arg Phe Pro Lys Ala Glu Phe Ala Glu Val Ser Lys Leu
                245                 250                 255

Val Thr Asp Leu Thr Lys Val His Thr Glu Cys Cys His Gly Asp Leu
            260                 265                 270

Leu Glu Cys Ala Asp Asp Arg Ala Asp Leu Ala Lys Tyr Ile Cys Glu
        275                 280                 285

Asn Gln Asp Ser Ile Ser Ser Lys Leu Lys Glu Cys Cys Glu Lys Pro
    290                 295                 300

Leu Leu Glu Lys Ser His Cys Ile Ala Glu Val Glu Asn Asp Glu Met
305                 310                 315                 320

Pro Ala Asp Leu Pro Ser Leu Ala Ala Asp Phe Val Glu Ser Lys Asp
                325                 330                 335

```
Val Cys Lys Asn Tyr Ala Glu Ala Lys Asp Val Phe Leu Gly Met Phe
            340                 345                 350

Leu Tyr Glu Tyr Ala Arg Arg His Pro Asp Tyr Ser Val Val Leu Leu
        355                 360                 365

Leu Arg Leu Ala Lys Thr Tyr Glu Thr Thr Leu Glu Lys Cys Cys Ala
    370                 375                 380

Ala Ala Asp Pro His Glu Cys Tyr Ala Lys Val Phe Asp Glu Phe Lys
385                 390                 395                 400

Pro Leu Val Glu Glu Pro Gln Asn Leu Ile Lys Gln Asn Cys Glu Leu
                405                 410                 415

Phe Glu Gln Leu Gly Glu Tyr Lys Phe Gln Asn Ala Leu Leu Val Arg
            420                 425                 430

Tyr Thr Lys Lys Val Pro Gln Val Ser Thr Pro Thr Leu Val Glu Val
        435                 440                 445

Ser Arg Asn Leu Gly Lys Val Gly Ser Lys Cys Cys Lys His Pro Glu
    450                 455                 460

Ala Lys Arg Met Pro Cys Ala Glu Asp Tyr Leu Ser Val Val Leu Asn
465                 470                 475                 480

Gln Leu Cys Val Leu His Glu Lys Thr Pro Val Ser Asp Arg Val Thr
                485                 490                 495

Lys Cys Cys Thr Glu Ser Leu Val Asn Arg Arg Pro Cys Phe Ser Ala
            500                 505                 510

Leu Glu Val Asp Glu Thr Tyr Val Pro Lys Glu Phe Asn Ala Glu Thr
        515                 520                 525

Phe Thr Phe His Ala Asp Ile Cys Thr Leu Ser Glu Lys Glu Arg Gln
    530                 535                 540

Ile Lys Lys Gln Thr Ala Leu Val Glu Leu Val Lys His Lys Pro Lys
545                 550                 555                 560

Ala Thr Lys Glu Gln Leu Lys Ala Val Met Asp Asp Phe Ala Ala Phe
                565                 570                 575

Val Glu Lys Cys Cys Lys Ala Asp Asp Lys Glu Thr Cys Phe Ala Glu
            580                 585                 590

Glu Gly Lys Lys Leu Val Ala Ala Ser Gln Ala Ala Leu Gly Leu Gly
        595                 600                 605

Gly Gly Gly Ser Gly Gly Gly Ser Gly Gly Gly Gly Ser Gly Gly
    610                 615                 620

Gly Gly Ser Gly Gly Gly Ser Cys Pro Leu Gly Pro Gly Arg Cys
625                 630                 635                 640

Cys Arg Leu His Thr Val Arg Ala Ser Leu Glu Asp Leu Gly Trp Ala
                645                 650                 655

Asp Trp Val Leu Ser Pro Arg Glu Val Gln Val Thr Met Cys Ile Gly
            660                 665                 670

Ala Cys Pro Ser Gln Phe Arg Ala Ala Asn Met His Ala Gln Ile Lys
        675                 680                 685

Thr Ser Leu His Arg Leu Lys Pro Asp Thr Val Pro Ala Pro Cys Cys
    690                 695                 700

Val Pro Ala Ser Tyr Asn Pro Met Val Leu Ile Gln Lys Thr Asp Thr
705                 710                 715                 720

Gly Val Ser Leu Gln Thr Tyr Asp Asp Leu Leu Ala Lys Asp Cys His
                725                 730                 735

Cys Ile
```

<210> SEQ ID NO 81
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 81

```
Met Asp Met Arg Val Pro Ala Gln Leu Leu Gly Leu Leu Leu Trp
1               5                   10                  15

Leu Arg Gly Ala Arg Cys Ala Arg Asn Gly Thr His Cys Pro Leu Gly
            20                  25                  30

Pro Gly Arg Cys Cys Arg Leu His Thr Val Asn Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Ser Leu Gln Thr Tyr Asp Asp Leu Leu Ala
        115                 120                 125

Lys Asp Cys His Cys Ile
    130
```

<210> SEQ ID NO 82
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 82

```
Met Asp Met Arg Val Pro Ala Gln Leu Leu Gly Leu Leu Leu Trp
1               5                   10                  15

Leu Arg Gly Ala Arg Cys Ala Arg Asn Gly Asp His Cys Pro Leu Gly
            20                  25                  30

Pro Gly Arg Cys Cys Asn Leu Thr Thr Val Arg Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Ser Leu Gln Thr Tyr Asp Asp Leu Leu Ala
        115                 120                 125

Lys Asp Cys His Cys Ile
    130
```

<210> SEQ ID NO 83
<211> LENGTH: 134
<212> TYPE: PRT
<213> ORGANISM: Artificial sequence
<220> FEATURE:

<223> OTHER INFORMATION: synthetic polypeptide sequence

<400> SEQUENCE: 83

```
Met Asp Met Arg Val Pro Ala Gln Leu Leu Gly Leu Leu Leu Leu Trp
1               5                   10                  15
Leu Arg Gly Ala Arg Cys Ala Arg Asn Gly Asp His Cys Pro Leu Gly
            20                  25                  30
Pro Gly Arg Cys Cys Arg Leu His Thr Val Arg Ala Asn Leu Thr Asp
        35                  40                  45
Leu Gly Trp Ala Asp Trp Val Leu Ser Pro Arg Glu Val Gln Val Thr
    50                  55                  60
Met Cys Ile Gly Ala Cys Pro Ser Gln Phe Arg Ala Ala Asn Met His
65                  70                  75                  80
Ala Gln Ile Lys Thr Ser Leu His Arg Leu Lys Pro Asp Thr Val Pro
                85                  90                  95
Ala Pro Cys Cys Val Pro Ala Ser Tyr Asn Pro Met Val Leu Ile Gln
            100                 105                 110
Lys Thr Asp Thr Gly Val Ser Leu Gln Thr Tyr Asp Asp Leu Leu Ala
        115                 120                 125
Lys Asp Cys His Cys Ile
    130
```

<210> SEQ ID NO 84
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 84

```
Met Asp Met Arg Val Pro Ala Gln Leu Leu Gly Leu Leu Leu Leu Trp
1               5                   10                  15
Leu Arg Gly Ala Arg Cys Ala Arg Asn Gly Asp His Cys Pro Leu Gly
            20                  25                  30
Pro Gly Arg Cys Cys Arg Leu His Thr Val Arg Ala Ser Asn Glu Thr
        35                  40                  45
Leu Gly Trp Ala Asp Trp Val Leu Ser Pro Arg Glu Val Gln Val Thr
    50                  55                  60
Met Cys Ile Gly Ala Cys Pro Ser Gln Phe Arg Ala Ala Asn Met His
65                  70                  75                  80
Ala Gln Ile Lys Thr Ser Leu His Arg Leu Lys Pro Asp Thr Val Pro
                85                  90                  95
Ala Pro Cys Cys Val Pro Ala Ser Tyr Asn Pro Met Val Leu Ile Gln
            100                 105                 110
Lys Thr Asp Thr Gly Val Ser Leu Gln Thr Tyr Asp Asp Leu Leu Ala
        115                 120                 125
Lys Asp Cys His Cys Ile
    130
```

<210> SEQ ID NO 85
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 85

Met Asp Met Arg Val Pro Ala Gln Leu Leu Gly Leu Leu Leu Leu Trp

```
            1               5                  10                 15
Leu Arg Gly Ala Arg Cys Ala Arg Asn Gly Asp His Cys Pro Leu Gly
                20                  25                  30

Pro Gly Arg Cys Cys Arg Leu His Thr Val Arg Ala Ser Leu Glu Asp
                35                  40                  45

Leu Gly Trp Ala Asp Trp Val Leu Ser Pro Arg Glu Val Gln Val Thr
        50                  55                  60

Met Cys Ile Gly Ala Cys Pro Asn Gln Thr Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
                100                 105                 110

Lys Thr Asp Thr Gly Val Ser Leu Gln Thr Tyr Asp Asp Leu Leu Ala
                115                 120                 125

Lys Asp Cys His Cys Ile
                130

<210> SEQ ID NO 86
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 86

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
                20                  25                  30

Pro Gly Arg Cys Cys Arg Leu His Thr Val Arg Ala Ser Leu Glu Asp
                35                  40                  45

Leu Gly Trp Ala Asp Trp Val Leu Ser Pro Arg Glu Val Gln Val Thr
        50                  55                  60

Met Cys Ile Gly Ala Cys Pro Ser Asn Phe Thr Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
                100                 105                 110

Lys Thr Asp Thr Gly Val Ser Leu Gln Thr Tyr Asp Asp Leu Leu Ala
                115                 120                 125

Lys Asp Cys His Cys Ile
                130

<210> SEQ ID NO 87
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 87

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
                20                  25                  30
```

```
Pro Gly Arg Cys Cys Arg Leu His Thr Val Arg Ala Ser Leu Glu Asp
         35                  40                  45

Leu Gly Trp Ala Asp Trp Val Leu Ser Pro Arg Glu Val Gln Val Thr
 50                  55                  60

Met Cys Ile Gly Ala Cys Pro Ser Gln Asn Arg Thr Ala Asn Met His
 65                  70                  75                  80

Ala Gln Ile Lys Thr Ser Leu His Arg Leu Lys Pro Asp Thr Val Pro
                 85                  90                  95

Ala Pro Cys Cys Val Pro Ala Ser Tyr Asn Pro Met Val Leu Ile Gln
                100                 105                 110

Lys Thr Asp Thr Gly Val Ser Leu Gln Thr Tyr Asp Asp Leu Leu Ala
                115                 120                 125

Lys Asp Cys His Cys Ile
            130

<210> SEQ ID NO 88
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 88

Met Asp Met Arg Val Pro Ala Gln Leu Leu Gly Leu Leu Leu Leu Trp
 1               5                  10                  15

Leu Arg Gly Ala Arg Cys Ala Arg Asn Gly Asp His Cys Pro Leu Gly
                 20                  25                  30

Pro Gly Arg Cys Cys Arg Leu His Thr Val Arg Ala Ser Leu Glu Asp
         35                  40                  45

Leu Gly Trp Ala Asp Trp Val Leu Ser Pro Arg Glu Val Gln Val Thr
 50                  55                  60

Met Cys Ile Gly Ala Cys Pro Ser Gln Phe Asn Ala Thr Asn Met His
 65                  70                  75                  80

Ala Gln Ile Lys Thr Ser Leu His Arg Leu Lys Pro Asp Thr Val Pro
                 85                  90                  95

Ala Pro Cys Cys Val Pro Ala Ser Tyr Asn Pro Met Val Leu Ile Gln
                100                 105                 110

Lys Thr Asp Thr Gly Val Ser Leu Gln Thr Tyr Asp Asp Leu Leu Ala
                115                 120                 125

Lys Asp Cys His Cys Ile
            130

<210> SEQ ID NO 89
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 89

Met Asp Met Arg Val Pro Ala Gln Leu Leu Gly Leu Leu Leu Leu Trp
 1               5                  10                  15

Leu Arg Gly Ala Arg Cys Ala Arg Asn Gly Asp His Cys Pro Leu Gly
                 20                  25                  30

Pro Gly Arg Cys Cys Arg Leu His Thr Val Arg Ala Ser Leu Glu Asp
         35                  40                  45

Leu Gly Trp Ala Asp Trp Val Leu Ser Pro Arg Glu Val Gln Val Thr
 50                  55                  60
```

Met Cys Ile Gly Ala Cys Pro Ser Gln Phe Arg Ala Ala Asn Met His
65                  70                  75                  80

Ala Gln Ile Lys Thr Asn Leu Thr Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Ser Leu Gln Thr Tyr Asp Asp Leu Leu Ala
        115                 120                 125

Lys Asp Cys His Cys Ile
    130

<210> SEQ ID NO 90
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 90

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
                20                  25                  30

Pro Gly Arg Cys Cys Arg Leu His Thr Val Arg Ala Ser Leu Glu Asp
            35                  40                  45

Leu Gly Trp Ala Asp Trp Val Leu Ser Pro Arg Glu Val Gln Val Thr
        50                  55                  60

Met Cys Ile Gly Ala Cys Pro Ser Gln Phe Arg Ala Ala Asn Met His
65                  70                  75                  80

Ala Gln Ile Lys Thr Ser Asn His Thr Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Ser Leu Gln Thr Tyr Asp Asp Leu Leu Ala
        115                 120                 125

Lys Asp Cys His Cys Ile
    130

<210> SEQ ID NO 91
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 91

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
                20                  25                  30

Pro Gly Arg Cys Cys Arg Leu His Thr Val Arg Ala Ser Leu Glu Asp
            35                  40                  45

Leu Gly Trp Ala Asp Trp Val Leu Ser Pro Arg Glu Val Gln Val Thr
        50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro

```
                85                  90                  95

Ala Pro Cys Cys Val Pro Ala Asn Tyr Thr Pro Met Val Leu Ile Gln
            100                 105                 110

Lys Thr Asp Thr Gly Val Ser Leu Gln Thr Tyr Asp Leu Leu Ala
        115                 120                 125

Lys Asp Cys His Cys Ile
    130

<210> SEQ ID NO 92
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 92

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
            20                  25                  30

Pro Gly Arg Cys Cys Arg Leu His Thr Val Arg Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Asn Thr Thr Thr Gly Val Ser Leu Gln Thr Tyr Asp Asp Leu Leu Ala
        115                 120                 125

Lys Asp Cys His Cys Ile
    130

<210> SEQ ID NO 93
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 93

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
            20                  25                  30

Pro Gly Arg Cys Cys Arg Leu His Thr Val Arg Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110
```

Lys Thr Asn Thr Thr Val Ser Leu Gln Thr Tyr Asp Asp Leu Leu Ala
            115                 120                 125

Lys Asp Cys His Cys Ile
    130

<210> SEQ ID NO 94
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 94

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
            20                  25                  30

Pro Gly Arg Cys Cys Arg Leu His Thr Val Arg Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Asn Gly Thr Ser Leu Gln Thr Tyr Asp Asp Leu Leu Ala
        115                 120                 125

Lys Asp Cys His Cys Ile
    130

<210> SEQ ID NO 95
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 95

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
            20                  25                  30

Pro Gly Arg Cys Cys Arg Leu His Thr Val Arg Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Asn Ser Thr Gln Thr Tyr Asp Asp Leu Leu Ala
        115                 120                 125

Lys Asp Cys His Cys Ile
    130

-continued

```
<210> SEQ ID NO 96
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 96

Met Asp Met Arg Val Pro Ala Gln Leu Gly Leu Leu Leu Trp
1               5                  10                  15

Leu Arg Gly Ala Arg Cys Ala Arg Asn Gly Asp His Cys Pro Leu Gly
            20                  25                  30

Pro Gly Arg Cys Cys Arg Leu His Thr Val Arg Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Asn Leu Thr Thr Tyr Asp Asp Leu Leu Ala
        115                 120                 125

Lys Asp Cys His Cys Ile
    130

<210> SEQ ID NO 97
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 97

Met Asp Met Arg Val Pro Ala Gln Leu Gly Leu Leu Leu Trp
1               5                  10                  15

Leu Arg Gly Ala Arg Cys Ala Arg Asn Gly Asp His Cys Pro Leu Gly
            20                  25                  30

Pro Gly Arg Cys Cys Arg Leu His Thr Val Arg Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Ser Leu Gln Thr Tyr Asp Asp Leu Leu Asn
        115                 120                 125

Lys Thr Cys His Cys Ile
    130

<210> SEQ ID NO 98
<211> LENGTH: 70
<212> TYPE: DNA
```

-continued

<213> ORGANISM: Artificial Sequence
<220> FEATURE:
<223> OTHER INFORMATION: synthetic polynucleotide sequence

<400> SEQUENCE: 98
caccatggac atgagggtcc ccgctcagct cctggggctc ctgctactct ggctccgagg    60
tgccagatgt                                                           70

<210> SEQ ID NO 99
<211> LENGTH: 48
<212> TYPE: DNA
<213> ORGANISM: Artificial sequence
<220> FEATURE:
<223> OTHER INFORMATION: synthetic polynucleotide sequence

<400> SEQUENCE: 99
cctcgagcgg ccgctagctc atatgcagtg gcagtctttg gctaacaa                 48

<210> SEQ ID NO 100
<211> LENGTH: 131
<212> TYPE: PRT
<213> ORGANISM: Artificial sequence
<220> FEATURE:
<223> OTHER INFORMATION: synthetic polypeptide sequence

<400> SEQUENCE: 100

Met Asp Met Arg Val Pro Ala Gln Leu Leu Gly Leu Leu Leu Leu Trp
1               5                   10                  15

Leu Arg Gly Ala Arg Cys Gly Asp His Cys Pro Leu Gly Pro Gly Arg
            20                  25                  30

Cys Cys Arg Leu His Thr Val Arg Ala Ser Leu Glu Asp Leu Gly Trp
        35                  40                  45

Ala Asp Trp Val Leu Ser Pro Arg Glu Val Gln Val Thr Met Cys Ile
    50                  55                  60

Gly Ala Cys Pro Ser Gln Phe Arg Ala Ala Asn Met His Ala Gln Ile
65                  70                  75                  80

Lys Thr Ser Leu His Arg Leu Lys Pro Asp Thr Val Pro Ala Pro Cys
                85                  90                  95

Cys Val Pro Ala Ser Tyr Asn Pro Met Val Leu Ile Gln Asn Thr Thr
            100                 105                 110

Thr Gly Val Ser Leu Gln Thr Tyr Asp Asp Leu Leu Ala Lys Asp Cys
        115                 120                 125

His Cys Ile
    130

<210> SEQ ID NO 101
<211> LENGTH: 22
<212> TYPE: PRT
<213> ORGANISM: Artificial sequence
<220> FEATURE:
<223> OTHER INFORMATION: synthetic polypeptide sequence

<400> SEQUENCE: 101

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 102
<211> LENGTH: 48
<212> TYPE: DNA

```
<213> ORGANISM: Artificial sequence
<220> FEATURE:
<223> OTHER INFORMATION: synthetic polynucleotide sequence

<400> SEQUENCE: 102
ctccgaggtg ccagatgtgc gcgcaacggg gaccactgtc cgctcggg                 48

<210> SEQ ID NO 103
<211> LENGTH: 577
<212> TYPE: PRT
<213> ORGANISM: Artificial sequence
<220> FEATURE:
<223> OTHER INFORMATION: Synthetic polypeptide

<400> SEQUENCE: 103
```

| | | | | | | | | | | | | | | | |
|---|---|---|---|---|---|---|---|---|---|---|---|---|---|---|---|
| Asp | Ala | His | Lys | Ser | Glu | Val | Ala | His | Arg | Phe | Lys | Asp | Leu | Gly | Glu |
| 1 | | | | 5 | | | | | 10 | | | | | 15 | |
| Glu | Asn | Phe | Lys | Ala | Leu | Val | Leu | Ile | Ala | Phe | Ala | Gln | Tyr | Leu | Gln |
| | | | 20 | | | | | 25 | | | | | 30 | | |
| Gln | Cys | Pro | Phe | Glu | Asp | His | Val | Lys | Leu | Val | Asn | Glu | Val | Thr | Glu |
| | | 35 | | | | | 40 | | | | | 45 | | | |
| Phe | Ala | Lys | Thr | Cys | Val | Ala | Asp | Glu | Ser | Ala | Glu | Asn | Cys | Asp | Lys |
| | 50 | | | | | 55 | | | | | 60 | | | | |
| Ser | Leu | His | Thr | Leu | Phe | Gly | Asp | Lys | Leu | Cys | Thr | Val | Ala | Thr | Leu |
| 65 | | | | | 70 | | | | | 75 | | | | | 80 |
| Arg | Glu | Thr | Tyr | Gly | Glu | Met | Ala | Asp | Cys | Cys | Ala | Lys | Gln | Glu | Pro |
| | | | | 85 | | | | | 90 | | | | | 95 | |
| Glu | Arg | Asn | Glu | Cys | Phe | Leu | Gln | His | Lys | Asp | Asp | Asn | Pro | Asn | Leu |
| | | | 100 | | | | | 105 | | | | | 110 | | |
| Pro | Arg | Leu | Val | Arg | Pro | Glu | Val | Asp | Val | Met | Cys | Thr | Ala | Phe | His |
| | | 115 | | | | | 120 | | | | | 125 | | | |
| Asp | Asn | Glu | Glu | Thr | Phe | Leu | Lys | Lys | Tyr | Leu | Tyr | Glu | Ile | Ala | Arg |
| 130 | | | | | 135 | | | | | 140 | | | | | |
| Arg | His | Pro | Tyr | Phe | Tyr | Ala | Pro | Glu | Leu | Leu | Phe | Phe | Ala | Lys | Arg |
| 145 | | | | | 150 | | | | | 155 | | | | | 160 |
| Tyr | Lys | Ala | Ala | Phe | Thr | Glu | Cys | Cys | Gln | Ala | Ala | Asp | Lys | Ala | Ala |
| | | | | 165 | | | | | 170 | | | | | 175 | |
| Cys | Leu | Leu | Pro | Lys | Leu | Asp | Glu | Leu | Arg | Asp | Glu | Gly | Lys | Ala | Ser |
| | | | 180 | | | | | 185 | | | | | 190 | | |
| Ser | Ala | Lys | Gln | Arg | Leu | Lys | Cys | Ala | Ser | Leu | Gln | Lys | Phe | Gly | Glu |
| | | 195 | | | | | 200 | | | | | 205 | | | |
| Arg | Ala | Phe | Lys | Ala | Trp | Ala | Val | Ala | Arg | Leu | Ser | Gln | Arg | Phe | Pro |
| | 210 | | | | | 215 | | | | | 220 | | | | |
| Lys | Ala | Glu | Phe | Ala | Glu | Val | Ser | Lys | Leu | Val | Thr | Asp | Leu | Thr | Lys |
| 225 | | | | | 230 | | | | | 235 | | | | | 240 |
| Val | His | Thr | Glu | Cys | Cys | His | Gly | Asp | Leu | Leu | Glu | Cys | Ala | Asp | Asp |
| | | | | 245 | | | | | 250 | | | | | 255 | |
| Arg | Ala | Asp | Leu | Ala | Lys | Tyr | Ile | Cys | Glu | Asn | Gln | Asp | Ser | Ile | Ser |
| | | | 260 | | | | | 265 | | | | | 270 | | |
| Ser | Lys | Leu | Lys | Glu | Cys | Cys | Glu | Lys | Pro | Leu | Leu | Glu | Lys | Ser | His |
| | | 275 | | | | | 280 | | | | | 285 | | | |
| Cys | Ile | Ala | Glu | Val | Glu | Asn | Asp | Glu | Met | Pro | Ala | Asp | Leu | Pro | Ser |
| | 290 | | | | | 295 | | | | | 300 | | | | |
| Leu | Ala | Ala | Asp | Phe | Val | Glu | Ser | Lys | Asp | Val | Cys | Lys | Asn | Tyr | Ala |
| 305 | | | | | 310 | | | | | 315 | | | | | 320 |
| Glu | Ala | Lys | Asp | Val | Phe | Leu | Gly | Met | Phe | Leu | Tyr | Glu | Tyr | Ala | Arg |

```
            325                 330                 335
Arg His Pro Asp Tyr Ser Val Val Leu Leu Arg Leu Ala Lys Thr
            340                 345                 350
Tyr Glu Thr Thr Leu Glu Lys Cys Cys Ala Ala Ala Asp Pro His Glu
            355                 360                 365
Cys Tyr Ala Lys Val Phe Asp Glu Phe Lys Pro Leu Val Glu Glu Pro
            370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
            405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
            435                 440                 445
Ala Glu Asp Tyr Leu Ser Val Val Leu Asn Gln Leu Cys Val Leu His
            450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
            485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
            530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
            565                 570                 575
Ala
```

<210> SEQ ID NO 104
<211> LENGTH: 584
<212> TYPE: PRT
<213> ORGANISM: Artificial Sequence
<220> FEATURE:
<223> OTHER INFORMATION: Synthetic polypeptide

<400> SEQUENCE: 104

```
Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
            20                  25                  30
Gln Cys Pro Phe Glu Asp His Val Lys Leu Val Asn Glu Val Thr Glu
            35                  40                  45
Phe Ala Lys Thr Cys Val Ala Asp Glu Ser Ala Glu Asn Cys Asp Lys
            50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
            85                  90                  95
Glu Arg Asn Glu Cys Phe Leu Gln His Lys Asp Asp Asn Pro Asn Leu
            100                 105                 110
```

```
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
                180                 185                 190
Ser Ala Lys Gln Arg Leu Lys Cys Ala Ser Leu Gln Lys Phe Gly Glu
            195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
        260                 265                 270
Ser Lys Leu Lys Glu Cys Cys Glu Lys Pro Leu Leu Glu Lys Ser His
    275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
        340                 345                 350
Tyr Glu Thr Thr Leu Glu Lys Cys Cys Ala Ala Ala Asp Pro His Glu
    355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
    435                 440                 445
Ala Glu Asp Tyr Leu Ser Val Val Leu Asn Gln Leu Cys Val Leu His
450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
```

```
Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly
            580

<210> SEQ ID NO 105
<211> LENGTH: 586
<212> TYPE: PRT
<213> ORGANISM: Artificial Sequence
<220> FEATURE:
<223> OTHER INFORMATION: Synthetic polypeptide

<400> SEQUENCE: 105

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300
```

```
Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly
            580                 585

<210> SEQ ID NO 106
<211> LENGTH: 602
<212> TYPE: PRT
<213> ORGANISM: Artificial Sequence
<220> FEATURE:
<223> OTHER INFORMATION: Synthetic polypeptide

<400> SEQUENCE: 106

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80
```

```
Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
```

```
                500                 505                 510
Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Gly Gly
            580                 585                 590

Gly Gly Ser Gly Gly Gly Gly Ser Ala Arg
        595                 600

<210> SEQ ID NO 107
<211> LENGTH: 603
<212> TYPE: PRT
<213> ORGANISM: Artificial Sequence
<220> FEATURE:
<223> OTHER INFORMATION: Synthetic polypeptide

<400> SEQUENCE: 107

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65              70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
```

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu Gly Gly Gly Ser Gly Gly Gly
            580                 585                 590

Gly Gly Ser Gly Gly Gly Gly Ser Ala Arg Asn
            595                 600

<210> SEQ ID NO 108
<211> LENGTH: 405
<212> TYPE: DNA
<213> ORGANISM: Artificial Sequence
<220> FEATURE:
<223> OTHER INFORMATION: Synthetic oligonucleotide

<400> SEQUENCE: 108
atggacatga gggtccccgc tcagctcctg gggctcctgc tactctggct ccgaggtgcc      60
agatgtgcgc gcaacgggac tcactgtccg ctcgggcccg ggcgttgctg ccgtctgcac     120

|  |  |
|---|---|
| acggtcaacg cgtcgctgga agacctgggc tgggccgatt gggtgctgtc gccacgggag | 180 |
| gtgcaagtga ccatgtgcat cggcgcgtgc ccgagccagt tccgggcggc aaacatgcac | 240 |
| gcgcagatca agacgagcct gcaccgcctg aagcccgaca cggtgccagc gccctgctgc | 300 |
| gtgcccgcca gctacaatcc catggtgctc attcaaaaga ccgacaccgg ggtgtcgctc | 360 |
| cagacctatg atgacttgtt agccaaagac tgccactgca tatga | 405 |

<210> SEQ ID NO 109
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 109

|  |  |
|---|---|
| atggacatga gggtccccgc tcagctcctg gggctcctgc tactctggct ccgaggtgcc | 60 |
| agatgtgcgc gcaacgggga ccactgtccg ctcgggcccg ggcgttgctg caatctgacc | 120 |
| acggtccgcg cgtcgctgga agacctgggc tgggccgatt gggtgctgtc gccacgggag | 180 |
| gtgcaagtga ccatgtgcat cggcgcgtgc ccgagccagt tccgggcggc aaacatgcac | 240 |
| gcgcagatca agacgagcct gcaccgcctg aagcccgaca cggtgccagc gccctgctgc | 300 |
| gtgcccgcca gctacaatcc catggtgctc attcaaaaga ccgacaccgg ggtgtcgctc | 360 |
| cagacctatg atgacttgtt agccaaagac tgccactgca tatga | 405 |

<210> SEQ ID NO 110
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 110

|  |  |
|---|---|
| atggacatga gggtccccgc tcagctcctg gggctcctgc tactctggct ccgaggtgcc | 60 |
| agatgtgcgc gcaacgggga ccactgtccg ctcgggcccg ggcgttgctg ccgtctgcac | 120 |
| acggtccgcg cgaacctgac ggacctgggc tgggccgatt gggtgctgtc gccacgggag | 180 |
| gtgcaagtga ccatgtgcat cggcgcgtgc ccgagccagt tccgggcggc aaacatgcac | 240 |
| gcgcagatca agacgagcct gcaccgcctg aagcccgaca cggtgccagc gccctgctgc | 300 |
| gtgcccgcca gctacaatcc catggtgctc attcaaaaga ccgacaccgg ggtgtcgctc | 360 |
| cagacctatg atgacttgtt agccaaagac tgccactgca tatga | 405 |

<210> SEQ ID NO 111
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 111

|  |  |
|---|---|
| atggacatga gggtccccgc tcagctcctg gggctcctgc tactctggct ccgaggtgcc | 60 |
| agatgtgcgc gcaacgggga ccactgtccg ctcgggcccg ggcgttgctg ccgtctgcac | 120 |
| acggtccgcg cgtcgaatga aaccctgggc tgggccgatt gggtgctgtc gccacgggag | 180 |
| gtgcaagtga ccatgtgcat cggcgcgtgc ccgagccagt tccgggcggc aaacatgcac | 240 |
| gcgcagatca agacgagcct gcaccgcctg aagcccgaca cggtgccagc gccctgctgc | 300 |
| gtgcccgcca gctacaatcc catggtgctc attcaaaaga ccgacaccgg ggtgtcgctc | 360 |

```
cagacctatg atgacttgtt agccaaagac tgccactgca tatga              405

<210> SEQ ID NO 112
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 112
atggacatga gggtccccgc tcagctcctg gggctcctgc tactctggct ccgaggtgcc    60
agatgtgcgc gcaacgggga ccactgtccg ctcgggcccg ggcgttgctg ccgtctgcac   120
acggtccgcg cgtcgctgga agacctgggc tgggccgatt gggtgctgtc gccacgggag   180
gtgcaagtga ccatgtgcat cggcgcgtgc ccgaaccaga cccgggcggc aaacatgcac   240
gcgcagatca agacgagcct gcaccgcctg aagcccgaca cggtgccagc gccctgctgc   300
gtgcccgcca gctacaatcc catggtgctc attcaaaaga ccgacaccgg ggtgtcgctc   360
cagacctatg atgacttgtt agccaaagac tgccactgca tatga              405

<210> SEQ ID NO 113
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 113
atggacatga gggtccccgc tcagctcctg gggctcctgc tactctggct ccgaggtgcc    60
agatgtgcgc gcaacgggga ccactgtccg ctcgggcccg ggcgttgctg ccgtctgcac   120
acggtccgcg cgtcgctgga agacctgggc tgggccgatt gggtgctgtc gccacgggag   180
gtgcaagtga ccatgtgcat cggcgcgtgc ccgagcaact tcacggcggc aaacatgcac   240
gcgcagatca agacgagcct gcaccgcctg aagcccgaca cggtgccagc gccctgctgc   300
gtgcccgcca gctacaatcc catggtgctc attcaaaaga ccgacaccgg ggtgtcgctc   360
cagacctatg atgacttgtt agccaaagac tgccactgca tatga              405

<210> SEQ ID NO 114
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 114
atggacatga gggtccccgc tcagctcctg gggctcctgc tactctggct ccgaggtgcc    60
agatgtgcgc gcaacgggga ccactgtccg ctcgggcccg ggcgttgctg ccgtctgcac   120
acggtccgcg cgtcgctgga agacctgggc tgggccgatt gggtgctgtc gccacgggag   180
gtgcaagtga ccatgtgcat cggcgcgtgc ccgagccaga accggacggc aaacatgcac   240
gcgcagatca agacgagcct gcaccgcctg aagcccgaca cggtgccagc gccctgctgc   300
gtgcccgcca gctacaatcc catggtgctc attcaaaaga ccgacaccgg ggtgtcgctc   360
cagacctatg atgacttgtt agccaaagac tgccactgca tatga              405

<210> SEQ ID NO 115
<211> LENGTH: 405
<212> TYPE: DNA
```

<213> ORGANISM: Artificial sequence
<220> FEATURE:
<223> OTHER INFORMATION: Synthetic oligonucleotide

<400> SEQUENCE: 115

```
atggacatga gggtccccgc tcagctcctg gggctcctgc tactctggct ccgaggtgcc      60
agatgtgcgc gcaacgggga ccactgtccg ctcgggcccg ggcgttgctg ccgtctgcac     120
acggtccgcg cgtcgctgga agacctgggc tgggccgatt gggtgctgtc gccacgggag     180
gtgcaagtga ccatgtgcat cggcgcgtgc ccgagccagt tcaacgcgac gaacatgcac     240
gcgcagatca agacgagcct gcaccgcctg aagcccgaca cggtgccagc gccctgctgc     300
gtgcccgcca gctacaatcc catggtgctc attcaaaaga ccgacaccgg ggtgtcgctc     360
cagacctatg atgacttgtt agccaaagac tgccactgca tatga                     405
```

<210> SEQ ID NO 116
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 116

```
atggacatga gggtccccgc tcagctcctg gggctcctgc tactctggct ccgaggtgcc      60
agatgtgcgc gcaacgggga ccactgtccg ctcgggcccg ggcgttgctg ccgtctgcac     120
acggtccgcg cgtcgctgga agacctgggc tgggccgatt gggtgctgtc gccacgggag     180
gtgcaagtga ccatgtgcat cggcgcgtgc ccgagccagt tccgggcggc aaacatgcac     240
gcgcagatca agacgaacct gacgcgcctg aagcccgaca cggtgccagc gccctgctgc     300
gtgcccgcca gctacaatcc catggtgctc attcaaaaga ccgacaccgg ggtgtcgctc     360
cagacctatg atgacttgtt agccaaagac tgccactgca tatga                     405
```

<210> SEQ ID NO 117
<211> LENGTH: 402
<212> TYPE: DNA
<213> ORGANISM: Artificial sequence
<220> FEATURE:
<223> OTHER INFORMATION: Synthetic oligonucleotide

<400> SEQUENCE: 117

```
atggacatga gggtccccgc tcagctcctg gggctcctgc tactctggct ccgaggtgcc      60
agatgtgcgc gcaacgggga ccactgtccg ctcgggcccg ggcgttgctg ccgtctgcac     120
acggtccgcg cgtcgctgga agacctgggc tgggccgatt gggtgctgtc gccacgggag     180
gtgcaagtga ccatgtgcat cggcgcgtgc ccgagccagt tccgggcggc aaacatgcac     240
gcgcagatca agacgagcaa ccacaccctg aagcccgaca cggtgccagc gccctgctgc     300
gtgcccgcca gctacaatcc catggtgctc attcaaaaga ccgacaccgg ggtgtcgctc     360
cagacctatg atgacttgtt agccaaagac tgccactgca ta                        402
```

<210> SEQ ID NO 118
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 118

```
atggacatga gggtccccgc tcagctcctg gggctcctgc tactctggct ccgaggtgcc      60
```

```
agatgtgcgc gcaacgggga ccactgtccg ctcgggcccg ggcgttgctg ccgtctgcac      120
acggtccgcg cgtcgctgga agacctgggc tgggccgatt gggtgctgtc gccacgggag      180
gtgcaagtga ccatgtgcat cggcgcgtgc ccgagccagt tccgggcggc aaacatgcac      240
gcgcagatca agacgagcct gcaccgcctg aagcccgaca cggtgccagc gccctgctgc      300
gtgcccgcca actacactcc catggtgctc attcaaaaga ccgacaccgg ggtgtcgctc      360
cagacctatg atgacttgtt agccaaagac tgccactgca tatga                     405
```

<210> SEQ ID NO 119
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 119

```
atggacatga gggtccccgc tcagctcctg gggctcctgc tactctggct ccgaggtgcc       60
agatgtgcgc gcaacgggga ccactgtccg ctcgggcccg ggcgttgctg ccgtctgcac      120
acggtccgcg cgtcgctgga agacctgggc tgggccgatt gggtgctgtc gccacgggag      180
gtgcaagtga ccatgtgcat cggcgcgtgc ccgagccagt tccgggcggc aaacatgcac      240
gcgcagatca agacgagcct gcaccgcctg aagcccgaca cggtgccagc gccctgctgc      300
gtgcccgcca gctacaatcc catggtgctc attcaaaaca ccaccaccgg ggtgtcgctc      360
cagacctatg atgacttgtt agccaaagac tgccactgca tatga                     405
```

<210> SEQ ID NO 120
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 120

```
atggacatga gggtccccgc tcagctcctg gggctcctgc tactctggct ccgaggtgcc       60
agatgtgcgc gcaacgggga ccactgtccg ctcgggcccg ggcgttgctg ccgtctgcac      120
acggtccgcg cgtcgctgga agacctgggc tgggccgatt gggtgctgtc gccacgggag      180
gtgcaagtga ccatgtgcat cggcgcgtgc ccgagccagt tccgggcggc aaacatgcac      240
gcgcagatca agacgagcct gcaccgcctg aagcccgaca cggtgccagc gccctgctgc      300
gtgcccgcca gctacaatcc catggtgctc attcaaaaga ccaacaccac ggtgtcgctc      360
cagacctatg atgacttgtt agccaaagac tgccactgca tatga                     405
```

<210> SEQ ID NO 121
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 121

```
atggacatga gggtccccgc tcagctcctg gggctcctgc tactctggct ccgaggtgcc       60
agatgtgcgc gcaacgggga ccactgtccg ctcgggcccg ggcgttgctg ccgtctgcac      120
acggtccgcg cgtcgctgga agacctgggc tgggccgatt gggtgctgtc gccacgggag      180
gtgcaagtga ccatgtgcat cggcgcgtgc ccgagccagt tccgggcggc aaacatgcac      240
```

```
gcgcagatca agacgagcct gcaccgcctg aagcccgaca cggtgccagc gccctgctgc    300
gtgcccgcca gctacaatcc catggtgctc attcaaaaga ccgacaacgg gacgtcgctc    360
cagacctatg atgacttgtt agccaaagac tgccactgca tatga                    405
```

```
<210> SEQ ID NO 122
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 122
atggacatga gggtccccgc tcagctcctg gggctcctgc tactctggct ccgaggtgcc     60
agatgtgcgc gcaacgggga ccactgtccg ctcgggcccg ggcgttgctg ccgtctgcac    120
acggtccgcg cgtcgctgga agacctgggc tgggccgatt gggtgctgtc gccacgggag    180
gtgcaagtga ccatgtgcat cggcgcgtgc ccgagccagt tccgggcggc aaacatgcac    240
gcgcagatca agacgagcct gcaccgcctg aagcccgaca cggtgccagc gccctgctgc    300
gtgcccgcca gctacaatcc catggtgctc attcaaaaga ccgacaccgg gaactcgacc    360
cagacctatg atgacttgtt agccaaagac tgccactgca tatga                    405
```

```
<210> SEQ ID NO 123
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 123
atggacatga gggtccccgc tcagctcctg gggctcctgc tactctggct ccgaggtgcc     60
agatgtgcgc gcaacgggga ccactgtccg ctcgggcccg ggcgttgctg ccgtctgcac    120
acggtccgcg cgtcgctgga agacctgggc tgggccgatt gggtgctgtc gccacgggag    180
gtgcaagtga ccatgtgcat cggcgcgtgc ccgagccagt tccgggcggc aaacatgcac    240
gcgcagatca agacgagcct gcaccgcctg aagcccgaca cggtgccagc gccctgctgc    300
gtgcccgcca gctacaatcc catggtgctc attcaaaaga ccgacaccgg ggtgaacctc    360
acgacctatg atgacttgtt agccaaagac tgccactgca tatga                    405
```

```
<210> SEQ ID NO 124
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 124
atggacatga gggtccccgc tcagctcctg gggctcctgc tactctggct ccgaggtgcc     60
agatgtgcgc gcaacgggga ccactgtccg ctcgggcccg ggcgttgctg ccgtctgcac    120
acggtccgcg cgtcgctgga agacctgggc tgggccgatt gggtgctgtc gccacgggag    180
gtgcaagtga ccatgtgcat cggcgcgtgc ccgagccagt tccgggcggc aaacatgcac    240
gcgcagatca agacgagcct gcaccgcctg aagcccgaca cggtgccagc gccctgctgc    300
gtgcccgcca gctacaatcc catggtgctc attcaaaaga ccgacaccgg ggtgtcgctc    360
cagacctatg atgacttgtt aaacaaaacc tgccactgca tatga                    405
```

<210> SEQ ID NO 125
<211> LENGTH: 396
<212> TYPE: DNA
<213> ORGANISM: Artificial sequence
<220> FEATURE:
<223> OTHER INFORMATION: Synthetic oligonucleotide

<400> SEQUENCE: 125

```
atggacatga gggtccccgc tcagctcctg gggctcctgc tactctggct ccgaggtgcc      60
agatgtgggg accactgtcc gctcgggccc ggcgttgct gccgtctgca cacggtccgc     120
gcgtcgctgg aagacctggg ctgggccgat tgggtgctgt cgccacggga ggtgcaagtg    180
accatgtgca tcggcgcgtg cccgagccag ttccgggcgg caaacatgca cgcgcagatc    240
aagacgagcc tgcaccgcct gaagcccgac acggtgccag cgcctgctg cgtgcccgcc     300
agctacaatc ccatggtgct cattcaaaac accaccaccg gggtgtcgct ccagacctat    360
gatgacttgt tagccaaaga ctgccactgc atatga                              396
```

<210> SEQ ID NO 126
<211> LENGTH: 134
<212> TYPE: PRT
<213> ORGANISM: Artificial Sequence
<220> FEATURE:
<223> OTHER INFORMATION: Synthetic polypeptide

<400> SEQUENCE: 126

```
Met Asp Met Arg Val Pro Ala Gln Leu Leu Gly Leu Leu Leu Leu Trp
1               5                   10                  15
Leu Arg Gly Ala Arg Cys Ala Arg Asn Gly Asp His Cys Pro Leu Gly
            20                  25                  30
Pro Gly Arg Cys Cys Arg Leu His Thr Val Arg Ala Ser Leu Glu Asp
        35                  40                  45
Leu Gly Trp Ala Asp Trp Val Leu Ser Pro Arg Glu Val Gln Val Thr
    50                  55                  60
Met Cys Ile Gly Ala Cys Pro Ser Gln Phe Arg Ala Ala Asn Met His
65                  70                  75                  80
Ala Gln Ile Lys Thr Ser Leu His Arg Leu Lys Pro Asp Thr Val Pro
                85                  90                  95
Ala Pro Cys Cys Val Pro Ala Ser Tyr Asn Pro Met Val Leu Ile Gln
            100                 105                 110
Lys Thr Asp Thr Gly Val Ser Leu Gln Thr Tyr Asp Asp Leu Leu Ala
        115                 120                 125
Lys Asp Cys His Cys Ile
    130
```

<210> SEQ ID NO 127
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 127

```
atggacatga gggtccccgc tcagctcctg gggctcctgc tactctggct ccgaggtgcc      60
agatgtgcgc gcaacgggga ccactgtccg ctcgggcccg gcgttgctg ccgtctgcac     120
acggtccgcg cgtcgctgga agacctgggc tgggccgatt gggtgctgtc gccacgggag    180
gtgcaagtga ccatgtgcat cggcgcgtgc ccgagccagt tccgggcggc aaacatgcac    240
gcgcagatca agacgagcct gcaccgcctg aagcccgaca cggtgccagc gcctgctgc     300
```

```
gtgcccgcca gctacaatcc catggtgctc attcaaaaga ccgacaccgg ggtgtcgctc    360
cagacctatg atgacttgtt agccaaagac tgccactgca tatga                   405
```

COMPOSITIONS AND METHODS OF USE FOR TREATING METABOLIC DISORDERS

CROSS-REFERENCE TO RELATED APPLICATIONS

This application claims priority benefit of U.S. provisional application Ser. No. 62/031,063, filed on Jul. 30, 2014 and U.S. provisional application Ser. No. 62/195,908 filed on Jul. 23, 2015, which applications are incorporated herein by reference in their entirety.

INCORPORATION BY REFERENCE OF SEQUENCE LISTING PROVIDED AS A TEXT FILE

A Sequence Listing is provided herewith as a text file, "NGMB-139_SeqList.txt" created on Jul. 22, 2015 and having a size of 133 KB. The contents of the text file are incorporated by reference herein in their entirety.

FIELD OF THE INVENTION

The present invention relates to, among other things, polypeptides and compositions thereof which are useful in treating metabolism related conditions.

INTRODUCTION

Obesity is most commonly caused by excessive food intake coupled with limited energy expenditure and/or lack of physical exercise. Obesity increases the likelihood of development of various diseases, such as diabetes mellitus, hypertension, atherosclerosis, coronary artery disease, sleep apnea, gout, rheumatism and arthritis. Moreover, mortality risk directly correlates with obesity, such that, for example, a body-mass index in excess of 40 results in an average decreased life expectancy of more than 10 years.

Current pharmacological treatment modalities include appetite suppressors targeting receptor classes (e.g., CB1, 5-HT$_{2C}$, and NPY); regulators of the appetite circuits in the hypothalamus and the molecular actions of ghrelin; and nutrient-absorption inhibitors targeting lipases. Unfortunately, none of the current modalities has been shown to effectively treat obesity without causing adverse effects, some of which can be very severe.

High blood glucose levels stimulate the secretion of insulin by pancreatic beta-cells. Insulin in turn stimulates the entry of glucose into muscles and adipose cells, leading to the storage of glycogen and triglycerides and to the synthesis of proteins. Activation of insulin receptors on various cell types diminishes circulating glucose levels by increasing glucose uptake and utilization, and by reducing hepatic glucose output. Disruptions within this regulatory network can result in diabetes and associated pathologic syndromes that affect a large and growing percentage of the human population.

Patients who have a glucose metabolism disorder can suffer from hyperglycemia, hyperinsulinemia, and/or glucose intolerance. An example of a disorder that is often associated with the aberrant levels of glucose and/or insulin is insulin resistance, in which liver, fat, and muscle cells lose their ability to respond to normal blood insulin levels.

In view of the prevalence and severity of obesity, diabetes and associated metabolic and non-metabolic disorders, treatment modalities that modulate, for example, appetite, glucose and/or insulin levels and enhance the biological response to fluctuating glucose levels in a patient remain of interest.

Wild type GDF15, also known as MIC-1 (macrophage inhibitory cytokine-1) has been linked to regulation of body weight (Tsai V W, et al., PLoS One 2013; 8 (2): e55174; U.S. Pat. No. 8,192,735).

SUMMARY

Polypeptides having a contiguous amino acid sequence that is at least 90% identical to the amino acid sequence of mature wild type human GDF15 (SEQ ID NO: 1) are provided. Polypeptides of the present disclosure encompass GDF15 muteins, modified GDF15, and modified GDF15 muteins. Compositions of these polypeptide are also provided. The present disclosure contemplates the use of the polypeptides described herein, and compositions thereof, in treating or preventing body weight related disorders and/or glucose metabolism disorders.

As noted above, a polypeptide that includes a contiguous amino acid sequence that is at least 90% identical to the amino acid sequence of SEQ ID NO: 1 is provided. The contiguous amino acid sequence includes at least one of the following pairs of substitutions of the corresponding amino acids in SEQ ID NO: 1: i) D5T/S and R21N; ii) R16N and H18T/S; iii) S23N and E25T/S; iv) L24N and D26T/S; v) S50N and F52T/S or F52N and A54T/S; vi) Q51N and R53T/S or R53N and A55T/S; vi) S64N and H66T/S; vii) L65N and R67T/S; viii) S82N and N84T/S; ix) K91N and D93T/S or D93N and G95T/S; x) T94N and V96T/S or V96N and L98T/S; xi) S97N and Q99T/S; and xii) A106N and D108T/S.

For example, the contiguous amino acid sequence may include at least one of the following pairs of substitutions of the corresponding amino acids in SEQ ID NO: 1: i) D5T and R21N or D5S and R21N; ii) R16N and H18T or R16N and H18S ; iii) S23N and E25T or S23N and E25S; iv) L24N and D26T or L24N and D26S; v) S50N and F52T; S50N and F52S; F52N and A54T; or F52N and A54S; vi) Q51N and R53T; Q51N and R53S; R53N and A55T; or R53N and A55S; vi) S64N and H66T or S64N and H66S; vii) L65N and R67T or L65N and R67S; viii) S82N and N84T or S82N and N84S; ix) K91N and D93T; K91N and D93S; D93N and G95T; or D93N and G95S; x) T94N and V96T; T94N and V96S; V96N and L98T; or V96N and L98S; xi) S97N and Q99T or S97N and Q99S; and xii) A106N and D108T or A106N and D108S.

In certain embodiments, the polypeptide may include at least one of the following pairs of substitutions of the corresponding amino acids in SEQ ID NO: 1: D5T and R21N; S23N and E25T/S; R53N and A55T/S; S64N and H66T/S; K91N and D93T/S; D93N and G95T/S; S97N and Q99T/S; and A106N and D108T/S.

In certain embodiments, the polypeptide may include at least one of the following pairs of substitutions of the corresponding amino acids in SEQ ID NO: 1: D5T and R21N; D5S and R21N; S23N and E25T; S23N and E25S; R53N and A55T; R53N and A55S; S64N and H66T; S64N and H66S; K91N and D93T; K91N and D93S; D93N and G95T; D93N and G95S; S97N and Q99T; S97N and Q99S; A106N and D108T; and A106N and D108S.

In certain embodiments, the polypeptide may include at least one of the following pairs of substitutions of the corresponding amino acids in SEQ ID NO: 1: D5T and R21N; S64N and H66T/S; K91N and D93T/S; D93N and G95T/S; and S97N and Q99T/S.

In other embodiments, the polypeptide may include at least one of the following pairs of substitutions of the corresponding amino acids in SEQ ID NO: 1: K91N and D93T or K91N and D93S; and D93N and G95T or D93N and G95S. In other embodiments, the polypeptide may include the following pair of substitutions of the corresponding amino acids in SEQ ID NO: 1: K91N and D93T.

In exemplary embodiments, the contiguous amino acid sequence may be at least 95% identical to the amino acid sequence of SEQ ID NO: 1.

In other embodiments, the contiguous amino acid sequence may be at least 98 amino acids long and may be at least 90% identical to the amino acid sequence of SEQ ID NO: 1, where the C-terminal amino acid of the polypeptide corresponds to Isoleucine at position 112 in SEQ ID NO: 1.

In other embodiments, the contiguous amino acid sequence may be at least 98 amino acids long and may be at least 95% identical to the amino acid sequence of SEQ ID NO: 1, where the C-terminal amino acid of the polypeptide corresponds to Isoleucine at position 112 in SEQ ID NO: 1.

Exemplary polypeptides disclosed herein include a contiguous amino acid sequence that is at least 98 amino acids long, at least 90% identical to the amino acid sequence of SEQ ID NO: 1, and have deletions of amino acids relative to SEQ ID NO: 1. For example, the polypeptides may have an N-terminal truncation relative to SEQ ID NO: 1. The truncation may be of 1, 2, 3, 4, 5, 6, 7, 8, 9, 10, 11, 12, 13, 14 or more amino acids relative to SEQ ID NO: 1, e.g., 1-14 amino acids, 3-14 amino acids, 6-14 amino acids, or 3-6 amino acids.

In certain cases, the contiguous amino acid sequence that is at least 98 amino acids long, at least 90% identical to the amino acid sequence of SEQ ID NO: 1, and does not include the first three amino acids that correspond to the first three amino acids present at the N-terminus of SEQ ID NO: 1, where the C-terminal amino acid corresponds to Isoleucine at position 112 in SEQ ID NO: 1.

In certain cases, the contiguous amino acid sequence is at least 98 amino acids long, at least 90% identical to the amino acid sequence of SEQ ID NO: 1, and does not include the first six amino acids that correspond to the first six amino acids present at the N-terminus of SEQ ID NO: 1, wherein the C-terminal amino acid corresponds to Isoleucine at position 112 in SEQ ID NO: 1.

In certain cases, the contiguous amino acid sequence is at least 98 amino acids long, at least 90% identical to the amino acid sequence of SEQ ID NO: 1, and does not include the first fourteen amino acids that correspond to the first fourteen amino acids present at the N-terminus of SEQ ID NO: 1, wherein the C-terminal amino acid corresponds to Isoleucine at position 112 in SEQ ID NO: 1.

In certain cases, the polypeptide may include a signal sequence at the N-terminus, such as, an IgK signal sequence. The signal sequence may be conjugated to the polypeptide via a linker, which linker may be a cleavable linker.

Also provided herein is a fusion protein that includes contiguously from N-terminus to C-terminus: a heterologous polypeptide-[(G$_4$S)]$_5$-GDF15; a heterologous polypeptide-[(G$_4$S)]$_5$-ΔN3-GDF15; or a heterologous polypeptide-[(G$_4$S)]$_5$-ΔN6-GDF15.

In exemplary embodiments, the heterologous polypeptide may be serum albumin, maltose binding protein, or immunoglobulin Fc polypeptide. The serum albumin may be human serum albumin, cyno serum albumin or bovine serum albumin. The fusion protein may include a signal sequence at the N-terminus. The signal sequence may be an IgK signal sequence.

Also provided herein is a nucleic acid molecule encoding the above described polypeptides or fusion proteins. The nucleic acid molecule may be operably linked to an expression control element that confers expression of the nucleic acid molecule encoding the polypeptide or the fusion protein in vitro or in vivo. A vector that includes the nucleic acid molecule is also contemplated. The vector may be a viral vector.

Some embodiments include transformed or host cells that express one or more of the aforementioned polypeptides.

In particular embodiments of the present disclosure, one or more of the aforementioned polypeptides is formulated to yield a pharmaceutical composition, wherein the composition also includes one or more pharmaceutically acceptable diluents, carriers or excipients. In certain embodiments, a pharmaceutical composition also includes at least one additional prophylactic or therapeutic agent.

Still further embodiments of the present disclosure comprise an antibody that binds specifically to one of the aforementioned mutein polypeptides. In some embodiments, the antibody comprises a light chain variable region and a heavy chain variable region present in separate polypeptides or in a single polypeptide. An antibody of the present disclosure binds the polypeptide with an affinity of from about $10^7$ M$^{-1}$ to about $10^{12}$ M$^{-1}$ in certain embodiments. In still other embodiments, the antibody comprises a heavy chain constant region of the isotype IgG1, IgG2, IgG3, or IgG4. In additional embodiments, the antibody is detectably labeled, while it is a Fv, scFv, Fab, F(ab')$_2$, or Fab' in other embodiments.

The present disclosure also contemplates antibodies that comprise a covalently linked non-polypeptide polymer (e.g., a poly(ethylene glycol) polymer). In other embodiments, the antibody comprises a covalently linked moiety selected from a lipid moiety, a fatty acid moiety, a polysaccharide moiety, and a carbohydrate moiety.

The antibody is a single chain Fv (scFv) antibody in some embodiments, and the scFv is multimerized in others.

The antibodies of the present disclosure may be, but are not limited to, monoclonal antibodies, polyclonal antibodies, or humanized antibodies.

Furthermore, the present disclosure contemplates pharmaceutical compositions comprising an antibody as described above formulated with at least one pharmaceutically acceptable excipient, carrier or diluent. Such pharmaceutical compositions may also contain at least one additional prophylactic or therapeutic agent.

Certain embodiments of the present disclosure contemplate a sterile container that contains one of the above-mentioned pharmaceutical compositions and optionally one or more additional components. By way of example, but not limitation, the sterile container may be a syringe. In still further embodiments, the sterile container is one component of a kit; the kit may also contain, for example, a second sterile container that contains at least one prophylactic or therapeutic agent.

Also disclosed herein is a method of making the aforementioned polypeptides or fusion proteins. The method may include culturing a host cell expressing the polypeptide or the fusion protein; and purifying the expressed polypeptide or fusion protein.

The present disclosure also contemplates a method of treating or preventing a glucose metabolism disorder in a subject (e.g., a human) by administering to the subject a therapeutically effective amount of the aforementioned polypeptide or fusion protein. In some methods, the treating or preventing results in a reduction in plasma glucose in the subject, a reduction in plasma insulin in the subject, a reduction in body weight and/or food intake, or an increase in glucose tolerance in the subject. In particular embodiments, the glucose metabolism disorder is diabetes mellitus.

A method of treating or preventing a body weight disorder in a subject is also disclosed. The method may include administering to the subject the polypeptide or the fusion protein of the present disclosure, wherein the polypeptide or the fusion protein is administered in an amount effective in treating or preventing the body weight disorder in the subject. In some methods, the treating or preventing results in a reduction in body weight and/or food intake in the subject.

In some embodiments, the subject is obese and/or has a body weight disorder.

Though not limited to any particular route of administration or dosing regimen, in some embodiments the administering is by parenteral (e.g., subcutaneous) injection.

BRIEF DESCRIPTION OF THE DRAWINGS

FIG. 1 shows an alignment of amino acid sequence of GDF15 muteins disclosed herein with the amino acid sequence of wild type (WT) mature human GDF15.

FIG. 2 shows an alignment of amino acid sequence of ΔN3-GDF15 muteins disclosed herein with amino acid sequence of WT mature human GDF15. The ΔN3-hGDF15 muteins lack the first 3 amino acids (ARN) present on the N-terminus of mature hGDF15.

FIG. 3 depicts two fusion proteins (contructs M1 and M2) which include contiguously from N-terminus to C-terminus: IgK signal sequence (lower case) (IgK)-human serum albumin amino acid (D25-L609) sequence (HSA)-a non-cleavable (Gly-Gly-Gly-Gly-Ser)$_3$ linker [(G$_4$S)]$_3$ (underlined)-mature human GDF15 amino acid sequence (hGDF15) (Bold). Construct M1 (IgK-HSA-[(G$_4$S)]$_3$-hGDF15) contains full length mature hGDF15 whereas, construct M2 (IgK-HSA-[(G$_4$S)]$_3$-ΔN3-hGDF15) contains ΔN3-hGDF15 in which the first 3 amino acids (ARN) that correspond to the amino acids at the N-terminus of mature hGDF15 are deleted.

FIG. 5 depicts two fusion molecules with human serum albumin amino acid (D25-L609) sequence having an IgK signal sequence (lower case) fused to the N-terminus of the mature human GDF15 amino acid sequence (Bold) through a non-cleavable [(G$_4$S)]$_5$ linker (underlined). Construct M3 (IgK-HSA-[(G$_4$S)]$_5$-ΔN3-hGDF15) contains a 3 amino acid truncation (ΔARN) on the N-terminus of mature hGDF15; whereas construct M4 (IgK-HSA-[(G$_4$S)]$_5$-ΔN6-hGDF15) contains a 6 amino acid truncation (ΔARNGDH) relative to the N-terminus of mature hGDF15.

FIG. 8A depicts the amino acid sequences of mono-glycosylated and di-glycosylated muteins produced by introduction of N-linked glycosylation consensus sites (M5-M21). These sequences include an IgK signal sequence (lower case) fused to the N-terminus of the mature human GDF15 amino acid sequence (Bold). FIG. 8B depicts nucleic acid sequences encoding the amino acid sequences depicted in FIG. 8A. FIG. 8C depicts the amino acid sequence of ΔN3-M16 and nucleic acid sequence encoding ΔN3-M16. FIG. 8D depicts the amino acid sequence of WT-mature human GDF15 amino acid sequence containing IgK signal sequence (IgK-WT-GDF15) and the nucleic acid sequence encoding the IgK-WT-GDF15.

FIG. 9 provides a summary of secretion and dimer formation, along with improvements in relative solubility, for each engineered N-glycosylated human GDF15 mutein set forth in FIG. 8A and for ΔN3-M16.

DETAILED DESCRIPTION

Figure 4:
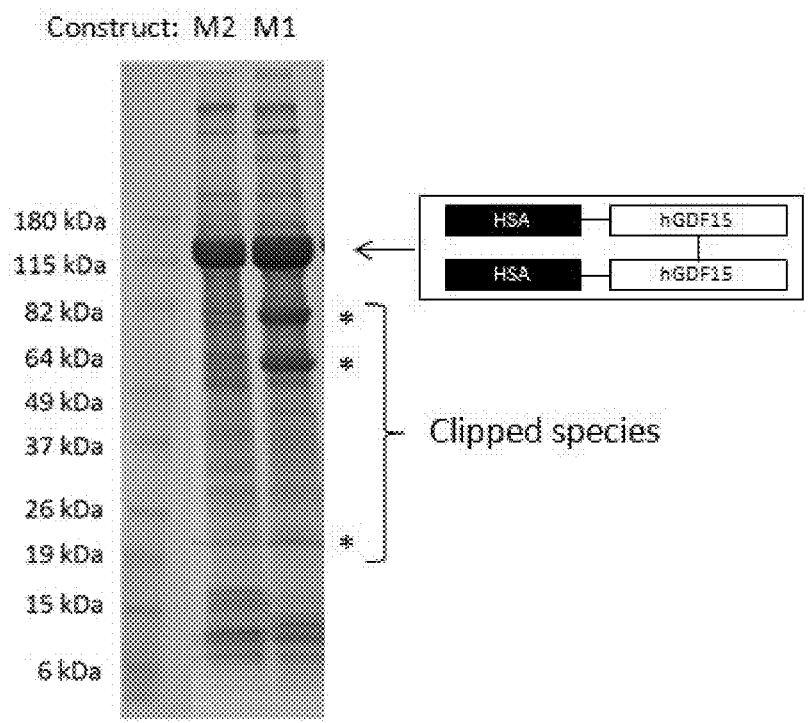
FIG. 4 depicts a non-reduced, coommassie stained, SDS-PAGE expression gel of constructs M1 and M2 from CHOK1SV GSKO stable cell line media. Asterisks (*) denotes clipped species that occur in M1 during secretion from CHOK1SV. LC/MS identification of the clip sites resulted in the design of a stability enhanced construct (M2), which contains a 3 amino acid truncation (ΔARN or ΔN3) on the N-terminus of mature hGDF15.

Before the methods and compositions of the present disclosure are further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. Thus, for example, reference to "the mutant polypeptide" includes reference to one or more mutant polypeptides, and so forth. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "patient" or "subject" are used interchangeably to refer to a human or a non-human animal (e.g., a mammal).

The terms "treat", "treating", treatment" and the like refer to a course of action (such as administering a an agent, e.g., a polypeptide or a pharmaceutical composition comprising a polypeptide) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (i.e., arresting the development or further development of the disease, disorder or condition or clinical symptoms association therewith) an active disease (e.g., so as to decrease the level of insulin and/or glucose in the bloodstream, to increase glucose tolerance so as to minimize fluctuation of glucose levels, and/or so as to protect against diseases caused by disruption of glucose homeostasis).

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an agent, e.g., a polypeptide or a pharmaceutical composition comprising a polypeptide) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to a patient. The therapeutically effective amount can be ascertained by measuring relevant physiological effects. For example, in the case of a hyperglycemic condition, a lowering or reduction of blood glucose or an improvement in glucose tolerance test can be used to determine whether the amount of an agent is effective to treat the hyperglycemic condition. For example, a therapeutically effective amount is an amount sufficient to reduce or decrease any level (e.g., a baseline level) of fasting plasma glucose (FPG), wherein, for example, the amount is sufficient to reduce a FPG level greater than 200 mg/dl to less than 200 mg/dl, wherein the amount is sufficient to reduce a FPG level between 175 mg/dl and 200 mg/dl to less than the starting level, wherein the amount is sufficient to reduce a FPG level between 150 mg/dl and 175 mg/dl to less than the starting level, wherein the amount is sufficient to reduce a FPG level between 125 mg/dl and 150 mg/dl to less than the starting level, and so on (e.g., reducing FPG levels to less than 125 mg/dl, to less than 120 mg/dl, to less than 115 mg/dl, to less than 110 mg/dl, etc.). In the case of HbAlc levels, the effective amount is an amount sufficient to reduce or decrease levels by more than about 10% to 9%, by more than about 9% to 8%, by more than about 8% to 7%, by more than about 7% to 6%, by more than about 6% to 5%, and so on. More particularly, a reduction or decrease of HbAlc levels by about 0.1%, 0.25%, 0.4%, 0.5%, 0.6%, 0.7%, 0.8%, 0.9%, 1%, 1.5%, 2%, 3%, 4%, 5%, 10%, 20%, 30%, 33%, 35%, 40%, 45%, 50%, or more is contemplated by the present disclosure. The therapeutically effective amount can be adjusted in connection with the dosing regimen and diagnostic analysis of the subject's condition and the like.

The phrase "in a sufficient amount to effect a change" means that there is a detectable difference between a level of an indicator measured before (e.g., a baseline level) and after administration of a particular therapy. Indicators include any objective parameter (e.g., level of glucose or insulin or food intake) or subjective parameter (e.g., a subject's feeling of well-being or appetite).

The phrase "glucose tolerance", as used herein, refers to the ability of a subject to control the level of plasma glucose and/or plasma insulin when glucose intake fluctuates. For example, glucose tolerance encompasses the subject's ability to reduce, within about 120 minutes, the level of plasma glucose back to a level determined before the intake of glucose.

The terms "diabetes" and "diabetic" refer to a progressive disease of carbohydrate metabolism involving inadequate production or utilization of insulin, frequently characterized by hyperglycemia and glycosuria. The terms "pre-diabetes" and "pre-diabetic" refer to a state wherein a subject does not have the characteristics, symptoms and the like typically observed in diabetes, but does have characteristics, symptoms and the like that, if left untreated, may progress to diabetes. The presence of these conditions may be determined using, for example, either the fasting plasma glucose (FPG) test or the oral glucose tolerance test (OGTT). Both usually require a subject to fast for at least 8 hours prior to initiating the test. In the FPG test, a subject's blood glucose is measured after the conclusion of the fasting; generally, the subject fasts overnight and the blood glucose is measured in the morning before the subject eats. A healthy subject would generally have a FPG concentration between about 90 and about 100 mg/dl, a subject with "pre-diabetes" would generally have a FPG concentration between about 100 and about 125 mg/dl, and a subject with "diabetes" would generally have a FPG level above about 126 mg/dl. In the OGTT, a subject's blood glucose is measured after fasting and again two hours after drinking a glucose-rich beverage. Two hours after consumption of the glucose-rich beverage, a healthy subject generally has a blood glucose concentration below about 140 mg/dl, a pre-diabetic subject generally has a blood glucose concentration about 140 to about 199 mg/dl, and a diabetic subject generally has a blood glucose concentration about 200 mg/dl or above. While the aforementioned glycemic values pertain to human subjects, normoglycemia, moderate hyperglycemia and overt hyperglycemia are scaled differently in murine subjects. A healthy murine subject after a four-hour fast would generally have a FPG concentration between about 100 and about 150 mg/dl, a murine subject with "pre-diabetes" would generally have a FPG concentration between about 175 and about 250 mg/dl and a murine subject with "diabetes" would generally have a FPG concentration above about 250 mg/dl.

The term "insulin resistance" as used herein refers to a condition where a normal amount of insulin is unable to produce a normal physiological or molecular response. In some cases, a hyper-physiological amount of insulin, either endogenously produced or exogenously administered, is able to overcome the insulin resistance, in whole or in part, and produce a biologic response.

The term "metabolic syndrome" refers to an associated cluster of traits that includes, but is not limited to, hyperinsulinemia, abnormal glucose tolerance, obesity, redistribution of fat to the abdominal or upper body compartment, hypertension, dysfibrinolysis, and dyslipidemia characterized by high triglycerides, low high density lipoprotein (HDL)-cholesterol, and high small dense low density lipoprotein (LDL) particles. Subjects having metabolic syndrome are at risk for development of Type 2 diabetes and/or other disorders (e.g., atherosclerosis).

The phrase "glucose metabolism disorder" encompasses any disorder characterized by a clinical symptom or a combination of clinical symptoms that is associated with an elevated level of glucose and/or an elevated level of insulin in a subject relative to a healthy individual. Elevated levels of glucose and/or insulin may be manifested in the following diseases, disorders and conditions: hyperglycemia, type II diabetes, gestational diabetes, type I diabetes, insulin resistance, impaired glucose tolerance, hyperinsulinemia, impaired glucose metabolism, pre-diabetes, other metabolic disorders (such as metabolic syndrome, which is also referred to as syndrome X), and obesity, among others. The polypeptides of the present disclosure, and compositions thereof, can be used, for example, to achieve and/or maintain glucose homeostasis, e.g., to reduce glucose level in the bloodstream and/or to reduce insulin level to a range found in a healthy subject.

The term "hyperglycemia", as used herein, refers to a condition in which an elevated amount of glucose circulates in the blood plasma of a subject relative to a healthy individual. Hyperglycemia can be diagnosed using methods known in the art, including measurement of fasting blood glucose levels as described herein.

The term "hyperinsulinemia", as used herein, refers to a condition in which there are elevated levels of circulating insulin when, concomitantly, blood glucose levels are either elevated or normal. Hyperinsulinemia can be caused by insulin resistance which is associated with dyslipidemia, such as high triglycerides, high cholesterol, high low-density lipoprotein (LDL) and low high-density lipoprotein (HDL); high uric acids levels; polycystic ovary syndrome; type II diabetes and obesity. Hyperinsulinemia can be diagnosed as having a plasma insulin level higher than about 2 µU/mL.

As used herein, the phrase "body weight disorder" refers to conditions associated with excessive body weight and/or enhanced appetite. Various parameters are used to determine whether a subject is overweight compared to a reference healthy individual, including the subject's age, height, sex and health status. For example, a subject may be considered overweight or obese by assessment of the subject's Body Mass Index (BMI), which is calculated by dividing a subject's weight in kilograms by the subject's height in meters squared. An adult having a BMI in the range of ~18.5 to ~24.9 kg/m$^2$ is considered to have a normal weight; an adult having a BMI between ~25 and ~29.9 kg/m$^2$ may be considered overweight (pre-obese); and an adult having a BMI of ~30 kg/m$^2$ or higher may be considered obese. Enhanced appetite frequently contributes to excessive body weight. There are several conditions associated with enhanced appetite, including, for example, night eating syndrome, which is characterized by morning anorexia and evening polyphagia often associated with insomnia, but which may be related to injury to the hypothalamus.

The term "Activators" refers to agents that, for example, stimulate, increase, activate, facilitate, enhance activation, sensitize or up-regulate the function or activity of one or more agents, e.g., polypeptides used to treat or prevent a metabolic disorder. In addition, Activators include agents that operate through the same mechanism of action as the polypeptides of the present invention (i.e., agents that modulate the same signaling pathway as the polypeptides in a manner analogous to that of the polypeptides) and are capable of eliciting a biological response comparable to (or greater than) that of the polypeptides. Examples of Activators include agonists such as small molecule compounds.

The term "Modulators" collectively refers to the polypeptides of the present invention and the Activators.

The terms "modulate", "modulation" and the like refer to the ability of an agent (e.g., an Activator) to increase the function or activity of one or more polypeptides (or the nucleic acid molecules encoding them), either directly or indirectly; or to the ability of an agent to produce an effect comparable to that of one or more polypeptides.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like. In specific embodiments, the terms refer to a polymeric form of amino acids of any length which include genetically coded amino acids. In particular embodiments, the terms refer to a polymeric form of amino acids of any length which include genetically coded amino acids fused to a heterologous amino acid sequence. In particular embodiments, the terms refer to an amino acid of 112 amino acids in length, optionally fused to a heterologous sequence. In specific embodiments, as appropriate, when referring to proteins and molecules disclosed and described herein, the terms "polypeptide," "peptide," and "protein" refer to Polypeptides as defined herein.

It will be appreciated that throughout this disclosure reference is made to amino acids according to the single letter or three letter codes. For the reader's convenience, the single and three letter amino acid codes are provided below:

| G | Glycine | Gly | P | Proline | Pro |
|---|---------|-----|---|---------|-----|
| A | Alanine | Ala | V | Valine | Val |
| L | Leucine | Leu | I | Isoleucine | Ile |

| | | | | | |
|---|---|---|---|---|---|
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

As used herein, the term "variant" encompasses naturally-occurring variants (e.g., homologs and allelic variants) and non-naturally-occuring variants (e.g., recombinantly modified). Naturally-occurring variants include homologs, i.e., nucleic acids and polypeptides that differ in nucleotide or amino acid sequence, respectively, from one species to another. Naturally-occurring variants include allelic variants, i.e., nucleic acids and polypeptides that differ in nucleotide or amino acid sequence, respectively, from one individual to another within a species. Non-naturally-occurring variants include nucleic acids and polypeptides that comprise a change in nucleotide or amino acid sequence, respectively, where the change in sequence is artificially introduced, e.g., the change is generated in the laboratory or other facility by human intervention ("hand of man").

The term "native" or "wild type", in reference to GDF15, refers to biologically active, naturally-occurring GDF15, including biologically active, naturally-occurring GDF15 variants. The term includes the 112 amino acid human GDF15 mature sequence (SEQ ID NO: 1).

The term "muteins" as used herein refers broadly to recombinant proteins, i.e., a polypeptide comprising an artificially introduced change in amino acid sequence, e.g., a change in amino acid sequence generated in the laboratory or other facility by human intervention ("hand of man"). These polypeptides usually carry single or multiple amino acid substitutions or deletions and are frequently derived from cloned genes that have been subjected to site-directed or random mutagenesis, or from completely synthetic genes. "GDF15 Muteins" of the present disclosure thus encompass, for example, amino acid substitutions and/or amino acid deletions (e.g., N-terminal truncations of 1, 2, 3, 4, 5, 6, 7, 8, 9, 10, 11, 12, 13, or 14 or more amino acids) relative to a reference polypeptide, e.g., relative to mature human GDF15 (SEQ ID NO: 1).

As used herein in reference to native human GDF15 or a GDF15 mutein, the terms "modified", "modification" and the like refer to one or more changes that modify a property of human GDF15, a naturally-occurring GDF15 variant, or a GDF15 mutein, where the change does not alter the primary amino acid sequence of the GDF15. Such a property includes, for example, solubility, circulation half-life, stability, clearance, immunogenicity or allergenicity, and manufacturability (e.g., cost and efficiency). "Modification" includes a covalent chemical modification that does not alter the primary amino acid sequence of the GDF15 polypeptide (native or mutein) itself. Changes to human GDF15, a naturally-occurring GDF15 variant, or a GDF15 mutein that may be carried out include, but are not limited to, pegylation (covalent attachment of one or more molecules of polyethylene glycol (PEG), or derivatives thereof); glycosylation (e.g., N-glycosylation), polysialylation and hesylation; maltose binding protein fusion; albumin fusion (e.g., HSA fusion); albumin binding through, for example, a conjugated fatty acid chain (acylation); Fc-fusion; and fusion with a PEG mimetic. Some particular embodiments entail modifications involving polyethylene glycol, other particular embodiments entail modifications involving albumin, and still other particular modifications entail modifications involving glycosylation, or a combination thereof.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

The term "probe" refers to a fragment of DNA or RNA corresponding to a gene or sequence of interest, wherein the fragment has been labeled radioactively (e.g., by incorporating $^{32}P$ or $^{35}S$) or with some other detectable molecule, such as biotin, digoxygenin or fluorescein. As stretches of DNA or RNA with complementary sequences will hybridize, a probe can be used, for example, to label viral plaques, bacterial colonies or bands on a gel that contain the gene of interest. A probe can be cloned DNA or it can be a synthetic DNA strand; the latter can be used to obtain a cDNA or genomic clone from an isolated protein by, for example, microsequencing a portion of the protein, deducing the nucleic acid sequence encoding the protein, synthesizing an oligonucleotide carrying that sequence, radiolabeling the sequence and using it as a probe to screen a cDNA library or a genomic library.

The term "heterologous" refers to two components that are defined by structures derived from different sources. For example, in the context of a polypeptide, a "heterologous" polypeptide may include operably linked amino acid sequences that are derived from different polypeptides (e.g., a first component comprising a recombinant polypeptide and a second component derived from a native GDF15 polypeptide). Similarly, in the context of a polynucleotide encoding a chimeric polypeptide, a "heterologous" polynucleotide may include operably linked nucleic acid sequences that can be derived from different genes (e.g., a first component from a nucleic acid encoding a polypeptide according to an embodiment disclosed herein and a second component from a nucleic acid encoding a carrier polypeptide). Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin than the promoter, the coding sequence or both). For example, a T7 promoter operably linked to a polynucleotide encoding a GDF15 polypeptide or domain thereof is said to be a heterologous nucleic acid. In the context of recombinant cells, "heterologous" can refer to the presence of a nucleic acid (or gene product, such as a polypeptide) that is of a different genetic origin than the host cell in which it is present.

The term "operably linked" refers to linkage between molecules to provide a desired function. For example, "operably linked" in the context of nucleic acids refers to a functional linkage between nucleic acid sequences. By way of example, a nucleic acid expression control sequence (such as a promoter, signal sequence, or array of transcription factor binding sites) may be operably linked to a second polynucleotide, wherein the expression control sequence affects transcription and/or translation of the second polynucleotide. In the context of a polypeptide, "operably linked" refers to a functional linkage between amino acid sequences (e.g., different domains) to provide for a described activity of the polypeptide.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" a GDF15 polypeptide), is meant to indicate that the polypeptide or nucleic acid has a sequence that is based on that of a reference polypeptide or nucleic acid (e.g., a naturally occurring GDF15 polypeptide or a GDF15-encoding nucleic acid), and is not meant to be limiting as to the source or method in which the protein or nucleic acid is made. By way of example, the term "derived from" includes homologues or variants of reference amino acid or DNA sequences.

In the context of a polypeptide, the term "isolated" refers to a polypeptide of interest that, if naturally occurring, is in an environment different from that in which it may naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates the polypeptide has been separated from an environment in which it was made by either synthetic or recombinant means.

"Enriched" means that a sample is non-naturally manipulated (e.g., in a laboratory, for example, by a scientist or a clinician) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "antibodies" (Abs) and "immunoglobulins" (Igs) refer to glycoproteins having the same structural characteristics. While antibodies exhibit binding specificity to a specific antigen, immunoglobulins include both antibodies and other antibody-like molecules which lack antigen specificity. Antibodies are described in detail hereafter.

The term "monoclonal antibody" refers to an antibody obtained from a population of substantially homogeneous antibodies, that is, the individual antibodies comprising the population are identical except for possible naturally occurring mutations that may be present in minor amounts. Monoclonal antibodies are highly specific, being directed against a single antigenic site. In contrast to polyclonal antibody preparations, which can include different antibodies directed against different determinants (epitopes), each monoclonal antibody is directed against a single determinant on the antigen.

In the context of an antibody, the term "isolated" refers to an antibody that has been separated and/or recovered from contaminant components of its natural environment; such contaminant components include materials which might interfere with diagnostic or therapeutic uses for the antibody, and may include enzymes, hormones, and other proteinaceous or nonproteinaceous solutes.

The phrase "conservative amino acid substitution" refers to substitution of amino acid residues within the following groups: 1) L, I, M, V, F; 2)R, K; 3) F, Y, H, W, R; 4) G, A, T, S; 5) Q, N; and 6) D, E. Conservative amino acid substitutions may preserve the activity of the protein by replacing an amino acid(s) in the protein with an amino acid with a side chain of similar acidity, basicity, charge, polarity, or size of the side chain. Guidance for substitutions, insertions, or deletions may be based on alignments of amino acid sequences of different variant proteins or proteins from different species.

Growth Differentiation Factor 15 (GDF15)

GDF15, also known as MIC-1 (macrophage inhibitory cytokine-1), PDF (prostate differentiation factor), PLAB (placental bone morphogenetic protein), NAG-1 (non-steroidal anti-inflammatory drugs (NSAIDs) activated gene), TGF-PL, and PTGFB, is a member of the transforming growth factor β (TGF-β) super-family. GDF15, which is synthesized as a 62 kDa intracellular precursor protein that is subsequently cleaved by a furin-like protease, is secreted as a 25 kDa disulfide-linked protein. [See, e.g., Fairlie et al., J. Leukoc. Biol 65:2-5 (1999)]. GDF15 mRNA is seen in several tissues, including liver, kidney, pancreas, colon and placenta, and GDF15 expression in liver can be significantly up-regulated during injury of organs such as the liver, kidneys, heart and lungs.

The GDF15 precursor is a 308 amino acid polypeptide (NCBI Ref. Seq.NP_004855.2) containing a 29 amino acid signal peptide, a 167 amino acid pro-domain, and a mature domain of 112 amino acids which is excised from the pro-domain by furin-like proteases. A 308-amino acid GDF15 polypeptide is referred to as a "full-length" GDF15 polypeptide; a 112-amino acid GDF15 polypeptide (amino acids 197-308 of "full-length" GDF15) is a "mature" GDF15 polypeptide (SEQ ID NO: 1). Unless otherwise indicated, the term "GDF15" refers to the 112 amino acid mature human sequence. In addition, numerical references to particular GDF15 residues refer to the 112 amino acid mature sequence (i.e., residue 1 is Ala (A), and residue 112 is Ile (I); see SEQ ID NO: 1). Of note, while the GDF15 precursor amino acid sequence predicts three excision sites, resulting in three putative forms of "mature" human GDF15 (i.e., 110, 112 and 115 amino acids), the 112 amino acid mature sequence is accepted as being correct.

The scope of the present disclosure includes GDF15 orthologs, and modified forms thereof, from other mammalian species, and their use, including mouse (NP_035949), chimpanzee (XP_524157), orangutan (XP_002828972), Rhesus monkey (EHH29815), giant panda (XP_002912774), gibbon (XP_003275874), guinea pig (XP_003465238), ferret (AER98997), cow (NP_001193227), pig (NP_001167527), dog (XP_541938) and platypus (*Ornithorhynchus anatinus*; AFV61279). The mature form of human GDF15 has approximately 67% amino acid identity to the mouse ortholog.

For the sake of convenience, the modified human GDF15 molecules, the GDF15 variants (e.g., muteins), and modified GDF15 muteins described henceforward are collectively referred to hereafter as the "Polypeptide(s)". It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it may correspond to a sequence of a naturally occurring human polypeptide or nucleic acid molecule. In particular embodiments, the modified human GDF15 molecules are N-glycosylated dimers. In specific embodiments, the modified human GDF15 molecules are N-glycosylated homodimers. In addition to the human polypeptides and the nucleic acid molecules which encode them, the present disclosure contemplates GDF15-related polypeptides and corresponding nucleic acid molecules from other species.

A. Polypeptides Having Desired Physical Properties

The present disclosure contemplates, in part, polypeptides that include a contiguous amino acid sequence that is at least 80%, 85%, 90%, 95%, 96%, 97%, 98%, 99%, or 100% identical to the amino acid sequence of SEQ ID NO: 1 (mature 112 amino acid long human GDF15). The polypeptides may include one or more amino acid substitutions and/or deletions relative to the amino acid sequence of SEQ ID NO: 1. In certain embodiments, in addition to the amino acid substitutions, the polypeptides of the present disclosure may also include amino acid deletions relative to the amino acid sequence of SEQ ID NO: 1. In some embodiments, the polypeptides of the present disclosure may include amino acid deletions relative to the amino acid sequence of SEQ ID NO: 1.

For convenience and clarity, the amino acid sequence of SEQ ID NO: 1 is used as a reference sequence for the polypeptides presented herein. Therefore, the amino acid residue positions are numbered herein with reference to SEQ ID NO: 1. The sequence of SEQ ID NO: 1 is presented below:
ARNGDHCPLGPGRCCRLHTVRASLEDLGWADWV-LSPREVQVTMCIGACPSQ FRAANMHAQIKT-SLHRLKPDTVPAPCCVPASYNPMVLIQKTDTGVSLQ-TYDDLLAKDC HCI In some embodiments, the polypeptides of the present disclosure may include one, two, three or more amino acid substitutions, additions, or deletions that introduce one or more N-linked glycosylation consensus site(s) at a location where such a site is not present in SEQ ID NO: 1. The N-linked glycosylation consensus site includes the sequence NXS/T, where N is Asn; X is an amino acid other than proline; followed by either Ser (S) or Thr (T).

Examples of polypeptides of the present disclosure include polypeptides that have one, two, three, four, or more glycosylation consensus sites (e.g., N-linked Glycosylation consensus sites) at an amino acid location where such a site is not present in the amino acid sequence of SEQ ID NO: 1.

In certain embodiments, the polypeptide may include one amino acid substitution relative to SEQ ID NO: 1 that provides one N-linked Glycosylation consensus site at the position of the substitution (e.g, a NG<u>D</u> sequence in SEQ ID NO: 1 may be changed to NGT/S by one substitution; position of substitution underlined). In other cases, the polypeptide may include two amino acid substitutions relative to SEQ ID NO: 1 that provide one N-linked Glycosylation consensus site at the position of the substitutions (e.g., a <u>KTD</u> sequence in SEQ ID NO: 1 may be changed to NTT/S by two substitutions; positions of substitutions underlined). In some embodiments, the polypeptide may include three amino acid substitutions relative to SEQ ID NO: 1 that provide one N-linked glycosylation consensus site at the position of the substitution (e.g., a <u>GPG</u> sequence in SEQ ID NO: 1 may be changed to NTT/S by three substitutions; position of substitutions underlined).

In certain embodiments, the polypeptide may include one or more amino acid deletion relative to SEQ ID NO: 1 that provides an N-linked glycosylation consensus site at the position of the deletion. For example, a NG<u>DHCPLGPGRCCRLH</u>T sequence in SEQ ID NO: 1 may be changed by deletion of amino acids D through H (underlined)) thereby providing an N-linked glycosylation consensus site: NGT.

In certain embodiments, the polypeptide may include one or more amino acid additions relative to SEQ ID NO: 1 that provides an N-linked glycosylation consensus site at the position(s) of the addition(s). An example of introduction of an N-linked glycosylation consensus site by addition of one amino acid includes adding an N to a sequence LHT in SEQ ID NO: 1, thereby generating the sequence LNHT, where NHT is an N-linked glycosylation consensus site.

As noted above, the polypeptide may include one or more substitutions relative to SEQ ID NO: 1 and the substitutions may be numbered as the position of the corresponding amino acid in SEQ ID NO: 1.

In certain embodiments, the polypeptide may include a contiguous amino acid sequence that is at least 80%, 85%, 90%, 95%, 96%, 97%, 98%, 99%, or 100% identical to the amino acid sequence of SEQ ID NO: 1, where the contiguous amino acid sequence has at least one of the following pairs of substitutions relative to the corresponding amino acids in SEQ ID NO: 1:
  i) D5T and R21N or D5S and R21N;
  ii) R16N and H18T or R16N and H18S;
  iii) S23N and E25T or S23N and E25S;
  iv) L24N and D26T or L24N and D26S;
  v) S50N and F52T; S50N and F52S; F52N and A54T; or F52N and A54S;
  vi) Q51N and R53T; Q51N and R53S; R53N and A55T; or R53N and A55S;
  vi) S64N and H66T or S64N and H66S;
  vii) L65N and R67T or L65N and R67S;
  viii) S82N and N84T or S82N and N84S;
  ix) K91N and D93T; K91N and D93S; D93N and G95T; or D93N and G95S;
  x) T94N and V96T; T94N and V96S; V96N and L98T; or V96N and L98S;
  xi) S97N and Q99T or S97N and Q99S; and
  xii) A106N and D108T or A106N and D108S.

For example, the substitutions in i) above, denotes that the polypeptide has a threonine (T) or serine (S) at an amino acid position that corresponds to amino acid position 5 in SEQ ID NO:1, wherein in SEQ ID NO: 1 an asparate (D) is present at the amino acid position 5. A substitution of a D at position 5 with a T or S can be denoted by D5T/S. The position of the corresponding amino acid in a polypeptide relative to SEQ ID NO: 1 may be determined by aligning the amino acid sequences.

In certain embodiments, the polypeptide may include two amino acid substitutions (a pair of substitutions) that provide a single N-glycosylation consensus sequence at a position where a N-glycosylation consensus sequence is not present in SEQ ID NO: 1. Examples of such substitutions include R16N and H18T/S; K91N and D93T/S; T94N and V96T/S;

and others listed above. R16N and H18T/S denotes that the polypeptide has a N at a position that corresponds to position 16 of SEQ ID NO: 1, where in SEQ ID NO: 1 an R is present and the polypeptide has a either T or S at a position that corresponds to position 18 in SEQ ID NO: 1, where H is present. Since the sequence RXH (at position 16-18) in SEQ ID NO: 1 does not include any residue for the N-linked glycosylation consensus sequence, the pair of substitutions leads to the introduction of the N-linked glycosylation consensus sequence.

In alternate embodiments, a single amino acid substitution may suffice to provide the N-linked glycosylation consensus sequence, for example, since the sequence NGD (at position 3-5) is present in SEQ ID NO: 1, a single substitution of D with T or S produces the sequence NGT or NGS, respectively, which are both N-glycosylation consensus sequences.

In certain cases, more than one N-glycosylation consensus sequence may be introduced into the wild type GDF15. For example, the wild type GDF15 amino acid sequence may be modified by subsititutions and/or deletions to provide one, two, three, four or more N-glycosylation consensus sequences. In certain embodiments, the polypeptide may be include 112 contiguous amino acids that has a sequence identity of at least 90% to the 112 amino acids sequence of SEQ ID NO: 1, where the 112 contiguous amino acids include one, two, three, four or more N-glycosylation consensus sequences, such as, 1-12, 1-10, 1-8, 1-6, 1-4, 1-3, or 1-2 N-glycosylation consensus sequences.

An example of a polypeptide with two N-glycosylation consensus sequences includes a GDF15 mutein having a T/S at position 5 (relative to SEQ ID NO: 1) and N at position 21 (relative to SEQ ID NO: 1).

Exemplary polypeptides of the present disclosure include those having two or more N-linked glycosylation consensus sequences. For example, the polypeptide may include a combination of two or more of the following pairs of substitutions:
i) D5T and R21N or D5S and R21N;
ii) R16N and H18T or R16N and H18S;
iii) S23N and E25T or S23N and E25S;
iv) L24N and D26T or L24N and D26S;
v) S50N and F52T; S50N and F52S; F52N and A54T; or F52N and A54S;
vi) Q51N and R53T; Q51N and R53S; R53N and A55T; or R53N and A55S;
vi) S64N and H66T; or S64N and H66S;
vii) L65N and R67T; or L65N and R67S;
viii) S82N and N84T or S82N and N84S;
ix) K91N and D93T; K91N and D93S; D93N and G95T; or D93N and G95S;
x) T94N and V96T; T94N and V96S; V96N and L98T; or V96N and L98S;
xi) S97N and Q99T; or S97N and Q99S; and
xii) A106N and D108T or A106N and D108S.

In certain embodiments, the Polypeptide may include a contiguous amino acid sequence that is at least 80%, 85%, 90%, 95%, 96%, 97%, 98%, 99%, or 100% identical to the amino acid sequence of SEQ ID NO: 1, where the contiguous amino acid sequence has at least one of the following pairs of substitutions relative to the corresponding amino acids in SEQ ID NO: 1:
i) D5T and R21N or D5S and R21N;
ii) R16N and H18T or R16N and H18S;
iii) S23N and E25T or S23N and E25S;
iv) S50N and F52T; S50N and F52S; F52N and A54T; or F52N and A54S;
v) Q51N and R53T; Q51N and R53S; R53N and A55T; or R53N and A55S;
vi) S64N and H66T; or S64N and H66S;
vii) K91N and D93T; K91N and D93S; D93N and G95T; or D93N and G95S;
viii) T94N and V96T; T94N and V96S; V96N and L98T; or V96N and L98S;
ix) S97N and Q99T; or S97N and Q99S; and
x) A106N and D108T or A106N and D108S;
wherein the substitution creates one or more N-linked glycosylation consensus sites having the sequence NXS/T, where N is Asn; X is an amino acid other than proline; followed by either Ser (S) or Thr (T) and further wherein one or more N-linked glycosylation consensus sites are linked to an N-glycan. In a further embodiment, the Polypeptide forms a dimer. In a further embodiment, the Polypeptide has N-terminal truncations and/or C-terminal truncations relative to SEQ ID NO: 1. The truncations may be of 1, 2, 3, 4, 5, 6, 7, 8, 9, 10, 11, 12, 13, 14 or more amino acids relative to a reference polypeptide, e.g., SEQ ID NO: 1. In a specific embodiment, the Polypeptide has a truncation of the first three N-terminal residues in GDF15 (ΔARN or ΔN3). In a further embodiment, the Polypeptide has a solubility of at least 0.5 mg/ml, e.g., at least 1 mg/ml, at least 2 mg/ml, at least 3 mg/ml, at least 4 mg/ml, at least 5 mg/ml, at least 8 mg/ml, at least 10 mg/ml, at least 15 mg/ml, at least 20 mg/ml, or at least 25 mg/ml, for example a solubility in the range of 0.5 mg/ml to 25 mg/ml, 0.5 mg/ml to 20 mg/ml, 1 mg/ml to 25 mg/ml, 1 mg/ml to 20 mg/ml, 3 mg/ml to 25 mg/ml, 3 mg/ml to 20 mg/ml, 5 mg/ml to 25 mg/ml, 5 mg/ml to 20 mg/ml, or 5 mg/ml to 18 mg/ml in a buffer solution. In certain cases, the Polypeptide has a solubility of at least 0.5 mg/ml, e.g., at least 1 mg/ml, at least 2 mg/ml, at least 3 mg/ml, at least 4 mg/ml, at least 5 mg/ml, at least 8 mg/ml, at least 10 mg/ml, at least 15 mg/ml, at least 20 mg/ml, or at least 25 mg/ml, for example a solubility in the range of 0.5 mg/ml to 25 mg/ml, 0.5 mg/ml to 20 mg/ml, 1 mg/ml to 25 mg/ml, 1 mg/ml to 20 mg/ml, 3 mg/ml to 25 mg/ml, 3 mg/ml to 20 mg/ml, 5 mg/ml to 25 mg/ml, 5 mg/ml to 20 mg/ml, or 5 mg/ml to 18 mg/ml in a buffer solution. The buffer may be a phosphate buffer, Tris buffer, HEPES buffer, MOPS buffer, PIPES buffer, or the like, or a combination thereof. In certain cases, the buffer may include phosphate buffered saline. In certain cases, the buffer may include Tris, potassium phosphate and sodium chloride. In some cases, the buffer may include Tris, potassium phosphate, sodium chloride, and formic acid. For example, the buffer may include 10 mM-100 mM Tris pH7, 1 mM-50 mM potassium phosphate, 100 mM-200 mM sodium chloride, and 10 mS/cm-30 mS/cm formic acid. In further embodiments, the Polypeptide decreases blood glucose level, body weight, and/or food intake by at least 10%, 20%, 30%, 50%, 60%, 70%, 80%, or 90% as compared to that prior to administration of the Polypeptide.

In certain embodiments, the Polypeptide may include a contiguous amino acid sequence that is at least 80%, 85%, 90%, 95%, 96%, 97%, 98%, 99%, or 100% identical to the amino acid sequence of SEQ ID NO: 1, where the contiguous amino acid sequence has at least one of the following pairs of substitutions relative to the corresponding amino acids in SEQ ID NO: 1:
i) D5T and R21N;
ii) S23N and E25T;
iii) F52N and A54T;
iv) R53N and A55T;
v) S64N and H66T;
vi) K91N and D93T;

vii) D93N and G95T;
viii) S97N and Q99T; and
ix) A106N and D108T;
wherein the substitution creates one or more N-linked glycosylation consensus sites having the sequence NXS/T, where N is Asn; X is an amino acid other than proline; followed by either Ser (S) or Thr (T) and further wherein one or more N-linked glycosylation consensus sites are linked to an N-glycan. In a further embodiment, the Polypeptide forms a dimer. In a further embodiment, the Polypeptide has N-terminal truncations and/or C-terminal truncations relative to SEQ ID NO: 1. The truncations may be of 1, 2, 3, 4, 5, 6, 7, 8, 9, 10, 11, 12, 13, 14 or more amino acids relative to a reference polypeptide, e.g., SEQ ID NO: 1. In a specific embodiment, the Polypeptide has a truncation of the first three N-terminal residues in GDF15 (ΔARN or ΔN3). In a further embodiment, the Polypeptide has a solubility of at least 0.5 mg/ml, e.g., at least 1 mg/ml, at least 2 mg/ml, at least 3 mg/ml, at least 4 mg/ml, at least 5 mg/ml, at least 8 mg/ml, at least 10 mg/ml, at least 15 mg/ml, at least 20 mg/ml, or at least 25 mg/ml, for example a solubility in the range of 0.5 mg/ml to 25 mg/ml, 0.5 mg/ml to 20 mg/ml, 1 mg/ml to 25 mg/ml, 1 mg/ml to 20 mg/ml, 3 mg/ml to 25 mg/ml, 3 mg/ml to 20 mg/ml, 5 mg/ml to 25 mg/ml, 5 mg/ml to 20 mg/ml, or 5 mg/ml to 18 mg/ml in a buffer solution. In certain cases, the Polypeptide has a solubility of at least 0.5 mg/ml, e.g., at least 1 mg/ml, at least 2 mg/ml, at least 3 mg/ml, at least 4 mg/ml, at least 5 mg/ml, at least 8 mg/ml, at least 10 mg/ml, at least 15 mg/ml, at least 20 mg/ml, or at least 25 mg/ml, for example a solubility in the range of 0.5 mg/ml to 25 mg/ml, 0.5 mg/ml to 20 mg/ml, 1 mg/ml to 25 mg/ml, 1 mg/ml to 20 mg/ml, 3 mg/ml to 25 mg/ml, 3 mg/ml to 20 mg/ml, 5 mg/ml to 25 mg/ml, 5 mg/ml to 20 mg/ml, or 5 mg/ml to 18 mg/ml in a buffer solution. The buffer may be a phosphate buffer, Tris buffer, HEPES buffer, MOPS buffer, PIPES buffer, or the like, or a combination thereof. In certain cases, the buffer may include phosphate buffered saline. In certain cases, the buffer may include Tris, potassium phosphate and sodium chloride. In some cases, the buffer may include Tris, potassium phosphate, sodium chloride, and formic acid. For example, the buffer may include 10 mM-100 mM Tris pH7, 1 mM-50 mM potassium phosphate, 100 mM-200 mM sodium chloride, and 10 mS/cm-30 mS/cm formic acid. In further embodiments, the Polypeptide decreases blood glucose level, body weight, and/or food intake by at least 10%, 20%, 30%, 50%, 60%, 70%, 80%, or 90% as compared to that prior to administration of the Polypeptide. In specific embodiments, the Polypeptide comprises or consists essentially of: SEQ ID NO: 2, SEQ ID NO: 4, SEQ ID NO: 8, SEQ ID NO: 9, SEQ ID NO: 10, SEQ ID NO: 13, SEQ ID NO: 14, SEQ ID NO: 17, SEQ ID NO: 18 or SEQ ID NO: 30. In specific embodiments, the Polypeptide comprises or consists essentially of: SEQ ID NO: 81, SEQ ID NO: 83, SEQ ID NO: 87, SEQ ID NO: 88, SEQ ID NO: 89, SEQ ID NO: 92, SEQ ID NO: 93, SEQ ID NO: 96, SEQ ID NO: 97 or SEQ ID NO: 100. In certain embodiments, the Polypeptide may include a contiguous amino acid sequence that is at least 95% identical to the amino acid sequence of SEQ ID NO: 1, where the contiguous amino acid sequence has at least one of the following pairs of substitutions relative to the corresponding amino acids in SEQ ID NO: 1:

i) D5T and R21N;
ii) S64N and H66T;
iii) K91N and D93T;
iv) D93N and G95T; and v) S97N and Q99T; wherein the substitution creates one or more N-linked glycosylation consensus sites having the sequence NXS/T, where N is Asn; X is an amino acid other than proline; followed by either Ser (S) or Thr (T) wherein one or more N-linked glycosylation consensus sites are linked to an N-glycan; further wherein the Polypeptide forms a dimer; and further wherein the Polypeptide has a solubility of at least 1 mg/ml in a buffer solution.

In further embodiments, the Polypeptide has a solubility of at least 5 mg/ml in a buffer solution. The buffer may be a phosphate buffer, Tris buffer, HEPES buffer, MOPS buffer, PIPES buffer, or the like, or a combination thereof. In certain cases, the buffer may include phosphate buffered saline. In certain cases, the buffer may include Tris, potassium phosphate and sodium chloride. In some cases, the buffer may include Tris, potassium phosphate, sodium chloride, and formic acid. For example, the buffer may include 10 mM-100 mM Tris pH7, 1 mM-50 mM potassium phosphate, 100 mM-200 mM sodium chloride, and 10 mS/cm-30 mS/cm formic acid. In further embodiments, the Polypeptide decreases blood glucose level, body weight, and/or food intake by at least 10%, 20%, 30%, 50%, 60%, 70%, 80%, or 90% as compared to that prior to administration of the Polypeptide. In a further embodiment, the Polypeptide has N-terminal truncations and/or C-terminal truncations relative to SEQ ID NO: 1. The truncations may be of 1, 2, 3, 4, 5, 6, 7, 8, 9, 10, 11, 12, 13, 14 or more amino acids relative to a reference polypeptide, e.g., SEQ ID NO: 1. In a specific embodiment, the Polypeptide has a truncation of the first three N-terminal residues in GDF15 (ΔARN or ΔN3). In specific embodiments, the Polypeptide comprises or consists essentially of: SEQ ID NO: 2, SEQ ID NO: 10, SEQ ID NO: 13, SEQ ID NO: 14, SEQ ID NO: 17 or SEQ ID NO: 30. In specific embodiments, the Polypeptide comprises or consists essentially of: SEQ ID NO: 81, SEQ ID NO: 89, SEQ ID NO: 92, SEQ ID NO: 93, SEQ ID NO: 96 or SEQ ID NO: 100.

In certain embodiments, the polypeptide may include 112 contiguous amino acids that has a sequence identity of at least 90% to the 112 amino acids sequence of SEQ ID NO: 1, where the 112 contiguous amino acids include one, two, three, four or more of the pairs of substitutions set forth above.

FIG. 1 depicts the amino acid sequences of exemplary polypeptides (numbered 1 through 17) contemplated in the present disclosure aligned with the amino acid sequence of wild type mature human GDF15 (WT hGDF15; SEQ ID NO: 1). In FIG. 1, polypeptides that include two N-linked glycosylated consensus sites (mutant numbered 1; SEQ ID NO: 2) as well as polypeptides that include one N-linked glycosylated consensus site (mutants numbered 2-17; SEQ ID NOs: 3 to 18, respectively) are depicted.

In certain embodiments, the present disclosure contemplates a modified GDF15 N-glycosylated dimer, wherein said dimer comprises two Polypeptides disclosed herein covalently joined to each other. In particular embodiments, the two Polypeptides each comprise an amino acid sequence selected from: SEQ ID NO: 2, SEQ ID NO: 4, SEQ ID NO: 8, SEQ ID NO: 9, SEQ ID NO: 10, SEQ ID NO: 13, SEQ ID NO: 14, SEQ ID NO: 17, SEQ ID NO: 18 or SEQ ID NO: 30 or an amino acid differing by up to 5 amino acids; wherein said Polypeptides contain at least one N-glycosylation site that is N-glycosylated. In specific embodiments, the two Polypeptides each comprise an amino acid sequence selected from: SEQ ID NO: 2, SEQ ID NO: 4, SEQ ID NO: 8, SEQ ID NO: 9, SEQ ID NO: 10, SEQ ID NO: 13, SEQ ID NO: 14, SEQ ID NO: 17, SEQ ID NO: 18 or SEQ ID NO: 30 or an amino acid differing by up to 2 amino acids; wherein said Polypeptides contain at least one N-glycosylation site that is N-glycosylated. In particular embodiments, the two Polypeptides each consist of an amino acid sequence selected from: SEQ ID NO: 81, SEQ ID NO: 83, SEQ ID NO: 87, SEQ ID NO: 88, SEQ ID NO: 89, SEQ ID NO: 92, SEQ ID NO: 93, SEQ ID NO: 96, SEQ ID NO: 97 or SEQ ID NO: 100 or an amino acid differing by up to 5 amino acids; wherein said Polypeptides contain at least one N-glycosylation site that is N-glycosylated. In particular embodiments, the two Polypeptides each consist of an amino acid sequence selected from: SEQ ID NO: 81, SEQ ID NO: 83, SEQ ID NO: 87, SEQ ID NO: 88, SEQ ID NO: 89, SEQ ID NO: 92, SEQ ID NO: 93, SEQ ID NO: 96, SEQ ID NO: 97 or SEQ ID NO: 100 or an amino acid differing by up to 2 amino acids; wherein said Polypeptides contain at least one N-glycosylation site that is N-glycosylated. In further embodiments, the modified GDF15 N-glycosylated dimer is a homodimer joined by an interchain disulfide bond. In further embodiments, the modified GDF15 N-glycosylated dimer is a homodimer having two polypeptides as disclosed herein each comprising the same amino acid sequences, wherein said polypeptides contain at least one N-glycosylation site that is N-glycosylated.

The present disclosure also contemplates polypeptides that are active fragments (e.g., subsequences) of the polypeptides described above. The length of active fragments or subsequences may be 40 amino acids to 111 amino acids, e.g., 40, 45, 50, 55, 60, 65, 70, 75, 80, 85, 90, 95, 98, 106, 109, or up to 111 amino acids.

The polypeptides have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable Polypeptide can comprise an amino acid sequence having at least about 75%, at least about 80%, at least about 85%, at least about 90%, at least about 95%, at least about 98%, or at least about 99%, amino acid sequence identity to a contiguous stretch of 40, 45, 50, 55, 60, 65, 70, 75, 80, 85 or up to 112 amino acids in SEQ ID NO: 1.

Exemplary fragments of the polypeptides disclosed herein include polypeptides that have deletions of amino acids relative to SEQ ID NO: 1. For example, the polypeptides may have N-terminal truncations and/or C-terminal truncations relative to SEQ ID NO: 1. The truncations may be of 1, 2, 3, 4, 5, 6, 7, 8, 9, 10, 11, 12, 13, 14 or more amino acids relative to a reference polypeptide, e.g., SEQ ID NO: 1. In certain embodiments, a polypeptide of interest may include one or more substitutions that introduce an N-linked glycosylation consensus sequence, such as the one disclosed herein, and N-terminal truncations and/or C-terminal truncations relative to SEQ ID NO: 1.

In certain embodiments, the polypeptide may be at least 98 amino acids long and have an amino acid sequence identity of at least 90% to a corresponding stretch of 98 amino acids in SEQ ID NO: 1. This polypeptide may be lacking the first three to first fourteen amino acids (e.g., 3, 4, 5, 6, 7, 8, 9, 10, 11, 12, 13, or 14 amino acids) present at the N-terminus of SEQ ID NO: 1, while retaining the amino acids present at the C-terminus of SEQ ID NO:1. In other words, the deleted amino acid(s) correspond to the N-terminus amino acids of SEQ ID NO: 1.

In certain embodiments, the GDF15 mutein may be at least 106 amino acids long and have an amino acid sequence identity of at least 90% to a corresponding stretch of 106 amino acids in SEQ ID NO: 1. The GDF15 mutein may be lacking the first six amino acids present at the N-terminus of SEQ ID NO: 1.

In certain embodiments, the polypeptide may be at least 109 amino acids long and have an amino acid sequence identity of at least 90% to a corresponding stretch of 109 amino acids in SEQ ID NO: 1. The GDF15 mutein may be lacking the first three amino acids present at the N-terminus of SEQ ID NO: 1.

Exemplary polypeptides of the present disclosure are depicted in FIG. 2. The exemplary polypeptides (numbered 1 through 17) depicted in FIG. 1 are the same length as the WT hGDF15. The exemplary polypeptides (numbered 18 through 34; SEQ ID NOs: 19-35) depicted in FIG. 2 are 109 amino acids in length as they include a deletion of the three N-terminal amino acids (ΔN3) relative to the WT hGDF15. However, when referring to the position of the amino acid substitutions, the residue number indicated is the one that corresponds to the position in the WT mature hGDF15 (WT; SEQ ID NO: 1). Thus, the amino acid G at the N-terminus of the polypeptides is referred to as residue 4 although it is the first amino acid in the polypeptide amino acid sequence.

As noted above, these polypeptide fragments may include one or more amino acid substitutions that introduce a N-glycosylation consensus sequence relative to the sequence of SEQ ID NO: 1, such as, one, two, or more of the amino acids substitutions disclosed herein.

As indicated above and as described in more detail below, the polypeptides of the present disclosure may be modified through, for example, pegylation (covalent attachment of one or more molecules of polyethylene glycol (PEG), or derivatives thereof); glycosylation (e.g., N-glycosylation); polysialylation; albumin fusion molecules comprising serum albumin (e.g., human serum albumin (HSA), cyno serum albumin, or bovine serum albumin (BSA)); albumin binding through, for example, a conjugated fatty acid chain (acylation); Fc-fusion; and fusion with a PEG mimetic. In certain embodiments, the modifications are introduced in a site-specific manner. In other embodiments, the modifications include a linker. The linker may conjugate the modifying moiety to the polypeptide.

In particular embodiments, the present disclosure contemplates modification of mature human GDF15 and GDF15 muteins (such as the polypeptides described above) by conjugation with albumin. In other embodiments, the present disclosure contemplates modification of the polypeptides via N-glycosylation or O-glycosylation. The characteristics of albumins and polypeptide conjugates thereof (e.g., fusion proteins), and glycosylated polypeptides are described further hereafter.

Particular Modifications to Modify and/or Mimic GDF15 Function

A Polypeptide can include one or more modifications that enhance a property desirable in a protein formulated for therapy (e.g., serum half-life), that enable the raising of antibodies for use in detection assays (e.g., epitope tags), that provide for ease of protein purification, etc. Such modifications include, but are not limited to, pegylation (covalent attachment of one or more molecules of polyethylene glycol (PEG), or derivatives thereof); glycosylation (N- and O-linked); polysialylation; albumin fusion; albumin binding through a conjugated fatty acid chain (acylation); Fc-fusion proteins; and fusion with a PEG mimetic.

As set forth herein, the present disclosure contemplates fusion molecules comprising mature GDF15 polypeptide (e.g., mature human GDF15) or a GDF15 mutein polypeptide (e.g., a mutein of mature human GDF15), wherein the mature GDF15 polypeptide or GDF15 mutein polypeptide comprises at least one modification that does not alter its amino acid sequence, and wherein the modification improves at least one physical property of the polypeptide or the mutein polypeptide. In one embodiment, the GDF15 polypeptide or GDF15 mutein polypeptide modification comprises conjugation with serum albumin (e.g., human serum albumin (HSA), cyno serum albumin, or bovine serum albumin (BSA)). In some embodiments, the physical property is solubility.

In embodiments wherein the fusion molecule comprises a modified GDF15 polypeptide or a GDF15 mutein (such as the polypeptides disclosed above), either of which is conjugated to albumin, the solubility of the fusion molecule is generally improved relative to unconjugated recombinant human GDF15. In certain embodiments, the fusion molecule has a solubility of at least 1 mg/mL in phosphate buffered saline (PBS) at pH 7.0. In other embodiments, the fusion molecule has a solubility of at least 2 mg/mL, at least 3 mg/mL, at least 4 mg/mL, or at least 5 mg/mL. In other embodiments, the fusion molecule has a solubility of at least 6 mg/mL in phosphate buffered saline (PBS) at pH 7.0, at least 7 mg/mL, at least 8 mg/mL, at least 9 mg/mL, or at least 10 mg/mL. In particular embodiments, the fusion molecule has a solubility of greater than 10 mg/mL.

Pegylation: The clinical effectiveness of protein therapeutics is often limited by short plasma half-life and susceptibility to protease degradation. Studies of various therapeutic proteins (e.g., filgrastim) have shown that such difficulties may be overcome by various modifications, including conjugating or linking the polypeptide sequence to any of a variety of nonproteinaceous polymers, e.g., polyethylene glycol (PEG), polypropylene glycol, or polyoxyalkylenes (see, for example, typically via a linking moiety covalently bound to both the protein and the nonproteinaceous polymer, e.g., a PEG). Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, but certain embodiments have a molecular weight between 500 and 20,000 while other embodiments have a molecular weight between 4,000 and 10,000.

The present disclosure also contemplates compositions of conjugates wherein the PEGs have different n values and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. For example, cation exchange chromatography may be used to separate conjugates, and a fraction is then identified which contains the conjugate having, for example, the desired number of PEGs attached, purified free from unmodified protein sequences and from conjugates having other numbers of PEGs attached.

PEG may be bound to a polypeptide of the present disclosure via a terminal reactive group. The terminal reactive group may mediate a bond between the free amino or carboxyl groups of one or more of the polypeptide sequences and polyethylene glycol. The terminal reactive group may be attached to a discrete-length polyethylene glycol spacer. These PEG spacers increase reagent and conjugate solubility, minimize toxic and immunological effects compared to non-PEG spacers, and provide several options for accommodating specific crosslinking distances between PEG and a polypeptide. Exemplary PEG spacers with reactive groups include amine-reactive pegylated crosslinkers (e.g., Bis(succinimidyl)penta(ethylene glycol) (BS(PEG)$_5$)); sulfhydryl-reactive pegylated crosslinkers (1,11-Bismaleimidotriethyleneglycol (BM(PEG)$_3$)); bifunctional pegylated crosslinkers (NHS-PEGn-Maleimide Succinimidyl([N-maleimidopropionamido]-ethyleneglycol)ester (SM(PEG)n); n=2-24). The PEG spacer may be bound to the free amino group. PEG spacers include N-hydroxysuccinylimide polyethylene glycol which may be prepared by activating succinic acid ester of polyethylene glycol with N-hydroxysuccinylimide. Another activated polyethylene glycol which may be bound to a free amino group is 2,4-bis(O-methoxypolyethyleneglycol)-6-chloro-s-triazine which may be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art may be used to terminate the reaction. In some embodiments the reaction is terminated by acidifying the reaction mixture and freezing at, e.g., −20° C.

The present disclosure also contemplates the use of PEG Mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Glycosylation: For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties of proteins and can also be important in protein stability, secretion, and subcellular localization. Indeed, glycosylation of the GDF15 mutein polypeptides described herein imparts beneficial improvements to their physical properties. By way of example, but not limitation, solubility of GDF15 muteins can be improved by glycosylation, and such improvement may be substantial (see Examples). The glycosylated GDF15 mutein polypeptides described herein have higher solubility compared to the wild type GDF15, which is not glycosylated. In certain embodiments, the glycosylated GDF15 muteins disclosed herein have a solubility of at least 0.5 mg/ml, e.g., at least 1 mg/ml, at least 2 mg/ml, at least 3 mg/ml, at least 4 mg/ml, at least 5 mg/ml, at least 8 mg/ml, at least 10 mg/ml, at least 15 mg/ml, at least 20 mg/ml, or at least 25 mg/ml, for example a solubility in the range of 0.5 mg/ml to 25 mg/ml, 0.5 mg/ml to 20 mg/ml, 1 mg/ml to 25 mg/ml, 1 mg/ml to 20 mg/ml, 3 mg/ml to 25 mg/ml, 3 mg/ml to 20 mg/ml, 5 mg/ml to 25 mg/ml, 5 mg/ml to 20 mg/ml, or 5 mg/ml to 18 mg/ml in a buffer solution. In certain cases, the glycosylated GDF15 muteins described herein may have a solubility of at least 0.5 mg/ml, e.g., at least 1 mg/ml, at least 2 mg/ml, at least 3 mg/ml, at least 4 mg/ml, at least 5 mg/ml, at least 8 mg/ml, at least 10 mg/ml, at least 15 mg/ml, at least 20 mg/ml, or at least 25 mg/ml, for example a solubility in the range of 0.5 mg/ml to 25 mg/ml, 0.5 mg/ml to 20 mg/ml, 1 mg/ml to 25 mg/ml, 1 mg/ml to 20 mg/ml, 3 mg/ml to 25 mg/ml, 3 mg/ml to 20 mg/ml, 5 mg/ml to 25 mg/ml, 5 mg/ml to 20 mg/ml, or 5 mg/ml to 18 mg/ml in a buffer solution. The buffer may be a phosphate buffer, Tris buffer, HEPES buffer, MOPS buffer, PIPES buffer, or the like, or a combination thereof. In certain cases, the buffer may include phosphate buffered saline. In certain cases, the buffer may include Tris, potassium phosphate and sodium chloride. In some cases, the buffer may include Tris, potassium phosphate, sodium chloride, and formic acid. For example, the buffer may include 10 mM-100 mM Tris pH7, 1 mM-50 mM potassium phosphate, 100 mM-200 mM sodium chloride, and 10 mS/cm-30 mS/cm formic acid.

The glycosylated GDF15 mutein polypeptides disclosed herein are superior to the wild type mature GDF15 polypeptide. These glycosylated GDF15 mutein polypeptides have an improved characteristic compared to the wild type mature GDF15 polypeptide including but not limited to one or more of: greater yield in cell culture, improved dimer formation, greater solubility, and reduced immunogenicity. The solubility improvement exhibited by such modified GDF15 muteins can, for example, enable the generation of formulations more suitable for pharmaceutical administration than non-glycosylated GDF15/GDF15 muteins. The glycosylated GDF15/GDF15 mutein polypeptides may also exhibit enhanced stability. Moreover, the polypeptides may improve one or more pharmacokinetic properties, such as half-life.

Addition of glycosylation sites can be accomplished by altering the amino acid sequence as described above. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment of the present disclosure comprises the generation and use of N-glycosylation variants as described above.

Another means of increasing the number of carbohydrate moieties on the polypeptide is by chemical or enzymatic coupling of glycosides to the polypeptide.

Dihydrofolate reductase (DHFR)-deficient Chinese Hamster Ovary (CHO) cells are a commonly used host cell for the production of recombinant glycoproteins. These cells do not express the enzyme beta-galactoside alpha-2,6-sialyltransferase and therefore do not add sialic acid in the alpha-2,6 linkage to N-linked oligosaccharides of glycoproteins produced in these cells.

Polysialylation: The present disclosure also contemplates the use of polysialylation, the conjugation of peptides and proteins to the naturally occurring, biodegradable α-(2→8) linked polysialic acid ("PSA") in order to improve their stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of in vivo activity, and reduction in immunogenicity and antigenicity (see, e.g., G. Gregoriadis et al., Int. J. Pharmaceutics 300(1-2): 125-30). As with modifications with other conjugates (e.g., PEG), various techniques for site-specific polysialylation are available (see, e.g., T. Lindhout et al., PNAS 108(18)7397-7402 (2011)).

Fusion Proteins. The present disclosure contemplates fusion proteins of wild type mature GDF15 (e.g., human GDF15), as well as fusion proteins of the Polypeptides of the present disclosure (e.g., modified human GDF15 molecules, muteins of human GDF15, modified GDF15 muteins, and the like). Such fusion proteins are generally comprised of a non-GDF15 polypeptide (e.g., albumin (e.g., HSA) or a fragment thereof: albumin binding domain (ABD); Fc polypeptide; maltose binding domain (MBD), which may be referred to herein as a "fusion partner", conjugated to the wild type GDF15 polypeptide or Polypeptide of the present disclosure at its N-terminus or C-terminus. Optionally, the fusion partner may be conjugated to the wild type GDF15 or Polypeptide through a linker polypeptide. The linker polypeptide may optionally be a cleavable linker, e.g., an enzymatically cleavable linker. Examples of fusion partners are described below.

Albumin Fusion: Suitable fusion partner for conjugation include albumins such as human serum albumin (HSA), cyno serum albumin, and bovine serum albumin (BSA).

Mature HSA, a 585 amino acid polypeptide (~67 kDa) having a serum half-life of ~20 days, is primarily responsible for the maintenance of colloidal osmotic blood pressure, blood pH, and transport and distribution of numerous endogenous and exogenous ligands. The protein has three structurally homologous domains (domains I, II and III), is almost entirely in the alpha-helical conformation, and is highly stabilized by 17 disulfide bridges. The three primary drug binding regions of albumin are located on each of the three domains within sub-domains IB, IIA and IIIA.

Albumin synthesis takes place in the liver, which produces the short-lived, primary product preproalbumin. Thus, the full-length HSA has a signal peptide of 18 amino acids followed by a pro-domain of 6 amino acids; this 24 amino acid residue peptide may be referred to as the pre-pro domain. HSA can be expressed and secreted using its endogenous signal peptide as a pre-pro-domain. Alternatively, HSA can be expressed and secreted using a IgK signal peptide fused to a mature HSA. Preproalbumin is rapidly co-translationally cleaved in the endoplasmic reticulum lumen at its amino terminus to produce the stable, 609-amino acid precursor polypeptide, proalbumin. Proalbumin then passes to the Golgi apparatus, where it is converted to the 585 amino acid mature albumin by a furin-dependent amino-terminal cleavage. Unless otherwise indicated, "albumin" or "mature albumin" refers to HSA.

The primary amino acid sequences, structure, and function of albumins are highly conserved across species, as are the processes of albumin synthesis and secretion. Albumin serum proteins comparable to HSA are found in, for example, cynomolgus monkeys, cows, dogs, rabbits and rats. Of the non-human species, bovine serum albumin (BSA) is the most structurally similar to HSA. [See, e.g., Kosa et al., J Pharm Sci. 96(11):3117-24 (November 2007)]. The present disclosure contemplates the use of albumin from non-human species, including, but not limited to, those set forth above, in, for example, fusion to GDF15 Polypeptide. In certain embodiments, the non-human species is a cow. In other embodiments, the non-human species is a cynomolgus monkey.

According to the present disclosure, albumin may be conjugated to a drug molecule (e.g., a polypeptide described herein) at the carboxyl terminus, the amino terminus, both the carboxyl and amino termini, or internally (see, e.g., U.S. Pat. Nos. 5,876,969 and 7,056,701). Furthermore, the present disclosure contemplates albumin fusion proteins comprising more than one homologous (e.g., multiple GDF15 mutein molecules) or heterologous (e.g., a GDF15 mutein molecule and a distinct anti-diabetic agent) drug molecules.

In the HSA-polypeptide conjugates contemplated by the present disclosure, various forms of albumin may be used, such as HSA variants, such as, fragments. Such forms generally possess one or more desired albumin activities. In additional embodiments, the present disclosure involves fusion proteins comprising a polypeptide drug molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof.

HSA may be conjugated via a linker to a polypeptide described herein to generate a fusion protein. Examples of suitable linkers are described herein. Some embodiments contemplate a peptide linker of, for example, four-to-thirty amino acids.

In embodiments wherein the fusion protein comprises a linker, the linker may be a non-cleavable linker. For example, in one embodiment the present disclosure describes a fusion molecule wherein the HSA precursor amino acid sequence or the mature HSA is fused to the N-terminus of the mature human GDF15 or a GDF15 mutein amino acid sequence through a non-cleavable $(G_4S)_3$ linker.

In other embodiments wherein the fusion protein comprises a linker, the linker may be a cleavable linker. For example, the disclosure contemplates a fusion molecule wherein the HSA precursor amino acid sequence or the mature HSA amino acid sequence is fused to the N-terminus of the mature human GDF15 or a GDF15 mutein amino acid sequence as provided herein through a protease-sensitive $(G_4S)_2$ Factor Xa-cleavable linker.

Construction of HSA-cleavable linker-mature recombinant GDF15/GDF15 mutein molecules, as well as construction of mature recombinant GDF15/GDF15 mutein-cleavable linker-HSA fusion molecules, may be used to facilitate the assessment of, for example, solubility and the determination of in vivo efficacy of the GDF15/GDF15 mutein. In such embodiments, the GDF15/GDF15 mutein may be excised from the HSA chaperone through intracellular cleavage or through in vitro enzymatic cleavage. In some embodiments, excision is effected by proteolytic digestion of the cleavable linker using any viable protease. In other embodiments, GDF15 muteins can also be generated as non-HSA fusions via construction of a signal peptide fused to the polypeptides provided herein.

Intracellular cleavage may be carried out enzymatically by, for example, furin or caspase. A host cell expressing the fusion protein may express a low level of these endogenous enzymes, which are capable of cleaving a portion of the fusion molecules intracellularly; thus, some of the polypeptides are secreted from the cell without being conjugated to HSA, while some of the polypeptides are secreted in the form of fusion molecules that comprise HSA. Embodiments of the present disclosure contemplate the use of various furin fusion constructs. For example, constructs may be designed that comprise the sequence RGRR (SEQ ID NO: 36), RKRKKR (SEQ ID NO: 37), RKKR (SEQ ID NO: 38), or RRRKKR (SEQ ID NO: 39). Such constructs can have the following general structure: Igk-HSA-$(G_4S)_2$-furin sequence-hGDF15.

The present disclosure also contemplates extra-cellular cleavage (i.e., ex-vivo cleavage) whereby the fusion molecules are secreted from the cell, subjected to purification, then cleaved (e.g., using, for example, a Factor Xa proteolytic-sensitive linker or an enterokinase). It is understood that the excision may dissociate the entire HSA-linker complex from the Polypeptide (e.g., mature GDF15 or GDF15 mutein), or less than the entire HSA-linker complex.

As described above, fusion of albumin to one or more polypeptides of the present disclosure can, for example, be achieved by genetic manipulation, such that the DNA coding for HSA, or a fragment thereof, is joined to the DNA coding for the one or more polypeptide sequences. Thereafter, a suitable host can be transformed or transfected with the fused nucleotide sequences in the form of, for example, a suitable plasmid, so as to express a fusion polypeptide. The expression may be effected in vitro from, for example, prokaryotic or eukaryotic cells, or in vivo from, for example, a transgenic organism. In some embodiments of the present disclosure, the expression of the fusion protein is performed in mammalian cell lines, for example, CHO cell lines. Transformation is used broadly herein to refer to the genetic alteration of a cell resulting from the direct uptake, incorporation and expression of exogenous genetic material (exogenous DNA) from its surroundings and taken up through the cell membrane(s). Transformation occurs naturally in some species of bacteria, but it can also be affected by artificial means in other cells.

Furthermore, albumin itself may be modified to extend its circulating half-life. Fusion of the modified albumin to one or more Polypeptides of the present disclosure can be attained by the genetic manipulation/recombinant techniques described above or by chemical conjugation; the resulting fusion molecule has a half-life that exceeds that of fusions with non-modified albumin. (e.g., see WO2011/051489).

Well-established technology platforms exist for the genetic fusion and chemical conjugation of polypeptides (e.g., the Polypeptides described herein) and recombinant albumin. By way of example, the ALBUFUSE® flex platform (Novozymes Biopharma A/S; Denmark) can be used to effect the genetic fusion of one or more recombinant albumin molecules to one or more Polypeptides, thereby producing a contiguous cDNA encoding the Polypeptide(s) and the albumin(s) to generate a single homogeneous protein. The platform can be used with, for example, yeast and mammalian host expression systems. By way of further example, the RECOMBUMIN® Flex platform (Novozymes Biopharma A/S; Denmark) can be used to effect chemical conjugation of the Polypeptides of the present disclosure to recombinant albumin, without any further derivitization of the albumin. Although conjugation may be performed at several amino acid residues (e.g., lysine and tyrosine), the free thiol at Cys34 is a common strategy due to site specificity yielding a more homogenous final product.

Alternative Albumin Binding Strategies: Several albumin-binding strategies have been developed as alternatives for direct fusion, including albumin binding through a conjugated fatty acid chain (acylation). Because serum albumin is a transport protein for fatty acids, these natural ligands with albumin-binding activity have been used for half-life extension of small protein therapeutics. For example, insulin determir (LEVEMIR), an approved product for diabetes, comprises a myristyl chain conjugated to a genetically-modified insulin, resulting in a long-acting insulin analog.

The present disclosure also contemplates fusion proteins which comprise an albumin binding domain (ABD) polypeptide sequence and the sequence of one or more of the polypeptides described herein. Any ABD polypeptide sequence described herein or in the literature can be a component of the fusion proteins. The components of the fusion proteins can be optionally covalently bonded through a linker, such as those linkers described herein. In some of the embodiments of the present disclosure, the fusion proteins comprise the ABD polypeptide sequence as an N-terminal moiety and the Polypeptides described herein as a C-terminal moiety.

The present disclosure also contemplates fusion proteins comprising a fragment of an albumin binding polypeptide, which fragment substantially retains albumin binding; or a multimer of albumin binding polypeptides or their fragments comprising at least two albumin binding polypeptides or their fragments as monomer units.

Without wishing to be bound by any theory, it is believed that the polypeptides described herein bind to the ABD polypeptide sequence, thereby sequestering the polypeptides in a subject leading to increased duration of action in the subject.

For a general discussion of ABD and related technologies, see WO 2012/050923, WO 2012/050930, WO 2012/004384 and WO 2009/016043.

Fusion Proteins with Maltose Binding Protein or Fragments Thereof: The present disclosure also contemplates fusion proteins which comprise a maltose binding protein (MBP), or fragment thereof, and the amino acid sequence of one or more of the Polypeptides described herein. In some embodiments, the MBP fragment comprises a maltose binding domain (MBD). Any MBP, or fragment thereof, or MBD polypeptide sequence described herein or known in the art can be a component of the fusion proteins of the present disclosure. The components of the fusion proteins can be optionally covalently bonded through a linker, such as those linkers described herein. In some of the embodiments of the present disclosure, the fusion proteins comprise the MBP, or fragment thereof, or MBD polypeptide sequence as an N-terminal moiety and the polypeptides described herein as a C-terminal moiety.

The present disclosure also contemplates fusion proteins comprising a fragment of a MBP or MBD polypeptide, which fragment substantially retains maltose binding activity; or a multimer of maltose binding polypeptides, or fragments thereof (e.g., multimer of a MBD) comprising at least two maltose binding polypeptides, or fragments thereof, as monomer units (e.g., two or more MBD polypeptides).

For a general discussion of MBP and MBD and related technologies, see, e.g., Kapust et al. (1999) Protein Sci 8(8):1668-74.

Fc Fusion Proteins. The present disclosure also contemplates fusion proteins which comprise an Fc polypeptide or fragment thereof, and the amino acid sequence of one or more of the Polypeptides described herein (e.g., human GDF15 molecules, modified human GDF15 molecules, GDF15 muteins, and modified GDF15 muteins). Any Fc polypeptide sequence described herein or known in the art can be a component of the fusion proteins of the present disclosure. The components of the fusion proteins can be optionally covalently bonded through a linker, such as those linkers described herein. In some of the embodiments of the present disclosure, the fusion proteins comprise the Fc polypeptide sequence as an N-terminal moiety and the Polypeptides described herein as a C-terminal moiety.

The present disclosure also contemplates Fc polypeptide fusion partners, and fusion proteins comprising such, where the Fc polypeptide fusion partner is modified to be one partner of a charged Fc pair. A "partner of a charged Fc pair" refers to a (i) a "negatively charged" Fc sequence (optionally lacking the hinge region) and comprising a charged pair mutation or (ii) a "positively charged" Fc sequence (optionally lacking the hinge region) and comprising a charged pair mutation. "Positively charged" and "negatively charged" are used herein for ease of reference to describe the nature of the charge pair mutations in the Fc sequences, and not to indicate that the overall sequence or construct necessarily has a positive or negative charge. Charged Fc amino acid sequences suitable for use in Polypeptide constructs (e.g., GDF15 mutein, modified GDF15 muteins) of the present disclosure are described in, for example WO 2013/113008.

Examples of a positively charged Fc ("Fc(+)") include an Fc comprising an aspartic acid-to-lysine mutation (E356K) and a glutamic acid-to-lysine mutation (D399K) of an Fc sequence lacking the hinge region. Examples of a negatively charged Fc ("Fc(−)") include an Fc comprising two lysine-to-aspartate mutations (K392D, K409D) in an Fc sequence lacking the hinge region. The C-terminal lysine (K477) also may also be optionally deleted. When a Fc(+)Polypeptide fusion protein (e.g., Fc(+)GDF15 mutein fusion protein) and a Fc(−) Polypeptide fusion protein (e.g., Fc(−)GDF15 mutein fusion protein) are incubated together, the aspartate residues associate with the lysine residues through electrostatic force, facilitating formation of Fc heterodimers between the Fc(+) and the Fc(−) sequences of the GDF15 Polypeptide fusion proteins.

The present disclosure also contemplates constructs designated "hemi" or "hemiFc" constructs, which comprise two Fc sequences joined in tandem by a linker that connects the N-terminus of a first Fc sequence to the C-terminus of a second Fc sequence. In some embodiments, a monomer comprises a Polypeptide (e.g., a mature modified GDF15 or mutein GDF15) sequence linked to the first Fc sequence by a first linker that connects the N-terminus of the GDF15 sequence to the C-terminus of the first Fc sequence, wherein the first Fc sequence is linked to the second Fc sequence by a second linker that connects the N-terminus of the first Fc sequence to the C-terminus of the second Fc sequence. The first and second Fc sequences also are associated by the Fc hinge regions. Two such monomers associate to form a dimer in which the monomers are linked via an interchain disulfide bond between the two Polypeptide sequences. For examples of hemiFc polypeptides suitable for use with the GDF15 muteins of the present disclosure see WO 2013/113008.

The present disclosure also contemplates fusion proteins having a multimer of Fc polypeptides, or fragments thereof, including a partner of a charged Fc pair (e.g., multimer of an Fc).

Conjugation with Other Molecules: Additional suitable components and molecules for conjugation include, for example, thyroglobulin; tetanus toxoid; Diphtheria toxoid; polyamino acids such as poly(D-lysine:D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

Thus, the present disclosure contemplates conjugation of one or more additional components or molecules at the N- and/or C-terminus of a polypeptide sequence, such as another protein (e.g., a protein having an amino acid sequence heterologous to the subject protein), or a carrier molecule. Thus, an exemplary polypeptide sequence can be provided as a conjugate with another component or molecule.

A conjugate modification may result in a polypeptide sequence that retains activity with an additional or complementary function or activity of the second molecule. For example, a polypeptide sequence may be conjugated to a molecule, e.g., to facilitate solubility, storage, in vivo or shelf half-life or stability, reduction in immunogenicity, delayed or controlled release in vivo, etc. Other functions or activities include a conjugate that reduces toxicity relative to an unconjugated polypeptide sequence, a conjugate that targets a type of cell or organ more efficiently than an unconjugated polypeptide sequence, or a drug to further counter the causes or effects associated with a disorder or disease as set forth herein (e.g., diabetes).

A Polypeptide may also be conjugated to large, slowly metabolized macromolecules such as proteins; polysaccharides, such as sepharose, agarose, cellulose, cellulose beads; polymeric amino acids such as polyglutamic acid, polylysine; amino acid copolymers; inactivated virus particles; inactivated bacterial toxins such as toxoid from diphtheria, tetanus, cholera, leukotoxin molecules; inactivated bacteria; and dendritic cells. Such conjugated forms, if desired, can be used to produce antibodies against a polypeptide of the present disclosure.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Purification methods such as cation exchange chromatography may be used to separate conjugates by charge difference, which effectively separates conjugates into their various molecular weights. For example, the cation exchange column can be loaded and then washed with ~20 mM sodium acetate, pH ~4, and then eluted with a linear (0 M to 0.5 M) NaCl gradient buffered at a pH from about 3 to 5.5, e.g., at pH ~4.5. The content of the fractions obtained by cation exchange chromatography may be identified by molecular weight using conventional methods, for example, mass spectroscopy, SDS-PAGE, or other known methods for separating molecular entities by molecular weight.

Other Modifications: The present disclosure contemplates the use of other modifications, currently known or developed in the future, of the Polypeptides to improve one or more properties. One such method for prolonging the circulation half-life, increasing the stability, reducing the clearance, or altering the immunogenicity or allergenicity of a polypeptide of the present disclosure involves modification of the polypeptide sequences by hesylation, which utilizes hydroxyethyl starch derivatives linked to other molecules in order to modify the molecule's characteristics. Various aspects of hesylation are described in, for example, U.S. Patent Appln. Nos. 2007/0134197 and 2006/0258607.

The present disclosure also contemplates fusion molecules comprising SUMO as a fusion tag (LifeSensors, Inc.; Malvern, Pa.). Fusion of a polypeptide described herein to SUMO may convey several beneficial effects on the polypeptide, including enhancement of expression, improvement in solubility, and/or assistance in the development of purification methods. SUMO proteases recognize the tertiary structure of SUMO and cleave the fusion protein at the C-terminus of SUMO, thus releasing a polypeptide described herein with the desired N-terminal amino acid.

Linkers: Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules can be about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1, 2, 3, 4, 5, 6, 7, 8, 9, 10, 10-20, 20-30, 30-50 amino acids.

Exemplary flexible linkers include glycine polymers $(G)_n$, glycine-alanine polymers, alanine-serine polymers, glycine-serine polymers (for example, $(G_mS_o)_n$, $(GSGGS)_n$, $(G_m\text{-}S_oG_m)_n$, $(G_mS_oG_mS_oG_m)_n$, $(GSGGS_m)_n$, $(GSGS_mG)_n$ and $(GGGS_m)_n$, and combinations thereof, where m, n, and o are each independently selected from an integer of at least 1 to 20, e.g., 1-18, 2-16, 3-14, 4-12, 5-10, 1, 2, 3, 4, 5, 6, 7, 8, 9, or 10), and other flexible linkers. Glycine and glycine-serine polymers are relatively unstructured, and therefore may serve as a neutral tether between components. Exemplary flexible linkers include, but are not limited to GGSG, GGSGG, GSGSG, GSGGG, GGGSG, and GSSSG.

Additional flexible linkers include glycine polymers $(G)_n$ or glycine-serine polymers (e.g., $(GS)_n$, $(GSGGS)_n$, $(GGGS)_n$, and $(GGGGS)_n$, where n=1 to 50, for example, 1, 2, 3, 4, 5, 6, 7, 8, 9, 10, 10-20, 20-30, 30-50). Exemplary flexible linkers include, but are not limited to GGGS (SEQ ID NO: 40), GGGGS (SEQ ID NO: 41), GGSG (SEQ ID NO: 42), GGSGG (SEQ ID NO: 43), GSGSG (SEQ ID NO: 44), GSGGG (SEQ ID NO: 45), GGGSG (SEQ ID NO: 46), and GSSSG (SEQ ID NO: 47). A multimer (e.g., 1, 2, 3, 4, 5, 6, 7, 8, 9, 10, 10-20, 20-30, or 30-50) of these linker sequences may be linked together to provide flexible linkers that may be used to conjugate a heterologous amino acid sequence to the Polypeptides disclosed herein. As described herein, the heterologous amino acid sequence may be a signal sequence and/or a fusion partner, such as, albumin, Fc sequence, and the like.

Examples of linkers include, e.g., $(GGGGS)_n$, where n is an integer from 1 to about 10 (e.g., n=1, 2, 3, 4, 5, 6, 7, 8, 9, or 10); GGGSGGGSIEGR (SEQ ID NO: 48); GGGGG (SEQ ID NO: 49); EGGGS (SEQ ID NO: 50).

In some cases, the linker may be a cleavable linker, e.g., an enzymatically cleavable linker. In other cases, the linker may be a non-cleavable linker, e.g., a linker that is not cleaved enzymatically under normal physiological conditions in vivo.

For example, a proteolytically cleavable linker can include a matrix metalloproteinase (MMP) cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). Cleavage sequence of MMP-9 is Pro-X-X-Hy (wherein, X represents an arbitrary residue; Hy, a hydrophobic residue) (SEQ ID NO: 51), e.g., Pro-X-X-Hy-(Ser/Thr) (SEQ ID NO: 52), e.g., Pro-Leu/Gln-Gly-Met-Thr-Ser (SEQ ID NO: 53) or Pro-Leu/Gln-Gly-Met-Thr (SEQ ID NO: 54). Another example of a protease cleavage site is a plasminogen activator cleavage site, e.g., a urokinase-type plasminogen activator (uPA) or a tissue plasminogen activator (tPA) cleavage site. Specific examples of cleavage sequences of uPA and tPA include sequences comprising Val-Gly-Arg. Another example is a thrombin cleavage site, e.g., CGLVPAGSGP (SEQ ID NO: 55). Additional suitable linkers comprising protease cleavage sites include linkers comprising one or more of the following amino acid sequences: 1) SLLKSRMVPNFN (SEQ ID NO: 56) or SLLIARRMPNFN (SEQ ID NO: 57), cleaved by cathepsin B; SKLVQASASGVN (SEQ ID NO: 58) or SSYLKASDAPDN (SEQ ID NO: 59), cleaved by an Epstein-Barr virus protease; RPKPQQFFGLMN (SEQ ID NO: 60) cleaved by MMP-3 (stromelysin); SLRPLALWRSFN (SEQ ID NO: 61) cleaved by MMP-7 (matrilysin); SPQGIAGQRNFN (SEQ ID NO: 62) cleaved by MMP-9; DVDERDVRGFASFL (SEQ ID NO: 63) cleaved by a thermolysin-like MMP; SLPLGLWAPNFN (SEQ ID NO: 64) cleaved by matrix metalloproteinase 2(MMP-2); SLLI-FRSWANFN (SEQ ID NO: 65) cleaved by cathepsin L; SGVVIATVIVIT (SEQ ID NO: 66) cleaved by cathepsin D; SLGPQGIWGQFN (SEQ ID NO: 67) cleaved by matrix metalloproteinase 1(MMP-1); KKSPGRVVGGSV (SEQ ID NO: 68) cleaved by urokinase-type plasminogen activator; PQGLLGAPGILG (SEQ ID NO: 69) cleaved by membrane type 1 matrixmetalloproteinase (MT-MMP); HGPEGL-RVGFYESDVMGRGHARLVHVEEPHT (SEQ ID NO: 70) cleaved by stromelysin 3 (or MMP-11), thermolysin, fibroblast collagenase and stromelysin-1; GPQGLAGQRGIV (SEQ ID NO: 71) cleaved by matrix metalloproteinase 13 (collagenase-3); GGSGQRGRKALE (SEQ ID NO: 72) cleaved by tissue-type plasminogen activator(tPA); SLSAL-LSSDIFN (SEQ ID NO: 73) cleaved by human prostate-specific antigen; SLPRFKIIGGFN (SEQ ID NO: 74) cleaved by kallikrein (hK3); SLLGIAVPGNFN (SEQ ID NO: 75) cleaved by neutrophil elastase; and FFKNIVT-PRTPP (SEQ ID NO: 76) cleaved by calpain (calcium activated neutral protease).

FIG. 3 depicts amino acid sequence of two fusion proteins M1 (SEQ ID NO: 77) and M2 (SEQ ID NO: 78) contemplated herein. Fusion protein M1 includes contiguously from N-terminus to C-terminus, IgK signal sequence (lowercase) fused to HSA amino acid sequence fused with a (Gly-Gly-Gly-Gly-Ser)$_3$ linker (Underlined) to the N-Terminus of mature human GDF15 (Bolded). Fusion protein M2 includes contiguously from N-terminus to C-terminus, IgK signal sequence (lowercase) fused to HSA amino acid sequence fused with a (Gly-Gly-Gly-Gly-Ser)$_3$ linker (underlined) to the N-terminus of mature human GDF15 (bolded) containing a 3-amino acid (ΔARN) deletion.

FIG. 5 depicts amino acid sequence of two fusion proteins M3 (SEQ ID NO: 79) and M4 (SEQ ID NO: 80) contemplated herein. Fusion protein M3 includes contiguously from N-terminus to C-terminus, IgK signal sequence (lowercase) fused to HSA amino acid sequence fused with a (Gly-Gly-Gly-Gly-Ser)$_5$ linker (underlined) to the N-terminus of mature human GDF15 (bolded) amino acid sequence containing a 3-amino acid deletion (denoted ΔARN or ΔN3). Fusion protein M4 includes contiguously from N-terminus to C-terminus, IgK signal sequence (lowercase) fused to HSA amino acid sequence fused with a (Gly-Gly-Gly-Gly-Ser)$_5$ linker (underlined) to the N-terminus of mature human GDF15 (bolded) amino acid sequence containing a 6 amino acid truncation (ΔARNGDH) relative to the N-terminus of mature hGDF15.

The present invention also contemplates recombinant nucleic acid sequences encoding the sequences, Polypeptides and dimers described herein. In certain embodiments, the recombinant nucleic acid encodes a Polypeptide having a contiguous amino acid sequence that is at least 80%, 85%, 90%, 95%, 96%, 97%, 98%, 99%, or 100% identical to the amino acid sequence of SEQ ID NO: 1, where the contiguous amino acid sequence has at least one of the following pairs of substitutions relative to the corresponding amino acids in SEQ ID NO: 1:
  i) D5T and R21N or D5S and R21N;
  ii) R16N and H18T or R16N and H18S;
  iii) S23N and E25T or S23N and E25S;
  iv) S50N and F52T; S50N and F52S; F52N and A54T; or F52N and A54S;
  v) Q51N and R53T; Q51N and R53S; R53N and A55T; or R53N and A55S;
  vi) S64N and H66T; or S64N and H66S;
  vii) K91N and D93T; K91N and D93S; D93N and G95T; or D93N and G95S;
  viii) T94N and V96T; T94N and V96S; V96N and L98T; or V96N and L98S;

ix) S97N and Q99T; or S97N and Q99S; and x) A106N and D108T or A106N and D108S;

wherein the substitution creates one or more N-linked glycosylation consensus sites having the sequence NXS/T, where N is Asn; X is an amino acid other than proline; followed by either Ser (S) or Thr (T) and further wherein one or more N-linked glycosylation consensus sites when expressed are linked to an N-glycan. In a further embodiment, the recombinant nucleic acid encodes a Polypeptide that when expressed forms a dimer. In a further embodiment, the recombinant nucleic acid encodes a Polypeptide having an N-terminal truncations and/or C-terminal truncations relative to SEQ ID NO: 1. The truncations may be of 1, 2, 3, 4, 5, 6, 7, 8, 9, 10, 11, 12, 13, 14 or more amino acids relative to a reference Polypeptide, e.g., SEQ ID NO: 1. In a specific embodiment, the recombinant nucleic acid encodes a Polypeptide having a truncation of the first three N-terminal residues in GDF15 (ΔARN or ΔN3). In particular embodiments, the present disclosure contemplates recombinant nucleic acid molecules encoding a Polypeptide comprising an amino acid sequence selected from: SEQ ID NO: 2, SEQ ID NO: 4, SEQ ID NO: 8, SEQ ID NO: 9, SEQ ID NO: 10, SEQ ID NO: 13, SEQ ID NO: 14, SEQ ID NO: 17, SEQ ID NO: 18 or SEQ ID NO: 30 or an amino acid differing by up to 5 amino acids; wherein said Polypeptide when expressed contains at least one N-glycosylation site that is N-glycosylated. In specific embodiments, the present disclosure contemplates recombinant nucleic acid molecules encoding a Polypeptide comprising an amino acid sequence selected from: SEQ ID NO: 2, SEQ ID NO: 4, SEQ ID NO: 8, SEQ ID NO: 9, SEQ ID NO: 10, SEQ ID NO: 13, SEQ ID NO: 14, SEQ ID NO: 17, SEQ ID NO: 18 or SEQ ID NO: 30 or an amino acid differing by up to 2 amino acids; wherein said Polypeptide when expressed contains at least one N-glycosylation site that is N-glycosylated. In particular embodiments, the recombinant nucleic acid encodes a Polypeptide comprising an amino acid sequence selected from: SEQ ID NO: 81, SEQ ID NO: 83, SEQ ID NO: 87, SEQ ID NO: 88, SEQ ID NO: 89, SEQ ID NO: 92, SEQ ID NO: 93, SEQ ID NO: 96, SEQ ID NO: 97 or SEQ ID NO: 100 or an amino acid differing by up to 5 amino acids; wherein said Polypeptide when expressed contains at least one N-glycosylation site that is N-glycosylated. In particular embodiments, the recombinant nucleic acid encodes a Polypeptide comprising an amino acid sequence selected from: SEQ ID NO: 81, SEQ ID NO: 83, SEQ ID NO: 87, SEQ ID NO: 88, SEQ ID NO: 89, SEQ ID NO: 92, SEQ ID NO: 93, SEQ ID NO: 96, SEQ ID NO: 97 or SEQ ID NO: 100 or an amino acid differing by up to 2 amino acids; wherein said Polypeptide when expressed contains at least one N-glycosylation site that is N-glycosylated. The present disclosure also contemplates a method of making a modified GDF15 N-glycosylated homodimer comprising the step of expressing the foregoing recombinant nucleic acid in a mammalian cell, e.g., a CHO cell. The present disclosure also encompasses a modified GDF15 N-glycosylated homodimer made by the foregoing method.

In addition to the specific amino acid sequences and nucleic acid sequences provided herein, the disclosure also contemplates polypeptides and nucleic acids having sequences that are at least 80%, at least 85%, at least 90%, or at least 95% identical in sequence to the amino acid and nucleic acids. The terms "identical" or percent "identity," in the context of two or more polynucleotide sequences, or two or more amino acid sequences, refers to two or more sequences or subsequences that are the same or have a specified percentage of amino acid residues or nucleotides that are the same (e.g., at least 80%, at least 85%, at least 90%, or at least 95% identical over a specified region), when compared and aligned for maximum correspondence over a designated region. The disclosure specifically contemplates polypeptides having amino acid sequences that are at least 80%, at least 85%, at least 90%, at least 95%, at least 96%, at least 97%, at least 98%, or at least 99% identical in sequence to the amino acid sequence of SEQ ID NOs: 2-35 or 77-97.

Methods of Production of Polypeptides

A polypeptide of the present disclosure can be produced by any suitable method, including recombinant and non-recombinant methods (e.g., chemical synthesis).

A. Chemical Synthesis

Where a polypeptide is chemically synthesized, the synthesis may proceed via liquid-phase or solid-phase. Solid-phase peptide synthesis (SPPS) allows the incorporation of unnatural amino acids and/or peptide/protein backbone modification. Various forms of SPPS, such as Fmoc and Boc, are available for synthesizing polypeptides of the present disclosure. Details of the chemical synthesis are known in the art (e.g., Ganesan A. 2006 Mini Rev. Med. Chem. 6:3-10; and Camarero J. A. et al., 2005 Protein Pept Lett. 12:723-8).

Solid phase peptide synthesis may be performed as described hereafter. The α functions (Nα) and any reactive side chains are protected with acid-labile or base-labile groups. The protective groups are stable under the conditions for linking amide bonds but can be readily cleaved without impairing the peptide chain that has formed. Suitable protective groups for the a-amino function include, but are not limited to, the following: t-butyloxycarbonyl (Boc), benzyloxycarbonyl (Z), o-chlorbenzyloxycarbonyl, bi-phenylisopropyloxycarbonyl, tert-amyloxycarbonyl (Amoc), α,α-dimethyl-3,5-dimethoxy-benzyloxycarbonyl, o-nitrosulfenyl, 2-cyano-t-butoxy-carbonyl, 9-fluorenylmethoxycarbonyl (Fmoc), 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl (2-CIZ), 2,6-dichlorobenzyl, cyclohexyl, cyclopentyl, 1-(4,4-dimethyl-2,6-dioxocyclohex-1-ylidene)ethyl (Dde), isopropyl, 4-methoxy-2,3-6-trimethylbenzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers and the like. Polystyrene (1%)-divinylbenzene or TentaGel® derivatized with 4-benzyloxybenzyl-alcohol (Wang-anchor) or 2-chlorotrityl chloride can be used if it is intended to prepare the peptidic acid. In the case of the peptide amide, polystyrene (1%) divinylbenzene or Tenta-Gel® derivatized with 5-(4'-aminomethyl)-3',5'-dimethoxyphenoxy)valeric acid (PAL-anchor) or p-(2,4-dimethoxyphenyl-amino methyl)-phenoxy group (Rink amide anchor) can be used.

The linkage to the polymeric support can be achieved by reacting the C-terminal Fmoc-protected amino acid with the support material with the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Nα-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, o-acyl-ureas, benzotriazol-1-yl-Tris-pyrrolidino-phosphonium hexafluorophosphate (PyBOP) or other phosphonium salts, N-hydroxysuccinimides, other N-hydroxyimides or oximes in the presence or also in the absence of 1-hydroxybenzotriazole or 1-hydroxy-7-azabenzotriazole, e.g., with the aid of TBTU with addition of hydroxybenzotriazole (HOBt), with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, e.g., in a 2-fold excess and at temperatures between about 10° C. and 50° C., e.g., 25° C. in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Nα-Fmoc-amino acid, its acid chloride or acid fluoride under the conditions described above.

The Nα-protected amino acid (e.g., the Fmoc amino acid) can be coupled to the 2-chlorotrityl resin in dichloromethane with the addition of DIEA with reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Nα-Fmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Nα-Fmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethylsulfide, ethylmethylsulfide, thioanisole, thiocresol, m-cresol, anisole ethanedithiol, phenol or water, e.g., 15% v/v dimethylsulfide/ethanedithiol/m-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about –10° C. and 50° C. (e.g., about 25° C.), and reaction times between about 12 and 24 hours (e.g., about 18 hours). In addition the peptide can be cleaved from the support by re-esterification, e.g., with methanol.

The acidic solution that is obtained may be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecylsilylsilica (ODS) phases.

B. Recombinant Production

Where a polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., *E. coli*) or a yeast host cell, respectively. Other examples of eukaryotic cells that may be used as host cells include insect cells, mammalian cells, and/or plant cells. Where mammalian host cells are used, they may include human cells (e.g., HeLa, 293, H9 and Jurkat cells); mouse cells (e.g., NIH3T3, L cells, and C127 cells); primate cells (e.g., Cos 1, Cos 7 and CV1) and hamster cells (e.g., Chinese hamster ovary (CHO) cells). In specific embodiments, the Polypeptide is produced in CHO cells. In other embodiments, the Polypeptide is produced in a yeast cell and in particular embodiments may be a yeast cell genetically engineered to produce glycoproteins with mammalian-like N-glycans.

A variety of host-vector systems suitable for the expression of a polypeptide may be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid)

or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and may provide for inducible or constitutive expression where the coding region is operably-linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host may be present to facilitate selection of cells containing the vector. Moreover, the expression construct may include additional elements. For example, the expression vector may have one or two replication systems, thus allowing it to be maintained in organisms, for example, in mammalian or insect cells for expression and in a prokaryotic host for cloning and amplification. In addition, the expression construct may contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification methods. In one embodiment, the protein may be isolated using metal chelate chromatography methods. Proteins may contain modifications to facilitate isolation.

The polypeptides may be prepared in substantially pure or isolated form (e.g., free from other polypeptides). The polypeptides can be present in a composition that is enriched for the polypeptide relative to other components that may be present (e.g., other polypeptides or other host cell components). For example, purified polypeptide may be provided such that the polypeptide is present in a composition that is substantially free of other expressed proteins, e.g., less than 90%, less than 60%, less than 50%, less than 40%, less than 30%, less than 20%, less than 10%, less than 5%, or less than 1%, of the composition is made up of other expressed proteins.

Antibodies

The present disclosure provides antibodies, including isolated antibodies that specifically bind a polypeptide or fusion protein of the present disclosure. The term "antibody" encompasses intact monoclonal antibodies, polyclonal antibodies, multispecific antibodies (e.g., bispecific antibodies) formed from at least two intact antibodies, and antibody binding fragments including Fab and F(ab)'$_2$, provided that they specifically bind a polypeptide or fusion protein of the present disclosure. The basic whole antibody structural unit comprises a tetramer, and each tetramer is composed of two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. In contrast, the carboxy-terminal portion of each chain defines a constant region primarily responsible for effector function. Human light chains are classified as kappa and lambda, whereas human heavy chains are classified as mu, delta, gamma, alpha, or epsilon, and define the antibody's isotype as IgM, IgD, IgG, IgA, and IgE, respectively. Binding fragments are produced by recombinant DNA techniques, or by enzymatic or chemical cleavage of intact antibodies. Binding fragments include Fab, Fab', F(ab')$_2$, Fv, and single-chain antibodies.

Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Within light and heavy chains, the variable and constant regions are joined by a "J" region of about 12 or more amino acids, with the heavy chain also including a "D" region of about 10 more amino acids. The antibody chains all exhibit the same general structure of relatively conserved framework regions (FR) joined by three hyper-variable regions, also called "complementarity-determining regions" or "CDRs". The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4.

An intact antibody has two binding sites and, except in bifunctional or bispecific antibodies, the two binding sites are the same. A bispecific or bifunctional antibody is an artificial hybrid antibody having two different heavy/light chain pairs and two different binding sites. Bispecific antibodies can be produced by a variety of methods including fusion of hybridomas or linking of Fab' fragments.

As set forth above, binding fragments may be produced by enzymatic or chemical cleavage of intact antibodies. Digestion of antibodies with the enzyme papain results in two identical antigen-binding fragments, also known as "Fab" fragments, and an "Fc" fragment which has no antigen-binding activity. Digestion of antibodies with the enzyme pepsin results in a F(ab')$_2$ fragment in which the two arms of the antibody molecule remain linked and comprise two-antigen binding sites. The F(ab')$_2$ fragment has the ability to crosslink antigen.

As used herein, the term "Fab" refers to a fragment of an antibody that comprises VH and VL regions as well as the constant domain of the light chain and the CH1 domain of the heavy chain.

When used herein, the term "Fv" refers to the minimum fragment of an antibody that retains both antigen-recognition and antigen-binding sites. In a two-chain Fv species, this region includes a dimer of one heavy-chain and one light-chain variable domain in non-covalent association. In a single-chain Fv species, one heavy-chain and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. While the six CDRs, collectively, confer antigen-binding specificity to the antibody, even a single variable domain (or half of an Fv comprising only three CDRs specific for an antigen) has the ability to recognize and bind antigen.

When used herein, the term "complementarity determining regions" or "CDRs" refers to parts of immunological receptors that make contact with a specific ligand and determine its specificity.

The term "hypervariable region" refers to the amino acid residues of an antibody which are responsible for antigen-binding. The hypervariable region generally comprises amino acid residues from a CDR and/or those residues from a "hypervariable loop".

As used herein, the term "epitope" refers to binding sites for antibodies on protein antigens. Epitopic determinants usually comprise chemically active surface groupings of molecules such as amino acids or sugar side chains, as well as specific three-dimensional structural and charge characteristics. An antibody is said to bind an antigen when the dissociation constant is ≤1 μM, ≤100 nM, or ≤10 nM. An increased equilibrium constant ("$K_D$") means that there is less affinity between the epitope and the antibody, whereas a decreased equilibrium constant means that there is more affinity between the epitope and the antibody. An antibody with a $K_D$ of "no more than" a certain amount means that the antibody will bind to the epitope with the given $K_D$ or more strongly. Whereas $K_D$ describes the binding characteristics of an epitope and an antibody, "potency" describes the effectiveness of the antibody itself for a function of the antibody. There is not necessarily a correlation between an equilibrium constant and potency; thus, for example, a relatively low $K_D$ does not automatically mean a high potency.

The term "selectively binds" in reference to an antibody does not mean that the antibody only binds to a single substance, but rather that the $K_D$ of the antibody to a first substance is less than the $K_D$ of the antibody to a second substance. An antibody that exclusively binds to an epitope only binds to that single epitope.

When administered to humans, antibodies that contain rodent (i.e., murine or rat) variable and/or constant regions are sometimes associated with, for example, rapid clearance from the body or the generation of an immune response by the body against the antibody. In order to avoid the utilization of rodent-derived antibodies, fully human antibodies can be generated through the introduction of human antibody function into a rodent so that the rodent produces fully human antibodies. Unless specifically identified herein, "human" and "fully human" antibodies can be used interchangeably. The term "fully human" can be useful when distinguishing antibodies that are only partially human from those that are completely, or fully, human. The skilled artisan is aware of various methods of generating fully human antibodies.

In order to address possible human anti-mouse antibody responses, chimeric or otherwise humanized antibodies can be utilized. Chimeric antibodies have a human constant region and a murine variable region, and, as such, human anti-chimeric antibody responses may be observed in some patients. Therefore, it is advantageous to provide fully human antibodies against multimeric enzymes in order to avoid possible human anti-mouse antibody or human anti-chimeric antibody responses.

Fully human monoclonal antibodies can be prepared, for example, by the generation of hybridoma cell lines by techniques known to the skilled artisan. Other preparation methods involve the use of sequences encoding particular antibodies for transformation of a suitable mammalian host cell, such as a CHO cell. Transformation can be by any known method for introducing polynucleotides into a host cell, including, for example, packaging the polynucleotide in a virus (or into a viral vector) and transducing a host cell with the virus (or vector) or by transfection procedures known in the art. Methods for introducing heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. Mammalian cell lines available as hosts for expression are well known in the art and include, but are not limited to, CHO cells, HeLa cells, and human hepatocellular carcinoma cells.

The antibodies can be used to detect a polypeptide of the present disclosure. For example, the antibodies can be used as a diagnostic by detecting the level of one or more polypeptides of the present disclosure in a subject, and either comparing the detected level to a standard control level or to a baseline level in a subject determined previously (e.g., prior to any illness).

Another embodiment of the present disclosure entails the use of one or more human domain antibodies (dAb). dAbs are the smallest functional binding units of human antibodies (IgGs) and have favorable stability and solubility characteristics. The technology entails a dAb(s) conjugated to HSA (thereby forming a "AlbudAb"; see, e.g., EP1517921B, WO2005/118642 and WO2006/051288) and a molecule of interest (e.g., a polypeptide sequence of the present disclosure). AlbudAbs are often smaller and easier to manufacture in microbial expression systems, such as bacteria or yeast, than current technologies used for extending the serum half-life of polypeptides. As HSA has a half-life of about three weeks, the resulting conjugated molecule improves the half-life of the molecule of interest. Use of the dAb technology may also enhance the efficacy of the molecule of interest.

Therapeutic and Prophylactic Uses

The present disclosure provides methods for treating or preventing metabolic and metabolic-associated diseases, such as, obesity and other body weight disorders, hyperglycemia, hyperinsulinemia, glucose intolerance, and glucose metabolism disorders, by the administration of the Polypeptides, or compositions thereof, as described herein. Such methods may also have an advantageous effect on one or more symptoms associated with a disease, disorder or condition by, for example, decreasing the severity or the frequency of a symptom. In specific embodiments, the present disclosure provides methods for treating a glucose metabolism or body weight disorder by the administration of the Polypeptides, N-glycosylated dimers or compositions thereof. In particular embodiment, the present disclosure methods for reducing food intake or decreasing body weight by the administration of the Polypeptides, N-glycosylated dimers or compositions thereof. The present disclosure further provides a use of the foregoing sequences, Polypeptides, N-glycosylated dimers or compositions thereof in the manufacture of a medicament for use in treating a condition selected from metabolic and metabolic-associated diseases, such as, obesity and other body weight disorders, hyperglycemia, hyperinsulinemia, glucose intolerance, and glucose metabolism disorders. The present disclosure further provides a use of the foregoing sequences, Polypeptides, N-glycosylated dimers or compositions thereof in the manufacture of a medicament for use in treating a glucose metabolism or body weight disorder. The present disclosure further provides a use of the foregoing sequences, Polypeptides, N-glycosylated dimers or compositions thereof in the manufacture of a medicament for use in reducing food intake or body weight.

In order to determine whether a subject may be a candidate for the treatment or prevention of a body weight disorder (e.g., obesity) by the methods provided herein, parameters such as, but not limited to, the etiology and the extent of the subject's condition (e.g., how overweight the subject is compared to reference healthy individual) should be evaluated. For example, an adult having a BMI between ~25 and ~29.9 kg/m$^2$ may be considered overweight (pre-obese), while an adult having a BMI of ~30 kg/m$^2$ or higher may be considered obese. As discussed herein, the Polypeptides of the present invention can effect appetite suppression, for example, decrease appetite leading to a reduction in body weight.

In order to determine whether a subject may be a candidate for the treatment or prevention of hyperglycemia, hyperinsulinemia, glucose intolerance, and/or glucose disorders by the methods provided herein, various diagnostic methods known in the art may be utilized. Such methods include those described elsewhere herein (e.g., fasting plasma glucose (FPG) evaluation and the oral glucose tolerance test (oGTT)).

The polypeptides and fusion proteins provided herein when administered to a subject for treating or preventing metabolic and metabolic-associated diseases, such as, obesity and other body weight disorders, hyperglycemia, hyperinsulinemia, glucose intolerance, glucose metabolism disorders may lead to a reduction in blood glucose level, a reduction in body weight, and/or a reduction in food intake.

In certain embodiments, the polypeptides and fusion proteins contemplated herein may decrease blood glucose level, body weight, and/or food intake by at least 5% compared to that in the absence of administration of the polypeptides or fusion proteins. For example, polypeptides and fusion proteins contemplated herein may decrease blood glucose level, body weight, and/or food intake by at least 10%, 20%, 30%, 50%, 60%, 70%, 80%, or 90% as compared to that prior to the start of the treatment or prevention.

Pharmaceutical Compositions

The Polypeptides of the present disclosure may be in the form of compositions suitable for administration to a subject. In general, such compositions are "pharmaceutical compositions" comprising one or more polypeptides and one or more pharmaceutically acceptable or physiologically acceptable diluents, carriers or excipients. In certain embodiments, the Polypeptides are present in a therapeutically effective amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Furthermore, the pharmaceutical compositions may be used in combination with other therapeutically active agents or compounds (e.g., glucose lowering agents) as described herein in order to treat or prevent the diseases, disorders and conditions as contemplated by the present disclosure.

The pharmaceutical compositions typically comprise a therapeutically effective amount of at least one of the Polypeptides contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that could be used in the pharmaceutical compositions and dosage forms. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-Tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver the Polypeptides, including implants (e.g., implantable pumps) and catheter systems, both of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed including synthetic mono- or diglycerides. Moreover, fatty acids such as oleic acid find use in the preparation of injectables. Prolonged absorption of particular injectable formulations can be achieved by including an agent that delays absorption (e.g., aluminum monostearate or gelatin).

The pharmaceutical compositions containing the active ingredient (e.g., polypeptides of the present disclosure) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods of preparing liposomes are described in, for example, U.S. Pat. Nos. 4,235,871, 4,501,728, and 4,837,028. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally-occurring gums, for example, gum acacia or gum tragacanth; naturally-occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The present disclosure contemplates the administration of the polypeptides in the form of suppositories for rectal administration of the drug. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The polypeptides contemplated by the present disclosure may be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Contemplated herein is the use of Nano Precision Medical's depot delivery technology (Nano Precision Medical; Emeryville, Calif.). The technology utilizes a titania nanotube membrane that produces zero-order release rates of macromolecules, such as protein and peptide therapeutics. The biocompatible membrane is housed in a small, subcutaneous implant that provides long-term (e.g., up to one year), constant-rate delivery of therapeutic macromolecules. The technology is currently being evaluated for the delivery of GLP-1 agonists for the treatment of Type II diabetes. In certain embodiments, the Polypeptide(s) disclosed herein may be a formulation with a membrane. For example, the Polypeptide may be impregnated into the membrane or surrounded by the membrane. The membrane may be in shape of a disc, tube or sphere. In certain embodiments, the tube may be a nanotube or the sphere may be a nanosphere.

In some embodiments, the Polypeptides described herein may be administered to a subject by using an on-body delivery system that can be affixed to the patient and can deliver a predetermined dose of the Polypeptide to the patient. Exemplary on-body delivery systems include, patches or pumps. In certain cases, an on-body delivery systems such as the on-body injectors used for delivering Neulasta® may be used for administering the Polypeptides disclosed herein. In other embodiments, osmotic pumps, such as, implantable osmotic pumps (e.g., DUROS® pump or ALZET® Osmotic Pump) may be used to deliver a Polypeptide described herein to a patient.

Routes of Administration

The present disclosure contemplates the administration of the disclosed polypeptides, and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation.

Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

Regarding antibodies, in an exemplary embodiment an antibody or antibody fragment of the present disclosure is stored at 10 mg/ml in sterile isotonic aqueous saline solution for injection at 4° C. and is diluted in either 100 ml or 200 ml 0.9% sodium chloride for injection prior to administration to the subject. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via subcutaneous bolus injection.

The present disclosure contemplates methods wherein the Polypeptide or an antibody or antibody fragment of the present disclosure is administered to a subject at least twice daily, at least once daily, at least once every 48 hours, at least once every 72 hours, at least once weekly, at least once every 2 weeks, at least once monthly, at least once every 2 months, or at least once every 3 months, or less frequently.

Combination Therapy

The present disclosure contemplates the use of the polypeptides in combination with one or more active therapeutic agents or other prophylactic or therapeutic modalities. In such combination therapy, the various active agents frequently have different mechanisms of action. Such combination therapy may be especially advantageous by allowing a dose reduction of one or more of the agents, thereby reducing or eliminating the adverse effects associated with one or more of the agents; furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the polypeptides are administered or applied sequentially, e.g., where one agent is administered prior to one or more other agents. In other embodiments, the polypeptides are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The polypeptides of the present disclosure can be used in combination with other agents useful in the treatment, prevention, suppression or amelioration of the diseases, disorders or conditions set forth herein, including those that are normally administered to subjects suffering from obesity, eating disorder, hyperglycemia, hyperinsulinemia, glucose intolerance, and other glucose metabolism disorders.

The present disclosure contemplates combination therapy with numerous agents (and classes thereof), including 1) insulin, insulin mimetics and agents that entail stimulation of insulin secretion, including sulfonylureas (e.g., chlorpropamide, tolazamide, acetohexamide, tolbutamide, glyburide, glimepiride, glipizide) and meglitinides (e.g., mitiglinide, repaglinide (PRANDIN) and nateglinide (STARLIX)); 2) biguanides (e.g., metformin (GLUCOPHAGE), and its pharmaceutically acceptable salts, in particular, metformin hydrochloride, and extended-release formulations thereof, such as Glumetza™, Fortamet™, and GlucophageXR™) and other agents that act by promoting glucose utilization, reducing hepatic glucose production and/or diminishing intestinal glucose output; 3) alpha-glucosidase inhibitors (e.g., acarbose, voglibose and miglitol) and other agents that slow down carbohydrate digestion and consequently absorption from the gut and reduce postprandial hyperglycemia; 4) thiazolidinediones (e.g., rosiglitazone (AVANDIA), troglitazone (REZULIN), pioglitazone (ACTOS), glipizide, balaglitazone, rivoglitazone, netoglitazone, AMG 131, MBX2044, mitoglitazone, lobeglitazone, IDR-105, troglitazone, englitazone, ciglitazone, adaglitazone, darglitazone that enhance insulin action (e.g., by insulin sensitization) including insulin, and insulin mimetics (e.g., insulin degludec, insulin glargine, insulin lispro, insulin detemir, insulin glulisine and inhalable formulations of each), thus promoting glucose utilization in peripheral tissues; 5) glucagon-like-peptides including DPP-IV inhibitors (e.g., alogliptin, omarigliptin, linagliptin, vildagliptin (GALVUS) and sitagliptin (JANUVIA)) and Glucagon-Like Peptide-1 (GLP-1) and GLP-1 agonists and analogs (e.g., exenatide (BYETTA and ITCA 650 (an osmotic pump inserted subcutaneously that delivers an exenatide analog over a 12-month period;

Intarcia, Boston, Mass.)) and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); 6) and DPP-IV-resistant analogues (incretin mimetics), PPAR gamma agonists, PPAR alpha agonists such as fenofibric acid derivatives (e.g., gemfibrozil, clofibrate, ciprofibrate, fenofibrate, bezafibrate), dual-acting PPAR agonists (e.g., ZYH2, ZYH1, GFT505, chiglitazar, muraglitazar, aleglitazar, sodelglitazar, and naveglitazar), pan-acting PPAR agonists, PTP1B inhibitors (e.g., ISIS-113715 and TTP814), SGLT inhibitors (e.g., ASP1941, SGLT-3, empagliflozin, dapagliflozin, canagliflozin, BI-10773, PF-04971729, remogloflozin, TS-071, tofogliflozin, ipragliflozin, and LX-4211), insulin secretagogues, angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®) or other anti-hypertensive drugs such as LCZ 696, RXR agonists, glycogen synthase kinase-3 inhibitors, immune modulators, sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine); beta-3 adrenergic receptor agonists, llbeta-HSD1 inhibitors, neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116, 835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), cerivastatin, and fluvastatin (particularly the sodium salt sold in LESCOL®); a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; HDL-raising drugs, (e.g., niacin and nicotinic acid receptor agonists, and extended- or controlled-release versions thereof, and/or with an HMG-CoA reductase inhibitor; niacin receptor agonists such as acipimox and acifran, as well as niacin receptor partial agonists; glucagon receptor antagonists (e.g., MK-3577, MK-0893, LY-2409021 and KT6-971); bile acid sequestering agents (e.g., colestilan, colestimide, colesevelam hydrochloride, colestipol, cholestyramine, and dialkylaminoalkyl derivatives of a cross-linked dextran), acyl CoA:cholesterol acyltransferase inhibitors, (e.g., avasimibe); agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, evacetrapib, and torcetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); PCSK9 inhibitors; GPR-40 partial agonists; SCD modulators; inhibitors of fatty acid synthase; amylin and amylin analogues (e.g., pramlintide); including pharmaceutically acceptable salt forms of the above active agents where chemically possible.

Furthermore, the present disclosure contemplates combination therapy with agents and methods for promoting weight loss, such as agents that stimulate metabolism or decrease appetite, and modified diets and/or exercise regimens to promote weight loss.

The polypeptides of the present disclosure may be used in combination with one or more other agent in any manner appropriate under the circumstances. In one embodiment, treatment with the at least one active agent and at least one polypeptide of the present disclosure is maintained over a period of time. In another embodiment, treatment with the at least one active agent is reduced or discontinued (e.g., when the subject is stable), while treatment with the polypeptide(s) of the present disclosure is maintained at a constant dosing regimen. In a further embodiment, treatment with the at least one active agent is reduced or discontinued (e.g., when the subject is stable), while treatment with the polypeptide(s) of the present disclosure is reduced (e.g., lower dose, less frequent dosing or shorter treatment regimen). In yet another embodiment, treatment with the at least one active agent is reduced or discontinued (e.g., when the subject is stable), and treatment with the polypeptide(s) of the present disclosure is increased (e.g., higher dose, more frequent dosing or longer treatment regimen). In yet another embodiment, treatment with the at least one active agent is maintained and treatment with the polypeptide(s) of the present disclosure is reduced or discontinued (e.g., lower dose, less frequent dosing or shorter treatment regimen). In yet another embodiment, treatment with the at least one active agent and treatment with the polypeptide(s) of the present disclosure are reduced or discontinued (e.g., lower dose, less frequent dosing or shorter treatment regimen).

Dosing

The polypeptides of the present disclosure may be administered to a subject in an amount that is dependent upon, for example, the goal of the administration (e.g., the degree of resolution desired); the age, weight, sex, and health and physical condition of the subject to be treated; the nature of the polypeptide, and/or formulation being administered; the route of administration; and the nature of the disease, disorder, condition or symptom thereof (e.g., the severity of the dysregulation of glucose/insulin and the stage of the disorder). The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with absorption, distribution, metabolism, and excretion ("ADME"), taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the polypeptide(s) of the present disclosure may be an amount that, when administered in one or more doses to a subject, produces a desired result relative to a healthy subject. For example, an effective dose may be one that, when administered to a subject having elevated plasma glucose and/or plasma insulin, achieves a desired reduction relative to that of a healthy subject by at least about 10%, at least about 20%, at least about 25%, at least about 30%, at least about 40%, at least about 50%, at least about 60%, at least about 70%, at least about 80%, or more than 80%.

An appropriate dosage level will generally be about 0.001 to 100 mg/kg of patient body weight per day, which can be administered in single or multiple doses. In some embodiments, the dosage level will be about 0.01 to about 25 mg/kg per day, and in other embodiments about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient. The polypeptide(s) may be administered on a regimen of, for example, 1 to 4 times per day, and often once or twice per day.

The dosage of the polypeptide(s) of the present disclosure may be repeated at an appropriate frequency, which may be in the range of once per day to once every three months, depending on the pharmacokinetics of the polypeptide(s) (e.g. half-life) and the pharmacodynamic response (e.g. the duration of the therapeutic effect of the polypeptide(s)). In some embodiments, dosing is frequently repeated between once per week and once every 3 months. In other embodiments, polypeptide(s) are administered approximately once per month.

In certain embodiments, the dosage of the disclosed polypeptide(s) is contained in a "unit dosage form". The phrase "unit dosage form" refers to physically discrete units, each unit containing a predetermined amount of a polypeptide(s) of the present disclosure, either alone or in combination with one or more additional agents, sufficient to produce the desired effect. It will be appreciated that the parameters of a unit dosage form will depend on the particular agent and the effect to be achieved.

Kits

The present disclosure also contemplates kits comprising the disclosed polypeptide(s), and pharmaceutical compositions thereof. The kits are generally in the form of a physical structure housing various components, as described below, and may be utilized, for example, in practicing the methods described above (e.g., administration of a polypeptide(s) to a subject in need of weight reduction).

A kit can include one or more of the polypeptide(s) disclosed herein (provided in, e.g., a sterile container), which may be in the form of a pharmaceutical composition suitable for administration to a subject. The polypeptide(s) can be provided in a form that is ready for use or in a form requiring, for example, reconstitution or dilution prior to administration. When the polypeptide(s) are in a form that needs to be reconstituted by a user, the kit may also include buffers, pharmaceutically acceptable excipients, and the like, packaged with or separately from the polypeptide(s). When combination therapy is contemplated, the kit may contain the several agents separately or they may already be combined in the kit. Each component of the kit can be enclosed within an individual container and all of the various containers can be within a single package. A kit of the present disclosure can be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampoule, tube or vial). Exemplary instructions include those for reducing or lowering blood glucose, treatment of hyperglycemia, treatment of diabetes, etc. with the disclosed Modulators, and pharmaceutical compositions thereof Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal (ly); s.c.=subcutaneous(ly); bid=twice daily; HPLC=high performance liquid chromatography; BW=body weight; U=unit; ns=not statistically significant; PG=fasting plasma glucose; FPI=fasting plasma insulin; ITT=insulin tolerance test; PTT=pyruvate tolerance test; oGTT=oral glucose tolerance test; GSIS=glucose-stimulated insulin secretion; PBS=phosphate-buffered saline; PCR=polymerase chain reaction; NHS=N-Hydroxysuccinimide; DMEM=Dulbeco's Modification of Eagle's Medium; GC=genome copy; EDTA=ethylenediaminetetraacetic acid.

Materials and Methods

The following methods and materials were used in the Examples below:

Animals. Diet-induced obese (DIO) male C57BL/6J mice (The Jackson Laboratory, Bar Harbor, Me.) were maintained on a high-fat diet (D12492, Research Diets, Inc., New Brunswick, N.J.) containing 60 kcal % fat, 20 kcal % protein and 20 kcal % carbohydrate for 12-20 weeks. All animal studies were approved by the NGM Institutional Animal Care and Use Committee. DIO C57BL/6J mice offer a human-like model of obesity, where the obesity is based upon excessive intake of calories. C57BL/6J mice are obesity-prone in which pronounced weight gain, as well as hyperinsulinemia and sometimes hyperglycemia is observed. This strain is most-commonly used mouse strain for modeling diet-induced obesity. (Nilsson C., et al., Acta Pharmacologica Sinica (2012) 33: 173-181).

Nucleic Acid and Amino Acid Sequences. GenBank Accession No. BC000529.2 sets forth the cDNA of ORF encoding human GDF15 variants, and GenBank Accession No. NP_004855.2 sets forth the amino acid sequence encoded by the cDNA. *Homo sapiens* serum albumin cDNA was purchased from Origene (SC319937), GeneBank Accession No. NM_000477.3, NP_000468).

A Kozak element and human IgK-Signal Peptide sequence (5'CACCATGGACATGAGGGTCCCCGCTCA-GCTCCTGGGGCTCCTGCTACTCTGGCTCCGAGGT-GCCAGATGT3') (SEQ ID NO: 98) was inserted into pTT5 vector (National Research Council Canada) between the PmeI and EcoRI site. While both restriction sites were eliminated an AgeI site was created for further in-frame cloning. To create the hIgK-GDF15 construct, GDF15 DNA was amplified by PCR using forward primer: 5'-CTC-CGAGGTGCCAGATGTGCGCGCAACGGGGACCACT-GTCCGCTCGGG 3' (SEQ ID NO: 102) and reverse primer: 5'-CCTCGAGCGGCCGCTAGCTCATATGCAGTGGCA-GTCTTTGGCTAACAA 3' (SEQ ID NO: 99) and Sapphire PCR mix (Clontech). The PCR product was gel-purified (Qiagen Gel Extraction kit) and cloned into pTT5-hIgK (linearized with AgeI/HindIII) using In-Fusion (Clontech). To create the hIgK-HSA-linker-GDF15 construct, HSA-linker and GDF15 were amplified by PCR individually using appropriate primers. After gel-purification, the two PCR fragments and linearized pTT5 vector were assembled using Gibson Assembly Master Mix. Stellar or NEB 5α-cells were transformed with In-Fusion and Gibson reactions respectively, plated on LB-agar plates containing carbenicillin and incubated over night at 37° C. Single colonies were picked and analyzed by sequencing. DNA from positive colonies was purified (DNA-Maxi-prep, Qiagen), fully sequence confirmed and used to transfect mammalian cells for recombinant protein expression.

To create specific muteins, site directed mutagenesis was performed with QuikChange Lightning kit (Agilent) and appropriate primers.

Transient Expression. All GDF15 muteins were transiently transfected in Expi 293F cells (Invitrogen Corporation, Carlsbad, Calif.). Cells were routinely sub-cultured in Expi expression medium (Invitrogen) and maintained as suspension cultures in shake flasks of varying sizes. Typically, cells were sub-cultured at a cell density of 5e5 viable cells/ml and grown for 3 days before sub-culturing. The flasks were maintained in a humidified $CO_2$ incubator maintained at 37° C. and 5% $CO_2$ level. Cells were maintained on New Brunswick shaker platforms (New Brunswick Scientific Company, Edison, N.J.) at an agitation rate of 120 RPM.

Transfections were performed when the cell density of the culture reached 2.5e6 viable cells/ml at greater than 95% viability. Typically, for 50 ml transfection, 2.5e6 cells/ml×50 ml cells were inoculated in a 250 ml shake flask in 42.5 ml culture volume. 50 μg plasmid DNA consisting of expression vector containing the gene of interest was first diluted in 2.5 ml OPTI-MEM reduced serum medium (Invitrogen). At the same time Expifectamine transfection reagent (Invitrogen), 2.67 times the volume (of plasmid DNA amount) was also diluted in 2.5 ml OPTI-MEM reduced serum medium. After a 5 minute incubation at room temperature, the diluted transfection reagent was added slowly to the diluted plasmid DNA to form transfection competent complexes. After an incubation period of 20 minutes at room temperature, 5 ml of the transfection complex was added to the 42.5 ml cell culture. The transfected cells were then placed in the humidified $CO_2$ incubator on an orbital shaker maintained at 120 RPM. Twenty-four hours post-transfection, the transfected culture was fed with 250 μl enhancer 1 solution (Invitrogen) and 2.5 ml enhancer 2 solution (Invitrogen). The culture was then re-placed in the humidified $CO_2$ incubator on an orbital shaker. 6-7 days post-transfection, cultures were harvested by centrifugation at 3000 RPM for 30 min before being filtered through a 0.2 μm filter (Nalgene). Samples were then analyzed on a coomassie stain gel for expression.

Stable CHO Cell Expression. GDF15 muteins were expressed stably from the GS Xceed System with the CHOK1SV GS-KO host cell line which is based on Lonza's well-established expression system for CHOK1SV cells. The GS Xceed System enables high expressing cell lines to be generated that are suitable for cGMP manufacture. The system includes cGMP banked CHOK1SV GS-KO host cells, GS expression vectors, full protocols for cell culture, transfection, selection and screening of cell lines, and v8 production processes (media and feeds). In developing cell lines for GDF15 muteins, the manufacturer's suggested recommendations were following in order to establish uncloned cell lines first. The uncloned cell lines were then subjected to limited dilution cloning to isolate high expressing single cell clones.

Purification of GDF15 Recombinant Protein. HSA-GDF15 fusions were purified from cultured media using blue sepharose affinity capture or Ion-change capture. In both cases, HSA-GDF15 fusions were eluted using a gradient of appropriate salt/pH conditions conducive for optimal elution and separation from Host Cell Protein impurities. All HSA-GDF15 fusions were then further purified using a GE Healthcare Superdex 200 (26/60) column using 1×PBS as running buffer. Purified fusions were further characterized and sequence confirmed with LC/MS (Agilent 6500-series Q-TOF), monodispersity confirmed via Gel-filtration-HPLC (Agilent 1200-HPLC) and SDS-PAGE gel (non-reduced and reduced) with coomassie and/or silver staining. For in vivo experiments, Endotoxin was confirmed to be less than 5EU/mg for sub-cutaneous injection.

GDF15 Glycosylation muteins were purified from cultured media using ion-exchange capture. In all cases, GDF15 muteins were eluted using a gradient of appropriate salt/pH conducive for optimal elution and separation from host cell protein impurities. All GDF15 muteins were then further purified using GE HiTrap Phenyl HP at pH 8.0 using a decreasing linear gradient of ammonium sulfate. Fractions were assessed and pooled based on purity and glycosylation properties via gel-shift on non-reduced SDS-PAGE gels. Final pools of each GDF15 mutein were then further characterized and sequence/glycan confirmed (+/−PNGase F, NEB Cat. #P0704S) with LC/MS (Agilent 6500-series Q-TOF), monodispersity confirmed via Gel-filtration-HPLC (Agilent 1200-HPLC) and SDS-PAGE gel (non-reduced and reduced) with coomassie and/or silver staining. All GDF15 muteins were formulated in 10 mM Sodium Acetate pH 4.0.

Solubility Assessment of Human GDF15 Muteins. Muteins were dialyzed into 0.01% (v/v) formic acid (pH 2.0) and concentrated using Amicon Ultra Centrifugal Filters composed of Regenerated Nitrocellulose 10,000 NMWL (UFC901096), in some cases greater than 10 mg/mL. The starting concentration for each mutein was determined using Absorbance at 280 nm wavelength and Beer's law (Extinction coefficient=14400, Molecular weight=12,287 Da). Each mutein was then serial diluted 2-fold back into 0.01% formic acid and 90 μL of each dilution was added to a 96-well plate. 10 μL of 10×PBS (containing 0.5M Tris pH 7.0) was added to each well and pH was confirmed to be 7. Following incubation at room temperature overnight with shaking, turbidity was measured at 370 nm. The inflection point at which turbidity begins to occur is accepted as the maximum solubility for each mutein. Muteins were categorized into one of five groups depending on their level of solubility: <0.2 mg/mL=+; ≥0.2 mg/mL=++; ≥0.5 mg/mL=+++; ≥1.0 mg/mL=++++; ≥5.0 mg/mL=+++++.

Example 1

Engineering of a Stabilized HSA-GDF15 Fusion Molecule

Expression of construct M1 displayed production challenges in a CHOK1SV GSKO stable cell line (FIG. 4). Significant clipping of the HSA-GDF15 dimeric fusion molecule was observed in the cell culture media. Clipped species were isolated using ion-exchange and/or hydrophobic interaction chromatography and/or gel filtration to produce a source of enriched species for further characterization. Following LC/MS analysis on an Agilent 6500-series Q-TOF, sites of clipping were evident in the C-terminus of the HSA fusion, the linker, and in the N-terminus of GDF15. Major species from construct M1 were identified as follows (linker=underlined, GDF15=bold):

```
Species 1 (SEQ ID NO: 103):
DAHKSEVAHRFKDLGEENFKALVLIAFAQYLQQCPFEDHVKLVNEVTEF

AKTCVADESAENCDKSLHTLFGDKLCTVATLRETYGEMADCCAKQEPER

NECFLQHKDDNPNLPRLVRPEVDVMCTAFHDNEETFLKKYLYEIARRHP

YFYAPELLFFAKRYKAAFTECCQAADKAACLLPKLDELRDEGKASSAKQ

RLKCASLQKFGERAFKAWAVARLSQRFPKAEFAEVSKLVTDLTKVHTEC

CHGDLLECADDRADLAKYICENQDSISSKLKECCEKPLLEKSHCIAEVE

NDEMPADLPSLAADFVESKDVCKNYAEAKDVFLGMFLYEYARRHPDYSV

VLLLRLAKTYETTLEKCCAAADPHECYAKVFDEFKPLVEEPQNLIKQNC

ELFEQLGEYKFQNALLVRYTKKVPQVSTPTLVEVSRNLGKVGSKCCKHP

EAKRMPCAEDYLSVVLNQLCVLHEKTPVSDRVTKCCTESLVNRRPCFSA

LEVDETYVPKEFNAETFTFHADICTLSEKERQIKKQTALVELVKHKPKA

TKEQLKAVMDDFAAFVEKCCKADDKETCFAEEGKKLVA

Species 2 (SEQ ID NO: 104):
DAHKSEVAHRFKDLGEENFKALVLIAFAQYLQQCPFEDHVKLVNEVTEF

AKTCVADESAENCDKSLHTLFGDKLCTVATLRETYGEMADCCAKQEPER

NECFLQHKDDNPNLPRLVRPEVDVMCTAFHDNEETFLKKYLYEIARRHP

YFYAPELLFFAKRYKAAFTECCQAADKAACLLPKLDELRDEGKASSAKQ

RLKCASLQKFGERAFKAWAVARLSQRFPKAEFAEVSKLVTDLTKVHTEC

CHGDLLECADDRADLAKYICENQDSISSKLKECCEKPLLEKSHCIAEVE

NDEMPADLPSLAADFVESKDVCKNYAEAKDVFLGMFLYEYARRHPDYSV

VLLLRLAKTYETTLEKCCAAADPHECYAKVFDEFKPLVEEPQNLIKQNC

ELFEQLGEYKFQNALLVRYTKKVPQVSTPTLVEVSRNLGKVGSKCCKHP

EAKRMPCAEDYLSVVLNQLCVLHEKTPVSDRVTKCCTESLVNRRPCFSA

LEVDETYVPKEFNAETFTFHADICTLSEKERQIKKQTALVELVKHKPKA

TKEQLKAVMDDFAAFVEKCCKADDKETCFAEEGKKLVAASQAALG

Species 3 (SEQ ID NO: 105):
DAHKSEVAHRFKDLGEENFKALVLIAFAQYLQQCPFEDHVKLVNEVTEF

AKTCVADESAENCDKSLHTLFGDKLCTVATLRETYGEMADCCAKQEPER
```

-continued
NECFLQHKDDNPNLPRLVRPEVDVMCTAFHDNEETFLKKYLYEIARRHP

YFYAPELLFFAKRYKAAFTECCQAADKAACLLPKLDELRDEGKASSAKQ

RLKCASLQKFGERAFKAWAVARLSQRFPKAEFAEVSKLVTDLTKVHTEC

CHGDLLECADDRADLAKYICENQDSISSKLKECCEKPLLEKSHCIAEVE

NDEMPADLPSLAADFVESKDVCKNYAEAKDVFLGMFLYEYARRHPDYSV

VLLLRLAKTYETTLEKCCAAADPHECYAKVFDEFKPLVEEPQNLIKQNC

ELFEQLGEYKFQNALLVRYTKKVPQVSTPTLVEVSRNLGKVGSKCCKHP

EAKRMPCAEDYLSVVLNQLCVLHEKTPVSDRVTKCCTESLVNRRPCFSA

LEVDETYVPKEFNAETFTFHADICTLSEKERQIKKQTALVELVKHKPKA

TKEQLKAVMDDFAAFVEKCCKADDKETCFAEEGKKLVAASQAALGL<u>G</u>

It is noted that species 3 includes the mature human serum albumin amino acid sequence and one (first) amino acid of the linker sequence. Species 1 and 2 are missing the last eight amino acids and last one amino acid at the C-terminus of the mature human serum albumin amino acid sequence.

Species 4 (SEQ ID NO: 106):
DAHKSEVAHRFKDLGEENFKALVLIAFAQYLQQCPFEDHVKLVNEVTEF

AKTCVADESAENCDKSLHTLFGDKLCTVATLRETYGEMADCCAKQEPER

NECFLQHKDDNPNLPRLVRPEVDVMCTAFHDNEETFLKKYLYEIARRHP

YFYAPELLFFAKRYKAAFTECCQAADKAACLLPKLDELRDEGKASSAKQ

RLKCASLQKFGERAFKAWAVARLSQRFPKAEFAEVSKLVTDLTKVHTEC

CHGDLLECADDRADLAKYICENQDSISSKLKECCEKPLLEKSHCIAEVE

NDEMPADLPSLAADFVESKDVCKNYAEAKDVFLGMFLYEYARRHPDYSV

VLLLRLAKTYETTLEKCCAAADPHECYAKVFDEFKPLVEEPQNLIKQNC

ELFEQLGEYKFQNALLVRYTKKVPQVSTPTLVEVSRNLGKVGSKCCKHP

EAKRMPCAEDYLSVVLNQLCVLHEKTPVSDRVTKCCTESLVNRRPCFSA

LEVDETYVPKEFNAETFTFHADICTLSEKERQIKKQTALVELVKHKPKA

TKEQLKAVMDDFAAFVEKCCKADDKETCFAEEGKKLVAASQAALGL<u>GGG</u>

<u>GSGGGGSGGGGS</u>AR

Species 5 (SEQ ID NO: 107):
DAHKSEVAHRFKDLGEENFKALVLIAFAQYLQQCPFEDHVKLVNEVTEF

AKTCVADESAENCDKSLHTLFGDKLCTVATLRETYGEMADCCAKQEPER

NECFLQHKDDNPNLPRLVRPEVDVMCTAFHDNEETFLKKYLYEIARRHP

YFYAPELLFFAKRYKAAFTECCQAADKAACLLPKLDELRDEGKASSAKQ

RLKCASLQKFGERAFKAWAVARLSQRFPKAEFAEVSKLVTDLTKVHTEC

CHGDLLECADDRADLAKYICENQDSISSKLKECCEKPLLEKSHCIAEVE

NDEMPADLPSLAADFVESKDVCKNYAEAKDVFLGMFLYEYARRHPDYSV

VLLLRLAKTYETTLEKCCAAADPHECYAKVFDEFKPLVEEPQNLIKQNC

ELFEQLGEYKFQNALLVRYTKKVPQVSTPTLVEVSRNLGKVGSKCCKHP

EAKRMPCAEDYLSVVLNQLCVLHEKTPVSDRVTKCCTESLVNRRPCFSA

LEVDETYVPKEFNAETFTFHADICTLSEKERQIKKQTALVELVKHKPKA

TKEQLKAVMDDFAAFVEKCCKADDKETCFAEEGKKLVAASQAALGL<u>GGG</u>

<u>GSGGGGSGGGGS</u>ARN

To minimize and correct the clipping issue observed near the linker region of the fusion molecule, a construct M2 was designed equivalent to construct M1, however with a truncation of the first three N-terminal residues in GDF15 (ΔARN or ΔN3) (FIG. 3). The resulting stabilized M2 construct when expressed in a CHOK1SV GSKO stable cell line, displayed minimal clipping issues as observed for M1 when comparing the conditioned media for each expressed construct. FIG. 4 demonstrates the significant clipping observed for M1 and the stability of construct M2.

Based on the stability enhancement observed for construct M2, further engineering was achieved for optimal linker length and clipping potential. Optimized linker length of [(G$_4$S)]$_5$ was achieved and coupled with GDF15 N-terminal deletions of either 3 residues (M3-ΔARN or ΔN3) or 6 residues (M4-ΔARNGDH or ΔN6) (see FIG. 5).

Example 2

Effects of Stability Enhanced HSA-GDF15 Fusion Molecules on Body Weight and Food Intake in DIO Mouse Model The effects of a subcutaneously administered fusion molecule having recombinant HSA fused to recombinant human GDF15 on body weight and food intake were evaluated over a 7 day period. Briefly, the fusion proteins M1 (FIGS. 3), M3 and M4 (FIG. 5) were administered, at doses of 4 nmol/kg, 12 nmol/kg and 40 nmol/kg, as a single subcutaneous bolus injection (10 mL/kg) to DIO mice weighing approximately 38 g-40 g. Following administration of vehicle control or the fusion proteins, body weight and food intake were monitored 24 hours and 7 days post-dose to monitor efficacy. The results obtained for the DIO mice administered 40 nmol/kg dose are presented in FIGS. 6 and 7.

Figure 6:
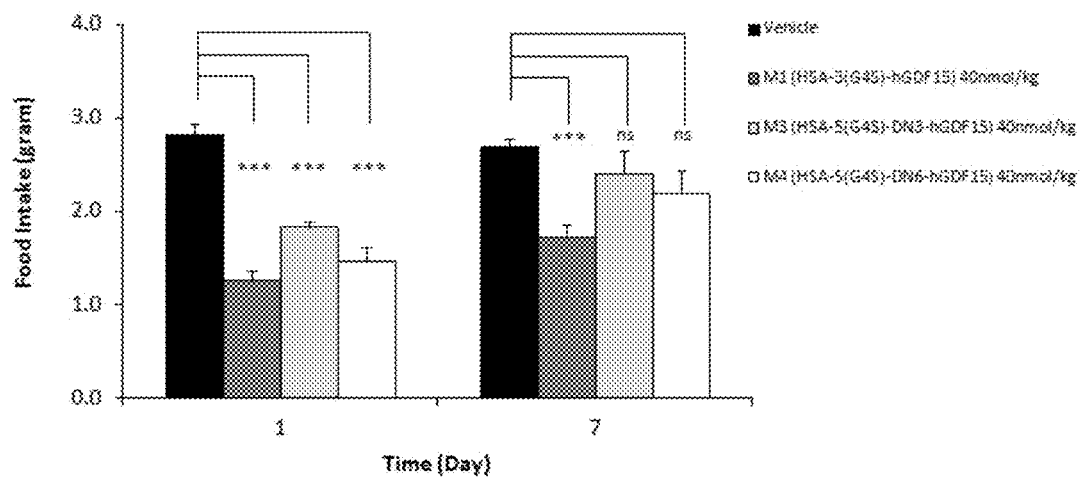
FIG. 6 depicts the effect on food intake in Diet-induced obese (DIO) mice following a single acute sub-cutaneous administration of vehicle, M1, M3 and M4 fusion molecules (40 nmol/kg). As noted in the figure, the food intake parameters were determined at 24 hours post-dose and 7 days post dose. In each group of mice, n=8 and p-values (*, p<0.05; , p<0.01; *, p<0.001) were determined by unpaired T-test comparing the various dose groups to vehicle control group at each specified time point.

As depicted in FIG. 6, administration of the fusion proteins at a dose of 40 nmol/kg (4 nmol/kg and 12 nmol/kg not shown) resulted in significant improvement in food intake reduction. In each group of mice, n=8 and p-values (*, $p<0.05$; , $p<0.01$; *, $p<0.001$, ns=not significant) were determined by student's unpaired T-test comparing the food intake at the various concentrations to vehicle control group at each specified time point.

Referring to FIG. 6, 24 hours (1 Day) post-administration of the fusion proteins vs vehicle control resulted in the following food intake reductions (Vehicle=2.8 g+/−0.13 g): 4 nmol/kg dose group (M1=1.9 g+/−0.25 g, ; M3=1.8 g+/−0.18 g, *; M4=1.8 g+/−0.10 g, *), 12 nmol/kg dose group (M1=1.5 g+/−0.19 g, *; M3=1.9 g+/−0.16 g, *; M4=1.7 g+/−0.12 g, *), and 40 nmol/kg dose group (M1=1.3 g+/−0.11 g, *; M3=1.8 g+/−0.06 g, *; M4=1.5 g+/−0.15 g, *). 7 days post-administration of the fusion molecules vs vehicle control resulted in the following food intake reduction reductions (Vehicle=2.7 g+/−0.09 g): 4 nmol/kg dose group (M1=2.0+/−0.18 g,; M3=2.5 g+/−0.08 g, ns; M4=2.5 g+/−0.09 g, ns), 12 nmol/kg dose group (M1=2.0 g+/−0.20 g, **; M3=2.2 g+/−0.17 g, *; M4=2.4 g+/−0.28 g, ns) and 40 nmol/kg dose group (M1=1.7 g+/−0.14 g, ***; M3=2.4 g+/−0.25 g, ns; M4=2.2 g+/−0.24 g, ns).

Figure 7:
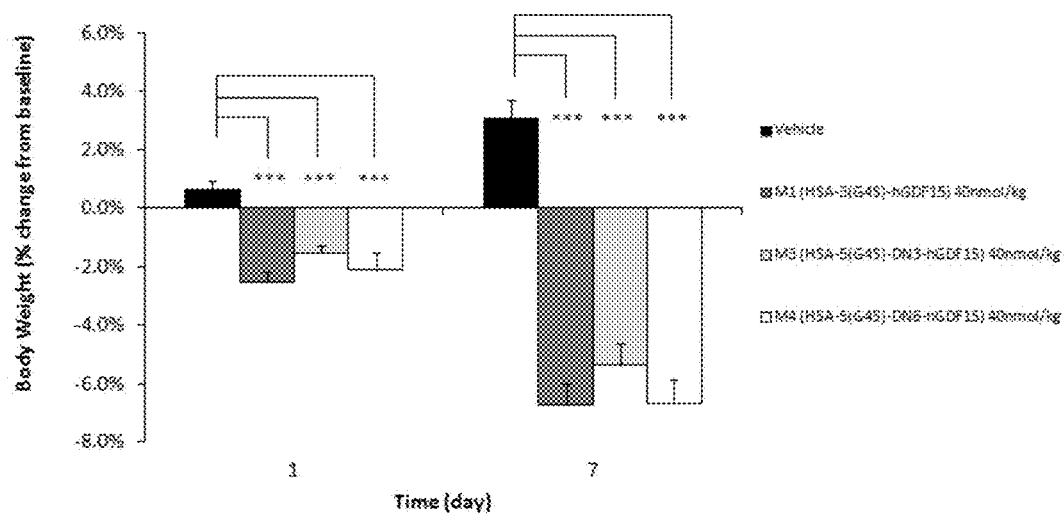
FIG. 7 depicts the effect on body weight in DIO mice following a single acute sub-cutaneous administration of vehicle, M1, M3 and M4 fusion molecules (40 nmol/kg). As noted in the figure, the body weight parameters were determined at 24 hours post-dose and 7 days post dose vs. pre-dose group weights. In each group of mice, n=8 and p-values (*, p<0.05; , p<0.01; *, p<0.001) were determined by unpaired T-test comparing the various dose groups to vehicle control group at each specified time point.

As depicted in FIG. 7, administration of the fusion molecules at a dose of 40 nmol/kg (4 nmol/kg and 12 nmol/kg not shown) resulted in significant reduction in body weight. In each group of mice, n=8 and p-values (*, $p<0.05$;

\*\*, p<0.01; \*\*\*, p<0.001, ns=not significant) were determined by student's unpaired T-test comparing the food intake at the various concentrations to vehicle control group at each specified time point.

Referring to FIG. 7, at time of dosing (Day=0) pre-administration of the fusion molecules vs vehicle control, the following body weights were recorded (Vehicle=39.0 g+/−0.92 g): 4 nmol/kg dose group (M1=39.2 g+/−0.66 g; M3=39.4 g+/−0.91 g; M4=39.3 g+/−0.77 g), 12 nmol/kg dose group (M1=39.4 g+/−0.78 g; M3=39.3 g+/−1.09 g; M4=39.3 g+/−0.81 g), and 40 nmol/kg dose group (M1=39.2 g+/−0.64 g; M3=39.2 g+/−0.68 g; M4=38.9 g+/−0.60 g). 24 hours (Day=1) post-administration of the fusion molecules vs vehicle control, the following body weights were recorded (% decrease=Delta difference vs. pre-administration dose group weight). Vehicle=+0.3 g+/−0.11 g, +0.6%), 4 nmol/kg dose group (M1=−0.6 g+/−0.21 g, -1.5%, \*\*\*; M3=−0.6 g+/−0.17 g, -1.6%, \*\*\*; M4=−0.9 g+/−0.13 g, -2.4%, \*\*\*), 12 nmol/kg dose group (M1=−0.9 g+/−0.11 g, -2.3%, \*\*\*; M3=−0.7 g+/−0.18 g, -1.6%, \*\*\*; M4=−0.6 g+/−0.16 g, -1.7%, \*\*\*), and 40 nmol/kg dose group (M1=−1.0 g+/−0.14 g, -2.5%, \*\*\*; M3=−0.6 g+/−0.09 g, -1.5%, \*\*\*; M4=−0.8 g+/−0.22 g, -2.1%, \*\*\*). 7 Days post-administration of the fusion molecules vs vehicle control, the following body weights were recorded (% decrease=Delta difference vs. pre-administration dose group weight). Vehicle=+1.2 g+/−0.25 g, +3.1%), 4 nmol/kg dose group (M1=−1.3 g+/−0.30 g, -3.3%, \*\*\*; M3=−1.1 g+/−0.32 g, -2.8%, \*\*\*; M4=−2.0 g+/−0.29 g, -5.0%, \*\*\*), 12 nmol/kg dose group (M1=−1.8 g+/−0.34 g, -4.7%, \*\*\*; M3=−1.4 g+/−0.43 g, -3.6%, \*\*\*; M4=−1.5 g+/−0.32 g, -3.7%, \*\*\*), and 40 nmol/kg dose group (M1=−2.6 g+/−0.28 g, -6.7%, \*\*\*; M3=−2.1 g+/−0.28 g, -5.4%, \*\*\*; M4=−2.6 g+/−0.31 g, -6.7%, \*\*\*).

The data in FIGS. 6 and 7 demonstrate that HSA fusions with linker optimization and N-terminal truncations of GDF15 are active, and that such fusion molecules represent a viable approach for enhancing certain beneficial properties of GDF15 molecules.

Example 3

Human GDF15 Muteins with Improved Physical Properties

The data set forth in Example 3 address solubility limitations associated with surface hydrophobicities and hydrophilicities inherent to mature human GDF15. In addition, the effect on solubility of introducing N-linked Glycosylation consensus site(s) along the sequence of mature human GDF15 was evaluated. In order to facilitate assessment of expression characteristics; glycosylation properties and solubility of mature, recombinant human GDF15 muteins, all were constructed as mature muteins fused with an IgK signal peptide sequence and are depicted in FIG. 8A. 17 GDF15 muteins (denoted M5-M21; SEQ ID NOs: 81-97, respectively) were generated. For M16, an N-terminal deleted version: ΔN3-M16 mutein was generated and its solubility was determined. M5 mutein contains two N-linked Glycosylation consensus sites introduced by substituting the D at position 5 in the wt GDF15 (SEQ ID NO: 1) with T and by substituting the R at position 21 in the wt GDF15 (SEQ ID NO: 1) with N. In muteins M6-M21, one N-linked Glycosylation consensus site was introduced (see FIG. 8A). It is noted that although the muteins include an IgK signal sequence at the N-terminus for the purpose of referring to the position of the substitution, the residues are numbered as the position of the corresponding residue in SEQ ID NO: 1. Thus, for example, although T is present at position 27 in M5 mutein, it is referred to as position 5, since the position of the corresponding D residue in SEQ ID NO: 1 is 5.

Solubility assessments were performed on muteins (in 0.01% Formic acid) via a spike of in 10×PBS+0.5M Tris pH 7.0, a stringent buffer for which improvements in the solubility of a mutein can be assessed relative to mature human GDF15.

Assessment of solubility was determined based on Absorbance at 280 nm using Beer's law calculated using Extinction Coefficient (mature human GDF15=14,400/monomer) and molecular weight (mature human GDF15=12,278 Da/monomer).

Before being assessed for solubility, each of the engineered N-Glycan muteins set forth in FIG. 8A and ΔN3-M16 mutein was evaluated both for secretion as a folded GDF15 homodimer into mammalian tissue culture media and for N-glycan site occupancy. As set forth in FIG. 9, fourteen of the eighteen glycosylated muteins were secreted as folded GDF15 homodimers, whereas M8, M10, M14 and M15 did not result in dimer formation and were expressed as aggregates. All fourteen expressed glycosylation muteins that secreted as homodimers were then assessed by LC/MS and SDS-PAGE gel shift to determine occupancy of N-Glycan groups on the consensus site following purification from conditioned media. In all fourteen cases, the expressed muteins contained high degree of occupancy and a sub-set were analyzed for improvement to physical properties such as solubility.

Engineered N-Glycan GDF15 muteins which were both secreted as homodimers and possessed high glycan occupancy within the consensus site were monitored for improvements to solubility relative to mature human GDF15. The inflection point at which turbidity begins to occur is accepted as the maximum solubility for each mutein. Muteins were categorized into one of five groups depending on their level of solubility: <0.2 mg/mL=+; ≥0.2 mg/mL=++; ≥0.5 mg/mL=+++; ≥1.0 mg/mL=++++; ≥5.0 mg/mL=+++++. Each of the N-Glycan GDF15 muteins that was assessed exhibited improved solubility compared to mature human GDF15: M5: ++++, M7: +++, M11: +++, M12: +++, M13: ++++, M16: +++++, ΔN3-M16: +++++, M17: +++++, M20: ++++, M21: +++.

Example 4

Effect of M16, ΔN3-M16 and M17 Muteins on Food Intake in DIO Mouse Model

The effect of subcutaneously administered glycomuteins on food intake was evaluated. Glycomutein M16 (SEQ ID NO: 92) and M17 (SEQ ID NO: 93) are described in Example 3 above. The glycomutein designated as ΔN3-M16 was also evaluated. The sequence for ΔN3-M16 glycomutein is provided as below:

(SEQ ID NO: 100)
mdmrvpaqllglllllwlrgarcGDHCPLGPGRCCRLHTVRASLEDLGWA

DWVLSPREVQVTMCIGACPSQFRAANMHAQIKTSLHRLKPDTVPAPCCV

PASYNPMVLIQNTTTGVSLQTYDDLLAKDCHCI

It is noted that the polypeptides administered to the mice do not include the IgK signal sequence (mdmrvpaqllglllwlrgarc, SEQ ID NO: 101) as the IgK signal sequence is cleaved off from the secreted polypeptide by a signal peptidase expressed by the cells (293 cells).

Figure 10:
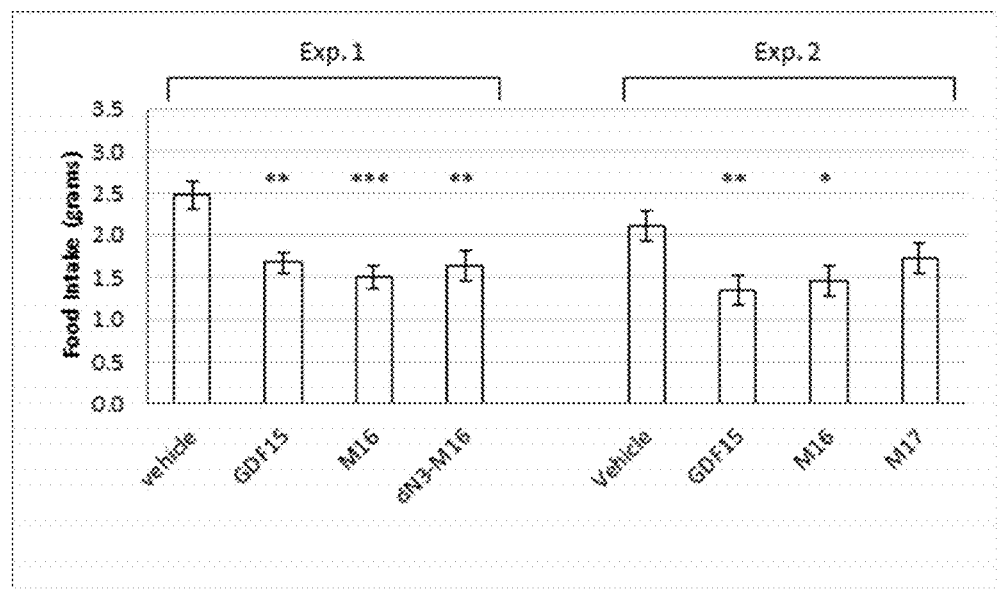
FIG. 10 depicts the effect on food intake in Diet-induced obese (DIO) mice following a single sub-cutaneous administration of vehicle (PBS), GDF15, M16, ΔN3-M16 and M17 polypeptides (1 mg/kg (40 nmol/Kg)).

Referring to FIG. 10, subcutaneous administration of a single 1.0 mg/kg (40 nmol/Kg) dose of PBS vehicle, mature human GDF15 or a N-glycan mutein was given to 17 week-old male DIO mice (n=9). Food intake (grams/animal) over a 24-hour period following the subcutaneous administration was monitored. P-values were determined by an unpaired student T-test relative to a vehicle (PBS) control group.

As depicted in FIG. 10, administration of the glycomuteins resulted in reduction in food intake. In each group of mice, p-values (*, $p<0.05$; , $p<0.01$; *, $p<0.001$) were determined by student's unpaired T-test comparing the food intake to vehicle control group. Wild type GDF15 also reduced food intake.

Example 5

Effect of M16, ΔN3-M16 and M17 Muteins on Body Weight in DIO Mouse Model

The effect of subcutaneously administered glycomuteins on body weight was evaluated. Subcutaneous administration of a single 1.0 mg/kg (40 nmol/Kg) dose of PBS vehicle, mature human GDF15 or a N-glycan mutein (M16, M17, and ΔN3-M16) was given to 17 week-old male DIO mice (n=9). Body weight over a 24-hour period following the subcutaneous administration was monitored. P-values were determined by an unpaired student T-test relative to a vehicle (PBS) control group.

Figure 11:
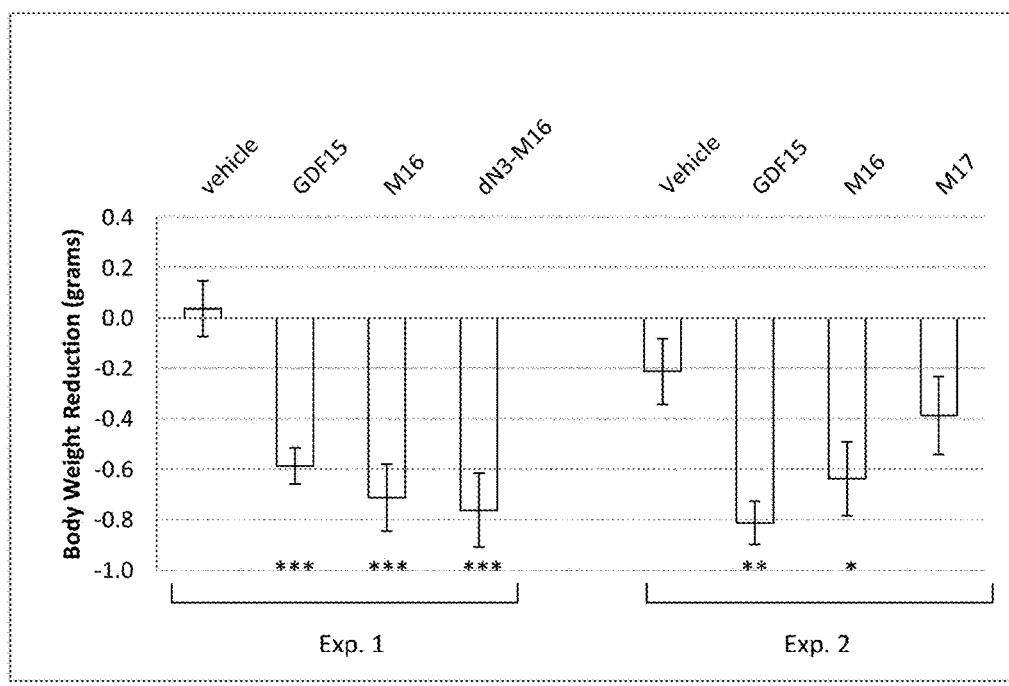
FIG. 11 depicts the effect on body weight in DIO mice following a single sub-cutaneous administration of vehicle (PBS), GDF15, M16, ΔN3-M16 and M17 polypeptides (1 mg/kg (40 nmol/Kg)).

Administration of the glycomuteins resulted in reduction in body weight (FIG. 11). In each group of mice, p-values (*, $p<0.05$; , $p<0.01$; *, $p<0.001$) were determined by student's unpaired T-test comparing the food intake to vehicle control group. Wild type GDF15 also reduced body weight.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A dimer comprising two covalently joined polypeptides, wherein the two polypeptides each comprise the amino acid sequence set forth in one of:
   i) SEQ ID NO: 13;
   ii) SEQ ID NO: 14;
   iii) SEQ ID NO: 30;
   iv) SEQ ID NO: 31;
   v) SEQ ID NO: 92;
   vi) SEQ ID NO: 93;
   vii) SEQ ID NO: 13 with a substitution of T at residue 93 with S;
   viii) SEQ ID NO: 14 with a substitution of T at residue 95 with S;
   ix) SEQ ID NO: 30 with a substitution of T at residue 90 with S;
   x) SEQ ID NO: 31 with a substitution of T at residue 92 with S;
   xi) SEQ ID NO: 92 with a substitution of T at residue 115 with S; or
   xii) SEQ ID NO: 93 with a substitution of T at residue 117 with S.

2. The dimer of claim 1, wherein the two polypeptides each comprise the amino acid sequence set forth in one of:
   i) SEQ ID NO: 13;
   ii) SEQ ID NO: 14;
   iii) SEQ ID NO: 30;
   iv) SEQ ID NO: 31;
   v) SEQ ID NO: 92; or
   vi) SEQ ID NO: 93.

3. The dimer of claim 1, wherein the two polypeptides each comprise the amino acid sequence set forth in one of:
   vii) SEQ ID NO: 13 with a substitution of T at residue 93 with S;
   viii) SEQ ID NO: 14 with a substitution of T at residue 95 with S;
   ix) SEQ ID NO: 30 with a substitution of T at residue 90 with S;
   x) SEQ ID NO: 31 with a substitution of T at residue 92 with S;
   xi) SEQ ID NO: 92 with a substitution of T at residue 115 with S; or
   xii) SEQ ID NO: 93 with a substitution of T at residue 117 with S.

4. The dimer of claim 1, wherein the two polypeptides each comprise the amino acid sequence set forth in one of:
   i) SEQ ID NO: 13;
   ii) SEQ ID NO: 14;
   iii) SEQ ID NO: 30; or
   iv) SEQ ID NO: 31.

5. The dimer of claim 1, wherein the two polypeptides each comprise the amino acid sequence set forth in SEQ ID NO: 13.

6. The dimer of claim 1, wherein the two polypeptides each comprise the amino acid sequence set forth in SEQ ID NO: 14.

7. The dimer of claim 1, wherein the two polypeptides each comprise the amino acid sequence set forth in SEQ ID NO: 13 or 14.

8. The dimer of claim 1, wherein the two polypeptides each comprise the amino acid sequence set forth in SEQ ID NO: 30.

9. The dimer of claim 1, wherein the two polypeptides each comprise the amino acid sequence set forth in SEQ ID NO: 31.

10. The dimer of claim 1, wherein at least one of the two polypeptides is fused to a heterologous polypeptide.

11. The dimer of claim 10, wherein the heterologous polypeptide is serum albumin, maltose binding protein, or immunoglobulin Fc polypeptide.

12. The dimer of claim 11, wherein the heterologous polypeptide is serum albumin, and the serum albumin is human serum albumin, cyno serum albumin or bovine serum albumin.

13. The dimer of claim 11, wherein the heterologous polypeptide is immunoglobulin Fc polypeptide.

14. The dimer of claim 10, wherein the heterologous polypeptide is conjugated to the N-terminus of at least one of the two polypeptides.

15. The dimer of claim 10, wherein the heterologous polypeptide is conjugated to the C-terminus of at least one of the two polypeptides.

16. The dimer of claim 1, wherein the dimer is N-glycosylated.

17. An N-glycosylated dimer comprising two polypeptides covalently joined to each other, wherein the two polypeptides each comprise the amino acid sequence set forth in SEQ ID NO: 30.

18. The dimer of claim 16, wherein the two polypeptides each comprise the amino acid sequence set forth in SEQ ID NO: 13.

19. A nucleic acid molecule encoding at least one of the polypeptides of claim 1.

20. A vector comprising the nucleic acid molecule of claim 19.

21. A host cell that expresses the dimer of claim 1.

22. A host cell comprising the nucleic acid molecule of claim 19.

23. A pharmaceutical composition, comprising the dimer of claim 1, and a pharmaceutically acceptable diluent, carrier or excipient.

24. The pharmaceutical composition of claim 23, further comprising at least one additional prophylactic or therapeutic agent.

25. A sterile container comprising the pharmaceutical composition of claim 23.

26. The sterile container of claim 25, wherein the sterile container is a syringe.

27. A kit comprising the sterile container of claim 25.

28. A method of making the dimer of claim 1, the method comprising:
   culturing a host cell expressing a polypeptide comprising the amino acid sequence set forth in:
   i) SEQ ID NO: 13;
   ii) SEQ ID NO: 14;
   iii) SEQ ID NO: 30;
   iv) SEQ ID NO: 31;
   v) SEQ ID NO: 92;

vi) SEQ ID NO: 93;
vii) SEQ ID NO: 13 with a substitution of T at residue 93 with S;
viii) SEQ ID NO: 14 with a substitution of T at residue 95 with S;
ix) SEQ ID NO: 30 with a substitution of T at residue 90 with S;
x) SEQ ID NO: 31 with a substitution of T at residue 92 with S;
xi) SEQ ID NO: 92 with a substitution of T at residue 115 with S; or xii) SEQ ID NO: 93 with a substitution of T at residue 117 with S, and purifying the expressed dimer.

29. A method of treating obesity in a mammalian subject, the method comprising administering to the subject the dimer of claim 1, wherein the dimer is administered in an amount effective in treating obesity in the subject.

30. A method of treating hyperglycemia in a mammalian subject, the method comprising administering to the subject the dimer of claim 1, wherein the dimer is administered in an amount effective in treating the hyperglycemia in the subject.

31. The method of claim 29, wherein the treating results in reduction in food intake by the subject.

32. The method of claim 29, wherein the subject is a human and the treating results in a reduction in body weight in the subject.

33. The method of claim 30, wherein the treating results in a reduction in body weight in the subject.

34. The method of claim 30, wherein the treating results in a reduction in food intake by the subject.

35. The method of claim 30, wherein the subject is a human and the treating results in a reduction in blood glucose in the subject.

36. The method of claim 30, wherein the subject has diabetes mellitus.

37. The method of claim 29, wherein the subject is human.

38. The method of claim 30, wherein the subject is obese.

39. The method of claim 29, wherein the administering is by parenteral injection.

40. The method of claim 39, wherein the parenteral injection is subcutaneous.

41. The method of claim 29, wherein the dimer comprises two polypeptides, each polypeptide comprising the amino acid sequence set forth in SEQ ID NO: 30.

42. The method of claim 30, wherein the dimer comprises two polypeptides, each polypeptide comprising the amino acid sequence set forth in SEQ ID NO: 30.

43. The dimer of claim 16, wherein the dimer is a homodimer in which the two polypeptides comprise the same amino acid sequence.

44. A pharmaceutical composition, comprising:
an N-glycosylated dimer comprising two polypeptides covalently joined to each other, wherein the two polypeptides each comprise the amino acid sequence set forth in SEQ ID NO: 30; and, a pharmaceutically acceptable diluent, carrier, or excipient.

45. A method of treating obesity in a human subject, comprising:
administering to the human subject the dimer of claim 16, wherein the dimer is administered in an amount effective in treating the obesity in the human subject.

46. The method of claim 45, wherein the treating results in reduction in food intake by the human subject.

47. A method for treating hyperglycemia in a human subject, comprising:
administering to the human subject the dimer of claim 16, wherein the dimer is administered in an amount effective in treating the hyperglycemia in the human subject.

48. The method of claim 47, wherein the treating results in a reduction in body weight in the human subject.

49. The method of claim 47, wherein the treating results in a reduction in food intake by the human subject.

50. The method of claim 47, wherein the human subject has diabetes mellitus.

51. The method of claim 47, wherein the treating results in reduction in blood glucose in the human subject.

52. The method of claim 47, wherein the human subject is obese.

53. A method of treating obesity in a human subject, comprising:
administering to the human subject the dimer of claim 26, wherein the dimer is administered in an amount effective in treating the obesity in the human subject.

54. The method of claim 53, wherein the treating results in reduction in food intake by the human subject.

55. A method for treating hyperglycemia in a human subject, comprising:
administering to the human subject the dimer of claim 17, wherein the dimer is administered in an amount effective in treating the hyperglycemia in the human subject.

56. The method of claim 55, wherein the treating results in a reduction in body weight in the human subject.

57. The method of claim 55, wherein the treating results in a reduction in food intake by the human subject.

58. The method of claim 55, wherein the human subject has diabetes mellitus.

59. The method of claim 55, wherein the treating results in reduction in blood glucose in the human subject.

60. The method of claim 55, wherein the human subject is obese.

61. A pharmaceutical composition, comprising:
an N-glycosylated dimer wherein the dimer comprises two polypeptides covalently joined to each other, wherein the two polypeptides each consist of the amino acid sequence set forth in SEQ ID NO: 30; and, a pharmaceutically acceptable diluent, carrier, or excipient.

* * * * *

UNITED STATES PATENT AND TRADEMARK OFFICE
CERTIFICATE OF CORRECTION

PATENT NO. : 9,834,586 B2
APPLICATION NO. : 14/811578
DATED : December 5, 2017
INVENTOR(S) : Darrin Anthony Lindhout It is certified that error appears in the above-identified patent and that said Letters Patent is hereby corrected as shown below:

In the Claims

In Claim 53 at Column 168, Line 27, (approx.):
Delete "26" and replace with --17--.

Signed and Sealed this
Twenty-third Day of October, 2018

Andrei Iancu
*Director of the United States Patent and Trademark Office*